United States Patent
Chikauchi et al.

(10) Patent No.: US 8,093,294 B2
(45) Date of Patent: Jan. 10, 2012

(54) METALLO-β-LACTAMASE INHIBITORS

(75) Inventors: Ken Chikauchi, Kawasaki (JP); Mizuyo Ida, Yokohama (JP); Takao Abe, Sakado (JP); Yukiko Hiraiwa, Sagamihara (JP); Akihiro Morinaka, Kawasaki (JP); Toshiaki Kudo, Yokohama (JP)

(73) Assignee: Meiji Seika Kaisha, Ltd., Tokyo-to (JP)

( * ) Notice: Subject to any disclaimer, the term of this patent is extended or adjusted under 35 U.S.C. 154(b) by 850 days.

(21) Appl. No.: 11/889,296

(22) Filed: Aug. 10, 2007

(65) Prior Publication Data
US 2008/0090825 A1 Apr. 17, 2008

Related U.S. Application Data

(63) Continuation-in-part of application No. PCT/JP2006/318879, filed on Sep. 22, 2006.

(30) Foreign Application Priority Data

Sep. 22, 2005 (JP) .................. 2005-275487

(51) Int. Cl.
*A61K 31/19* (2006.01)
*A61K 31/43* (2006.01)
*A61K 31/545* (2006.01)

(52) U.S. Cl. .................. 514/574; 514/192; 514/200

(58) Field of Classification Search .................. 514/574, 514/192, 200
See application file for complete search history.

(56) References Cited

U.S. PATENT DOCUMENTS

| 5,409,917 A * | 4/1995 | Robinson et al. ............. 514/200 |
| 6,630,510 B1 | 10/2003 | Balkovec et al. |
| 2003/0078418 A1 | 4/2003 | Balkovec et al. |
| 2003/0207859 A1 | 11/2003 | Balkovec et al. |

FOREIGN PATENT DOCUMENTS

| CN | 1363271 | 8/2002 |
| JP | 57-207245 | 12/1982 |
| JP | 2000-143511 | 5/2000 |
| JP | 2002-363156 | 12/2002 |
| WO | 97/40006 | 10/1997 |
| WO | WO 01/28340 | * 4/2001 |
| WO | 01/30148 | 5/2001 |
| WO | 01/30149 | 5/2001 |

OTHER PUBLICATIONS

West, Solid state chemistry and its application, Wilsy, New York, 1988. pp. 358, 365.*
Vippagunta et al. "Crystalline solid," Advanced, drug, Delivery, 2001, vol. 48, pp. 3-26.*
Ulrich "Crystallization," Chapter 4, Kirk-Othmer Encyclopedia of Chemical techology, John, Wiley and Sons, 2002.*
International Search Report issued Dec. 19, 2006 in the International (PCT) Application PCT/JP2006/318879.
C. Girard et al., "Steroselective alkylation of the Lithium Di-Enolate of Bis-2,3-Carbomethoxy Bicyclo[2 2 1] Hept-5-ene. A Convenient Synthesis of Mono- and Disubstituted Fumarate Esters", Tetrahedron Letters, vol. 23, No. 36, pp. 3683-3686, 1982.
V.V. Fotin, et al., "Reactions of α-Bromo Esters with Zinc and Acyl Chlorides in the Presence of Dioxane", Russian Journal of Organic Chemistry, vol. 35, No. 9, pp. 1278-1281, 1999.
Albert Gossauer et al., "Syntheses of bile pigments, V. Stereospecific total synthesis of diastereomeric mesobilirhodins and isomesobilirhodins", Justus Liebigs Annalen der Chemie, No. 4, pp. 664-686, 1977.

* cited by examiner

*Primary Examiner* — Shengjun Wang
(74) *Attorney, Agent, or Firm* — Wenderoth, Lind & Ponack, L.L.P.

(57) ABSTRACT

A new metallo-β-lactamase inhibitor which acts as a medicament for inhibiting the inactivation of β-lactam antibiotics and recovering anti-bacterial activities is disclosed. The maleic acid derivatives having the general formula (I) have metallo-β-lactamase inhibiting activities. It is possible to recover the anti-bacterial activities of β-lactam antibiotics against metallo-β-lactamase producing bacteria by combining the compound of the general formula (I) with β-lactam antibiotics.

(I)

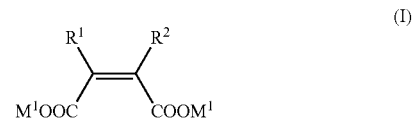

11 Claims, No Drawings

METALLO-β-LACTAMASE INHIBITORS

RELATED APPLICATION

This application is a continuation-in-part of International Application PCT/JP2006/318879 filed Sep. 22, 2006 designating the United States of America and claiming the priority of Japanese Patent 2005-275487 filed Sep. 22, 2005, all of which are incorporated herein by reference.

BACKGROUND OF THE INVENTION

1. Field of the Invention

The present invention relates to a metallo-β-lactamase inhibitor comprising a maleic acid compound as an effective ingredient, and more particularly, it relates to a pharmaceutical composition to improve the effectiveness against metallo-β-lactamase producing resistant bacteria in combination with β-lactam antibiotics for the therapy of bacterial infection in animal or human being and a method for treating the bacterial infections.

2. Background Art

β-lactamase plays an important role in the acquisition of resistance against β-lactam antibiotics in bacteria. Particularly, metallo-β-lactamases which contains zinc at their active center and exhibits wide ranges of substrate specificities are at issue due to the fact that the metallo-β-lactamases also hydrolyze carbapenem antibiotics which are relatively stable to serine-β-lactamase. In fact, metallo-β-lactamase producing bacteria are a menace to clinically important β-lactam pharmaceuticals due to the acquisition of resistance to such pharmaceuticals. Metallo-β-lactamases have been confirmed in a variety of bacterial strains such as *Bacillus cereus*, *Bacteriocides fragilis*, *Escherichia coli*, *Aeromonas hydrophila*, *Klebsiella pneumoniae*, *Pseudomonas aeruginosa*, *Serratia marcescens*, *Stenotrophomonas maltophilia*, *Shigella flexneri*, *Alcaligenes xylosoxidans*, *Legionella gormanii*, *Chryseobacterium meningosepticum*, *Chryseobacterium indologenes*, *Acinetobacter baumannii*, *Citrobacter freundii*, and *Enterobacter cloacae*. Particularly, *Pseudomonas aeruginosa* causes serious problem because of its conspicuous multidrug resistance. Clavulanic acid, sulbactam, and tazobactam which are now used as β-lactamase inhibitors are effective against serine-β-lactamase having serine as an active center, but these drugs exhibit not inhibiting effect on metallo-β-lactamases.

Therefore, metallo-β-lactamase inhibitors have been increasingly necessitated in order to recover the effectiveness of β-lactam antibiotics such as imipenem against metallo-β-lactamase producing resistant bacteria.

Since a metallo-β-lactamase coded on a transferable plasmid has first been reported in *Pseudomonas aeruginosa*, many compounds have been reported as those having metallo-β-lactamase inhibiting activities. In WO98/17639, WO97/30027, WO98/40056, WO98/39311, and WO97/10225, certain β-thiopropionyl-amino acid derivatives have been described together with their uses as the inhibitor against the metallo-β-lactamases. Also, several literatures disclose thiols and thioesters as metallo-β-lactamase inhibitors (Biol. Pharm. Bull. 1997, 20, 1136; FEMS Microbiology Letters 1997, 157, 171; Antimicrob. Agents Chemother. 1997, 41, 135; Chem. Commun. 1998, 1609; Biochem. J. 1998, 331, 703; WO00/076962). Furthermore, there are disclosed succinic acid compounds as the metallo-β-lactamase inhibitors in WO01/030148 and WO01/030149. In addition, there is a literature in which general situations on various metallo-β-lactamase inhibitive compounds and metallo-β-lactamase producing bacteria are described (Clin. Microbiol. Rev. 2005, 18, 306). However, none of the literatures described above disclose or suggest the maleic acid derivatives as the compounds of the present invention.

In order to exert the effect of the metallo-β-lactamase inhibitor against the metallo-β-lactamase producing resistant bacteria actually in clinical practice, it is essential to recover the effectiveness in combination with β-lactam antibiotics. However, there has hitherto been described scarcely such combination effect against bacterial species including *Pseudomonas aeruginosa* which is at issue in the medical field. There is at present no metallo-β-lactamase inhibitor which is effective on infections in human beings and animals.

With respect to the maleic acid derivatives, dimethyl maleate has been disclosed in Japanese Patent Laid-Open Publication No. 57-207245, dimethyl maleate and diethyl maleate, i.e. the compounds having the general formula (I) wherein $M^1$ represents a hydrogen atom, and the like have been disclosed in Acta Chem. Scand. 1964, 18, 1276, and 3-methyl-2-tetradecanyl maleate has been disclosed in Japanese Patent Publication No. 7-91213. However, the salts or esters having a group which can be hydrolyzed in vivo of these derivatives have not been described in them.

Also, there is disclosed in Bioorg. Med. Chem., 2000, 8, 571 2-hydroxymethyl-3-tetradecanyl maleate but not the other 2-hydroxymethyl-3-lower alkyl maleate. Furthermore, there is disclosed in J. Am. Chem. Soc. 1955, 77, 6702 dicarboxylic acids having a cyclic alkyl group in the side chain, which are mono-substituted fumarate derivatives but not maleate derivatives. There is disclosed in J. Org. Chem. 1984, 49, 1985 maleic acid derivatives, one of which has an alkylthio substituent, but the other has an alkenyl group. There are disclosed in WO 91/08775 and Tetrahedron Lett. 1988, 29, 3869 maleic acid ester compounds mono-substituted with an alkoxy group, but a carboxylic acid thereof, i.e. the compound having the general formula (I) wherein $M^1$ represents a hydrogen atom, or a salt thereof have not been disclosed in these literatures. In addition, a compound having a dihydrofuranyl group has been described in Nord. Pulp Pap. Res. J. 1994, 9, 84, and a compound having a pyridinium group has been described in Angew. Chem., 1990, 102, 1164, but no metallo-β-lactamase inhibiting activity has been indicated in therein.

SUMMARY OF THE INVENTION

Accordingly, the object of the present invention is to provide a new metallo-β-lactamase inhibitor which acts as a medicament for inhibiting the inactivation of β-lactam antibiotics and recovering anti-bacterial activities.

The present inventors have now found that maleate derivatives and pharmacologically acceptable salts thereof have an inhibitory effect against metallo-β-lactamases. Furthermore, it has been found that these compounds are effective for recovering the activities of β-lactam antibiotics against the metallo-β-lactamase producing bacteria. The present invention is based on such findings.

According to one aspect of the present invention, there is provided a process for treating bacterial infections, which comprises administering the compound represented by the following formula (I), or a salt or solvate thereof to mammals including human being:

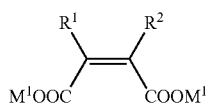

(I)

in which
$R^1$ represents a $C_{2-6}$ alkyl group, a $C_{3-7}$ cycloalkyl group, a hydroxymethyl group, a —$C_{1-3}$ alkylene-phenyl group, a —$C_{0-1}$-alkylene-heterocycle, a —O—$C_{1-6}$ alkyl group, or a —S—$C_{1-6}$ alkyl group, all of which may be substituted,
$R^2$ represents a $C_{1-6}$ alkyl group, a $C_{3-7}$ cycloalkyl group, a hydroxymethyl group, a —$C_{1-3}$ alkylene-phenyl group, a —$C_{0-1}$, alkylene-heterocycle, a —O—$C_{1-6}$ alkyl group, or a —S—$C_{1-6}$ alkyl group, all of which may be substituted,
each $M^1$ independently represents a hydrogen atom, a pharmaceutically acceptable cation, or a pharmaceutically acceptable group which may be hydrolyzed in vivo.

β-Lactam antibiotics are in general administered concomitantly or sequentially with the compound represented by the general formula (I), or a salt or solvate thereof.

Also, according to another aspect of the present invention, there is provided a pharmaceutical composition comprising the metallo-β-lactamase inhibitor, the β-lactam antibiotics, and optionally a pharmaceutically acceptable carrier.

In addition, according to another aspect of the present invention, there is provided a compound represented by the following general formula (II), or a salt or solvate thereof:

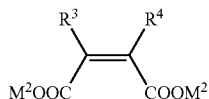

(II)

in which
$R^3$ represents a $C_{1-6}$ alkyl group or a $C_{3-7}$ cycloalkyl group, all of which may be substituted, provided that when $R^3$ is a $C_{1-2}$ linear alkyl group, this has at least one substituent,
$R^4$ represents a $C_{1-6}$ alkyl group or a $C_{3-7}$ cycloalkyl group, all of which may be substituted,
each $M^2$ independently represents a hydrogen atom, a pharmaceutically acceptable cation, or a pharmaceutically acceptable group which may be hydrolyzed in vivo.

Also, according to another aspect of the present invention, there is provided a compound represented by the following general formula (III), or a salt or solvate thereof:

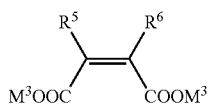

(III)

in which
$R^5$ represents an ethyl group,
$R^6$ represents a $C_{1-3}$ linear alkyl group,
each $M^3$ independently represents a pharmaceutically acceptable cation, or a pharmaceutically acceptable group which may be hydrolyzed in vivo.

Also, according to another aspect of the present invention, there is provided a compound represented by the following general formula (IV), or a salt or solvate thereof:

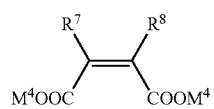

(IV)

in which
$R^7$ represents a $C_{1-6}$ alkyl group, a $C_{3-7}$ cycloalkyl group, a —$C_{1-3}$ alkylene-phenyl group, a —$C_1$ alkylene-ring A, a —O—$C_{1-6}$ alkyl group, or a —S—$C_{1-6}$ alkyl group, all of which may be substituted,
$R^8$ represents a —$C_{1-3}$ alkylene-phenyl group, a —$C_{0-1}$ alkylene-ring A, a —O—$C_{1-6}$ alkyl group, or a —S—$C_{1-6}$ alkyl group, all of which may be substituted,
the ring A represents a five- to ten-membered mono- or bicyclic heterocyclic ring having 1-4 hetero atoms selected from nitrogen, oxygen and sulfur atoms,
each $M^4$ independently represents a hydrogen atom, a pharmaceutically acceptable cation, or a pharmaceutically acceptable group which may be hydrolyzed in vivo, provided that when $R^7$ is a $C_{1-6}$ alkyl group, $R^8$ excludes dihydrofuran.

Also, according to another aspect of the present invention, there is provided a compound represented by the following general formula (V), or a salt or solvate thereof:

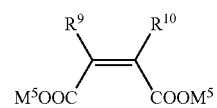

(V)

in which
$R^9$ represents a $C_{1-6}$ alkyl group, a $C_{3-7}$ cycloalkyl group, a —$C_{1-3}$ alkylene-phenyl group, a —$C_{0-1}$ alkylene-ring B, a —O—$C_{1-6}$ alkyl group, or, a —S—$C_{1-6}$ alkyl group, all of which may be substituted,
$R^{10}$ represents a —$C_{1-3}$ alkylene-phenyl group, a —$C_{0-1}$ alkylene-ring B, a —O—$C_{1-6}$ alkyl group, or a —S—$C_{1-6}$ alkyl group, all of which may be substituted,
the ring B represents pyridine, piperidine or tetrahydropyran,
each $M^5$ independently represents a hydrogen atom, a pharmaceutically acceptable cation or a pharmaceutically acceptable group which may be hydrolyzed in vivo, provided that the case when $R^9$ represents pyridinium is excluded.

DETAILED DESCRIPTION OF THE INVENTION

Definition

Unless otherwise specified, the terms "$C_{1-6}$", "$C_{2-6}$", "$C_{3-7}$", "$C_{1-3}$", "$C_{0-1}$", "$C_{2-3}$", "$C_1$", and the like denote the number of carbon atoms, and for example, "a $C_{1-6}$ alkyl group" represents an alkyl group having 1-6 carbon atoms. Also, $C_0$ represents a bond. Lower preferably means $C_{1-6}$, and in the case of the cyclic group it preferably means $C_{3-7}$.

The term "halogen atom" represents a fluorine atom, a chlorine atom, a bromine atom, or an iodine atom.

The term "hetero atom" represents a nitrogen atom, an oxygen atom, or a sulfur atom.

As herein used, the terms "alkyl group" or "alkoxy group" as a group or as a part of a group preferably mean a linear or branched alkyl group having 1-6 carbon atoms or alkoxy group having 1-6 carbon atoms. Examples of "alkyl" include methyl, ethyl, n-propyl, i-propyl, n-butyl, i-butyl, s-butyl, t-butyl, n-pentyl, neopentyl, i-pentyl, t-pentyl, n-hexyl, i-hexyl, and the like. Examples of "alkoxy" include methoxy, ethoxy, n-propoxy, i-propoxy, n-butoxy, i-butoxy, s-butoxy, t-butoxy, n-pentyloxy, neopentyloxy, i-pentyloxy, t-pentyloxy, n-hexyloxy, i-hexyloxy, and the like. Also, the term lower alkyl group preferably means a $C_{1-6}$ alkyl group, as defined above.

As herein used, the term "cycloalkyl group" as a group or as a part of a group preferably means a mono-cyclic alkyl group having 3-7 carbon atoms. Examples of "cycloalkyl" include cyclopropyl, cyclobutyl, cyclopentyl, cyclohexyl, cycloheptyl, and the like. Also, the term lower cycloalkyl group preferably means a $C_{3-7}$ cycloalkyl group, as defined above.

As herein used, the term "alkylene" as a group or as a part of a group preferably means an alkylene group having 1-3 carbon atoms. Examples of "alkylene" include methylene, ethylene, propylene, and the like.

As herein used, the term "heterocyclic ring" includes a five- to fourteen-membered mono- to tri-cyclic heterocyclic ring containing 1-4 hetero atoms selected from nitrogen, oxygen and sulfur atoms, more preferably a five- to ten-membered mono- to bi-cyclic heterocyclic ring containing 1-4 hetero atoms selected from nitrogen, oxygen and sulfur atoms. Preferred examples include tetrahydrofuran, furan, pyrrolidine, piperidine, pyrazolidine, imidazolidine, piperazine, morpholine, thiomorpholine, pyrrole, thiophene, oxazole, isoxazole, thiazole, isothiazole, imidazole, pyrazole, pyridine, pyridazine, pyrimidine, pyrazine, triazole, tetrazole, thiadiazole, azetidine, thiazoline, quinuclidine, triazine, isobenzofuran, indole, indolizine, chromene, quinoline, isoquinoline, cinnoline, quinazoline, quinoxaline, phthalazine, purine, pteridine, and the like.

The term "aryl" means preferably aromatic rings such as phenyl, substituted phenyl, and the like as well as fused rings such as naphthyl, phenanthrenyl, fluorenyl, anthryl, and the like. Preferred aryl groups include a phenyl group, a naphthyl group and a fluorenyl group.

As herein used, the term "which may be substituted" means that which may be substituted preferably by 1-6 substituents, more preferably 1-3 substituents, and the term "substituents" include a hydroxyl group, a thiol group, a $C_{1-6}$ alkyl group, a $C_{1-6}$ alkoxy group, a S—$C_{1-6}$ alkyl group, amino, a mono-substituted amino group, a di-substituted amino group, an amide group, a guanidyl group, an N-substituted amide group, an N,N-disubstituted amide group, a halogen atom, a carboxyl group, a phenyl group, a substituted phenyl group, a $C_{1-6}$ alkylcarbonyl group, a heterocycle, a heterocyclic carbonyl group, and the like, and the phenyl group may be fused. Preferred substituted groups include a hydroxyl group, a $C_{1-6}$ alkyl group, a $C_{1-6}$ alkoxy group, an amino group, a mono-substituted amino group, a di-substituted amino group, an amide group, a guanidyl group, an N-substituted amide group, an N,N-disubstituted amide group, a halogen atom, a carboxyl group, a phenyl group, which may be fused, a substituted phenyl group, a $C_{1-6}$ alkylcarbonyl group, a heterocycle, and a heterocyclic carbonyl group.

The "substituents" described above including a $C_{1-6}$ alkyl group, a $C_{1-6}$ alkoxy group, an S—$C_{1-6}$ alkyl group, and a $C_{1-6}$ alkylcarbonyl group, and an alkyl group and an alkoxy group as a part of a group have the same meanings as described above. Also, a halogen atom has the same meaning as described above. The $C_{1-6}$ alkyl group, the $C_{1-6}$ alkoxy group, the S—$C_{1-6}$ alkyl group and the $C_{1-6}$ alkylcarbonyl group may be further substituted by the "substituents" described above. Above all, the $C_{1-6}$ alkyl group and the $C_{1-6}$ alkoxy group may be substituted by a hydroxyl group, an amino group, a mono-substituted amino group, a di-substituted amino group, an amide group, a guanidyl group, an N-substituted amide group, an N,N-disubstituted amide group, a carboxyl group, a heterocycle, a phenyl group, a substituted phenyl group, and the like.

When the "substituents" described above is a carboxyl group or a group having a carboxyl group as a part of the group, the carboxyl group may be a pharmaceutically acceptable cation or a pharmaceutically acceptable group which may be hydrolyzed in vivo, and preferably includes a sodium salt or a potassium salt.

The term "substituted" in the mono-substituted amino group, the di-substituted amino group, the amide group, the N-substituted amide group, the N,N-disubstituted amide group, the substituted phenyl group, and the like of the "substituents" described above means that these groups preferably have the "substituents" described above.

The heterocycle and the heterocycle in the heterocyclic carbonyl group of the "substituents" have the same meanings as the "heterocycle" described above.

Preferred examples of the heterocyclic carbonyl group include morpholylcarbonyl, piperazylcarbonyl, piperidylcarbonyl, and the like, preferably morpholyl-4-yl-carbonyl, piperazin-4-yl carbonyl, (4-hydroxypiperazin)-1-yl carbonyl, and the like.

Metallo-β-lactamase Inhibitor Comprising the Compound Represented by the General Formula (I)

According to one aspect of the present invention, a metallo-β-lactamase inhibitor comprising the compound represented by the general formula (I), or a salt thereof or a solvate thereof is provided.

The compound represented by the general formula (I) has a metallo-β-lactamase inhibitory effect, and the compound as such can be used as a metallo-β-lactamase inhibitor.

As described above, the metallo-β-lactamase hydrolyzes many β-lactam antibiotics and inactivates the effectiveness. Hence, the activities of the β-lactam antibiotics can be recovered by combining the compound represented by the general formula (I) with the antibiotics.

The compound represented by the general formula (I) can be used as such as the metallo-β-lactamase inhibitor, or can be preferably used as a pharmaceutical composition described below in a combination with carrier and furthermore with the β-lactam antibiotics.

The term "$C_{2-6}$ alkyl group" represented by $R^1$ may be either a linear or branched chain, preferably a $C_{2-4}$ alkyl group, such as an ethyl group, a n-propyl group, an i-propyl group, a n-butyl group, an i-butyl group, a s-butyl group, a t-butyl group, a n-pentyl group, a neopentyl group, an i-pentyl group, a t-pentyl group, a n-hexyl group, an i-hexyl group, and the like, more preferably, an ethyl group, a n-propyl group, an i-propyl group, a n-butyl group, an i-butyl group, as-butyl group, and a t-butyl group. The alkyl group may be substituted, and the substituent includes the "substituents" described above, and more preferably, a hydroxyl group, a thiol group, an amino group, and a halogen atom.

The term "$C_{1-6}$ alkyl group" represented by $R^2$ may be either a linear or branched chain, preferably a $C_{1-4}$ alkyl group, such as a methyl group, an ethyl group, a n-propyl group, an i-propyl group, a n-butyl group, an i-butyl group, a s-butyl group, a t-butyl group, a n-pentyl group, a neopentyl group, an i-pentyl group, a t-pentyl group, a n-hexyl group, an i-hexyl group, and the like, more preferably, a methyl group, an ethyl group, a n-propyl group, an i-propyl group, a n-butyl group, an i-butyl group, a s-butyl group, and a t-butyl group. These alkyl groups may be substituted, and the substituent includes the "substituents" described above, and more preferably a thiol group, an amino group, and a halogen atom.

The term "$C_{3-7}$ cycloalkyl group" represented by $R^1$ or $R^2$ preferably includes a cyclopropyl group, a cyclobutyl group, a cyclopentyl group, a cyclohexyl group, a cycloheptyl group, and the like, more preferably a cyclopentyl group, a cyclohexyl group, and a cycloheptyl group. The $C_{3-7}$ cycloalkyl group may be substituted, and the substituent includes the "substituent" described above, and more preferably a hydroxyl group, a thiol group, a $C_{1-6}$ alkyl group, an amino group, and a halogen atom. In addition, the $C_{3-7}$ cycloalkyl group may be fused with the other rings such as aryl, preferably phenyl.

The —$C_{1-3}$ alkylene-phenyl group represented by $R^1$ or $R^2$ includes a benzyl group, a phenethyl group, a phenylpropyl group, and the like. The phenyl group of the —$C_{1-3}$ alkylene-phenyl group may be substituted, and the substituent includes the "substituent" described above, and more preferably a hydroxyl group; a $C_{1-6}$ alkyl group; —COOM, wherein M represents a hydrogen atom or a pharmaceutically acceptable cation; —CO—NR$^{22}$R$^{23}$, wherein R$^{22}$ and R$^{23}$, which may be the same or different, represents a hydrogen atom or a $C_{1-6}$ alkyl group, preferably a $C_{1-4}$ alkyl group, more preferably a $C_{1-2}$ alkyl group, wherein the alkyl group may be further substituted by an aminocarbonyl group, or R$^{22}$ and R$^{23}$, together with the nitrogen atom to which R$^{22}$ and R$^{23}$ are bonded, may form a five- or six-membered saturated heterocyclic ring comprising 1-2 oxygen or nitrogen atoms, preferably, a morphonyl group, a piperazyl group, or a piperidyl group, and the heterocycle, especially the piperidyl group may be substituted by a hydroxyl group or a $C_{1-6}$ alkanoyloxy group; —O—R$^{24}$ wherein R$^{24}$ represents a $C_{1-6}$ alkyl group, preferably $C_{1-4}$ alkyl group, wherein the alkyl group may be substituted, and the substituent includes —COOM, wherein M represents a hydrogen atom, a $C_{1-6}$ alkyl group or a pharmaceutically acceptable cation, an aminocarbonyl group, an amino group, a guanidino group, or a five- or six-membered unsaturated heterocycle having 1-2 nitrogen atoms, preferably, imidazole; a five- or six-membered saturated heterocycle having 1-2 nitrogen atoms, preferably pyrrolidine; and a hydroxymethyl group.

The term "—$C_{0-1}$ alkylene-heterocycle" represented by $R^1$ or $R^2$ means -bond-heterocycle or -methylene-heterocycle, and the "heterocycle" has the same meaning as described above and preferably includes a five- to ten-membered mono- or bi-cyclic heterocycle having 1-4 hetero atoms selected from nitrogen, oxygen, or sulfur atoms, more preferably a five- or six-membered saturated or unsaturated heterocycle having one nitrogen or oxygen atom. Specific examples of the "heterocycle" include tetrahydrofuran, furan, pyrrolidine, piperidine, pyrazolidine, imidazolidine, piperazine, morpholine, thiomorpholine, pyrrole, thiophene, oxazole, isoxazole, thiazole, isothiazole, imidazole, pyrazole, pyridine, pyridazine, pyrimidine, pyrazine, triazole, tetrazole, thiadiazole, azetidine, thiazoline, quinuclidine, triazine, isobenzofuran, indole, indolizine, chromene, quinoline, isoquinoline, cinnoline, quinazoline, quinoxaline, phthalazine, purine, pteridine, and the like. The bond or the methylene group may be bonded with any atoms on the heterocycle. One or more hydrogens on the heterocycle of the —$C_{0-1}$ alkylene-heterocycle may be substituted, and the substituent includes the "substituents" described above, more preferably a hydroxyl group, a thiol group, a $C_{1-6}$ alkyl group, an amino group, and a halogen atom.

The term "-O—$C_{1-6}$ alkyl group" represented by $R^1$ or $R^2$ means a linear, branched or cyclic $C_{1-6}$ alkoxy group, preferably a —O—$C_{1-4}$ alkyl group including methoxy, ethoxy, propoxy, isopropoxy, butoxy, isobutoxy, s-butoxy, t-butoxy, and the like, more preferably methoxy, ethoxy, propoxy, isopropoxy, t-butoxy, and the like. The portion of this alkyl group may be substituted, and the substituent includes the "substituents" described above, more preferably a hydroxyl group, a thiol group, a $C_{1-6}$ alkyl group, an amino group, a halogen atom, and a phenyl group.

The term "—S—$C_{1-6}$ alkyl group" represented by $R^1$ or $R^2$ means a linear, branched or cyclic $C_{1-6}$ alkylthio group, preferably a —S—$C_{1-4}$alkyl group including methylthio, ethylthio, propylthio, isopropylthio, butylthio, isobutylthio, s-butylthio, t-butylthio, and the like, more preferably methylthio, ethylthio, propylthio, isopropylthio, t-butylthio, and the like. The portion of this alkyl group may be substituted, and the substituent includes the "substituents" described above, more preferably a hydroxyl group, a thiol group, a $C_{1-6}$ alkyl group, an amino group, a halogen atom, and a phenyl group.

$M^1$ represents a hydrogen atom, a pharmaceutically acceptable cation, or a pharmaceutically acceptable group which may be hydrolyzed in vivo.

The term "pharmaceutically acceptable cation" represents a cation which may form a salt with one or both of the carboxyl groups of the general formula (I), and includes, for example, alkali metals, alkaline earth metals, ammonium, organic bases, and the like, preferably lithium, sodium, potassium, magnesium, calcium, ammonium, ethanolamine, triethanolamine, trimethylamine, triethylamine, diisopropylamine, and the like.

The term "pharmaceutically acceptable group which may be hydrolyzed in vivo" represents an eliminable group which is bonded to one or both of the carboxyl groups of the general formula (I), and represents a group which may be metabolized in vivo, hydrolyzed and removed to form a carboxyl group.

"The pharmaceutically acceptable group which may be hydrolyzed in vivo" in the compound represented by the general formula (I) is preferably an ester moiety, and includes those moieties usually used, for example, a lower alkyl group, a lower alkenyl group, a lower alkylcarbonyloxy lower alkyl group, a lower cycloalkylcarbonyloxy lower alkyl group, a lower cycloalkylmethylcarbonyloxy lower alkyl group, a lower alkenylcarbonyloxy lower alkyl group, an arylcarbonyloxy lower alkyl group, a tetrahydrofuranylcarbonyloxymethyl group, a lower alkoxy lower alkyl group, a lower alkoxy lower alkoxy lower alkyl group, an arylmethyloxy lower alkyl group, an arylmethyloxy lower alkoxy lower alkyl group, a lower alkoxycarbonyloxy lower alkyl group, a lower alkoxycarbonyloxy lower alkoxy group, a lower cycloalkoxycarbonyloxy lower alkyl group, a lower cycloalkylmethoxycarbonyloxy lower alkyl group, an aryloxycarbonyloxy lower alkyl group, a 3-phthalidyl group which may have substituents on the aromatic ring, a 2-(3-phthalidylidene)ethyl group which may have substituents on the aromatic ring, a 2-oxotetrahydrofuran-5-yl group, a mono-lower alkyl aminocarbonyloxymethyl group, a dilower alkyl aminocarbonyloxymethyl group, a 2-oxo-5-lower alkyl-1,3-dioxolen-4-yl methyl group, a piperidinyl carbonyloxy lower alkyl group which may be substituted, a lower alkyl lower cycloalkylaminocarbonyloxy lower alkyl group, and the like.

"The pharmaceutically acceptable group which may be hydrolyzed in vivo" preferably includes a methyl group, an ethyl group, a 1-(cyclohexyloxycarbonyloxy)ethyl group, an acetoxymethyl group, a 1-(isopropyloxycarbonyloxy)ethyl group, a 1-(ethoxycarbonyloxy)ethyl group, a pivaloyloxymethyl group, a cyclohexyloxycarbonyloxymethyl group, a 1-(isobutyloxycarbonyloxy)ethyl group, a 1-(cyclohexyloxycarbonyloxy)-2-methylpropan-1-yl group, an isobutyloxycarbonyloxymethyl group, an isopropyloxycarbonyloxymethyl group, an isobutyryloxymethyl group, a (pentan-1-yl)oxycarbonyloxymethyl group, a (butan-1-yl)oxycarbonyloxymethyl group, a (1-ethylpropan-1-yl)oxycarbonyloxymethyl group, an isopentyloxycarbonyloxymethyl group, a (propan-1-yl)oxymethyl group, an ethoxycarbonyloxymethyl group, a neopentyloxycarbonyloxymethyl group, a methoxycarbonyloxymethyl group, a cyclopentyloxycarbonyloxymethyl group, a t-butoxycarbonyloxymethyl group, a phthalidyl group, a 1-(methoxycarbonyloxy)ethyl group, a 1-(cyclopentyloxycarbonyloxy)ethyl group, a (tetrahydropyran-4-yl)oxycarbonyloxymethyl group, a 1-(neopentyloxycarbonyloxy)ethyl group, a (piperidin-1-yl)carbonyloxymethyl group, an allyl group, a 1-(t-butoxycarbonyloxy)ethyl group, an (N,N-di-n-propylamino)carbonyloxymethyl group, a phenyloxycarbonyloxymethyl group, a (5-methyl-2-oxo-1,3-dioxolen-4-yl)methyl group, a (cis-2,6-dimethylpiperidin-1-yl)carbonyloxymethyl group, an N,N-di-(butan-1-yl)aminocarbonyloxymethyl group, a hexane-1-yl group, an N-(hexane-1-yl)-N-methylaminocarbonyloxymethyl group, an N,N-diisobutylaminocarbonyloxymethyl group, an N,N-diisopropylaminocarbonyloxymethyl group, an N-cyclohexyl-N-methylaminocarbonyloxymethyl group, an N-pentan-1-yl aminocarbonyloxymethyl group, an N-cyclohexyl-N-ethylaminocarbonyloxymethyl group, an N-isobutyl-N-isopropylaminocarbonyloxymethyl group, an N-t-butyl-N-ethylaminocarbonyloxymethyl group, a 1-[(cis-2,6-dimethylpiperidin-1-yl)carbonyloxy]ethyl group, a 1-(N,N-diisopropylaminocarbonyloxy)ethyl group, N-ethyl-N-isoamylaminocarbonyloxymethyl group, and the like.

According to a preferred embodiment of the present invention, in the general formula (I), $R^1$ represents a $C_{2-6}$ alkyl group, a $C_{3-7}$ cycloalkyl group, a hydroxymethyl group, a benzyl group, a phenethyl group, a $-C_{0-1}$ alkylene-heterocycle, wherein heterocycle represents tetrahydropyran, pyridine, or piperidine, a $-O-C_{1-6}$ alkyl group, or a $-S-C_{1-6}$ alkyl group, all of which may be substituted, $R^2$ represents a $C_{1-6}$ alkyl group, a $C_{3-7}$ cycloalkyl group, a hydroxymethyl group, a benzyl group, a phenethyl group, a $-C_{0-1}$ alkylene-heterocycle, wherein heterocycle represents tetrahydropyran, pyridine, or piperidine, a $-O-C_{1-6}$ alkyl group, or a $-S-C_{1-6}$ alkyl group, all of which may be substituted, $M^1$, which may be the same or different, represents a hydrogen atom, a pharmaceutically acceptable cation, or a pharmaceutically acceptable group which may be hydrolyzed in vivo.

In this embodiment, the "substituent" has the same meaning as described above, and more preferably includes a hydroxyl group, a $C_{1-6}$ alkyl group, a $C_{1-6}$ alkoxy group, a carboxy group, an amide group, a phenyl group, which may be fused with the ring, a heterocyclic carbonyl group which may be substituted, e.g. a piperidinecarbonyl group, an acyloxypiperidinecarbonyl group, a hydroxypiperidinecarbonyl group, a piperazinecarbonyl group, a morpholinecarbonyl group, and the like, a heterocycle-$C_{1-6}$ alkoxy group such as an imidazolyl $C_{1-6}$ alkoxy group, a heterocycloxy group such as a pyrrolidineoxy group, an aminoxo $C_{1-6}$ alkylcarbamoyl group, a carboxyl group, an amino $C_{1-6}$ alkoxy group, a guanidyl group, a guanidyl $C_{1-6}$ alkyl group, a guanidyl $C_{1-6}$ alkoxy group, a $C_{1-6}$ alkoxyoxo $C_{1-6}$ alkoxy group, and the like.

$M^1$ may be the same or different, and represents a hydrogen atom, a pharmaceutically acceptable cation, or a pharmaceutically acceptable group which may be hydrolyzed in vivo.

"The pharmaceutically acceptable cation" preferably includes lithium, sodium, potassium, magnesium, calcium, ammonium, ethanolamine, triethanolamine, trimethylamine, triethylamine, diisopropylamine, and the like.

"The pharmaceutically acceptable group which may be hydrolyzed in vivo" represents an eliminable group which is bonded to one or both of the carboxyl groups of the general formula (I), and represents a group which may be metabolized in vivo, hydrolyzed and removed to form a carboxyl group.

"The pharmaceutically acceptable group which may be hydrolyzed in vivo" in the compound represented by the general formula (I) is preferably a methyl group, an ethyl group, a 1-(cyclohexyloxycarbonyloxy)ethyl group, an acetoxymethyl group, a 1-(isopropyloxycarbonyloxy)ethyl group, a 1-(ethoxycarbonyloxy)ethyl group, a pivaloyloxymethyl group, a cyclohexyloxycarbonyloxymethyl group, a 1-(isobutyloxycarbonyloxy)ethyl group, a 1-(cyclohexyloxycarbonyloxy)-2-methylpropan-1-yl group, an isobutyloxycarbonyloxymethyl group, an isopropyloxycarbonyloxymethyl group, an isobutyryloxymethyl group, a (pentan-1-yl)oxycarbonyloxymethyl group, a (butan-1-yl)oxycarbonyloxymethyl group, a (1-ethylpropan-1-yl)oxycarbonyloxymethyl group, an isopentyloxycarbonyloxymethyl group, a (propan-1-yl)oxymethyl group, an ethoxycarbonyloxymethyl group, a neopentyloxycarbonyloxymethyl group, a methoxycarbonyloxymethyl group, a cyclopentyloxycarbonyloxymethyl group, a t-butoxycarbonyloxymethyl group, a phthalidyl group, a 1-(methoxycarbonyloxy)ethyl group, a 1-(cyclopentyloxycarbonyloxy)ethyl group, a (tetrahydropyran-4-yl)oxycarbonyloxymethyl group, a 1-(neopentyloxycarbonyloxy)ethyl group, a (piperidin-1-yl)carbonyloxymethyl group, an allyl group, a 1-(t-butoxycarbonyloxy)ethyl group, an (N,N-di-n-propylamino)carbonyloxymethyl group, a phenyloxycarbonyloxymethyl group, a (5-methyl-2-oxo-1,3-dioxolen-4-yl)methyl group, a (cis-2,6-dimethylpiperidin-1-yl)carbonyloxymethyl group, an N,N-di-(butan-1-yl)aminocarbonyloxymethyl group, an hexane-1-yl group, an N-(hexane-1-yl)-N-methylaminocarbonyloxymethyl group, an N,N-diisobutylaminocarbonyloxymethyl group, an N,N-diisopropylaminocarbonyloxymethyl group, an N-cyclohexyl-N-methylaminocarbonyloxymethyl group, an N-pentan-1-yl aminocarbonyloxymethyl group, an N-cyclohexyl-N-ethylaminocarbonyloxymethyl group, an N-isobutyl-N-isopropylaminocarbonyloxymethyl group, an N-t-butyl-N-ethylaminocarbonyloxymethyl group, a 1-[(cis-2,6-dimethylpiperidin-1-yl)carbonyloxy]ethyl group, a 1-(N,N-diisopropylaminocarbonyloxy)ethyl group, an N-ethyl-N-isoamylaminocarbonyloxymethyl group, and the like.

The preferred group of the compounds of the present invention includes the group of the compounds, in which
$R^1$ represents
a $C_{2-6}$ alkyl group;
a $C_{3-7}$ cycloalkyl group, which may be substituted by a hydroxyl group and may be fused with aryl, preferably phenyl;
a hydroxymethyl group;
a $-C_{1-3}$ alkylene-phenyl group, in which the phenyl group may be substituted and the substituent includes a hydroxyl group, a $C_{1-6}$ alkyl group, a hydroxymethyl group, $-COOM$, wherein M represents a hydrogen atom or a pharmaceutically acceptable cation, $-CO-NR^{22}R^{23}$, wherein $R^{22}$ and $R^{23}$, which may be the same or different, represent a hydrogen atom or a $C_{1-6}$ alkyl group, preferably a $C_{1-4}$ alkyl group, more preferably a $C_{1-2}$ alkyl group, wherein the alkyl group may be further substituted by an aminocarbonyl group, or $R^{22}$ and $R^{23}$, together with the nitrogen atom to which $R^{22}$ and $R^{23}$ are bonded, may form a five- or six-membered saturated heterocyclic ring comprising 1-2 oxygen or nitrogen atoms, preferably, a morphonyl group, a piperazyl group, or a piperidyl group, and the heterocycle, especially the piperidyl group may be substituted by a hydroxyl group or a $C_{1-6}$ alkanoyloxy group, a group —O—$R^{24}$ wherein $R^{24}$ represents a $C_{1-6}$ alkyl group, preferably a $C_{1-4}$ alkyl group, wherein the alkyl group may be substituted, and the substituent includes —COOM, wherein M represents a hydrogen atom, a $C_{1-6}$ alkyl group or a pharmaceutically acceptable cation, an aminocarbonyl group, an amino group, a guanidino group, or a five- or six-membered unsaturated heterocycle having 1-2 nitrogen atoms, preferably, imidazole, a five- or six-membered saturated heterocycle having 1-2 nitrogen atoms, preferably pyrrolidine;

a —$C_{0-1}$ alkylene-heterocycle, in which the heterocycle represents five- or six-membered saturated or unsaturated heterocycle comprising one nitrogen or oxygen atom, and may be substituted by a hydroxyl group;

a —O—$C_{1-6}$ alkyl group; or a —S—$C_{1-6}$ alkyl group, and $R^2$ represents a $C_{1-6}$ alkyl group;

a $C_{3-7}$ cycloalkyl group, in which the ring may be substituted by a hydroxyl group and fused with aryl, preferably phenyl;

a hydroxymethyl group;

a —$C_{1-3}$ alkylene-phenyl group, in which the phenyl group may be substituted and the substituent includes a hydroxyl group, a $C_{1-6}$ alkyl group, a hydroxymethyl group, —COOM, wherein M represents a hydrogen atom or a pharmaceutically acceptable cation, —CO—NR$^{22}$R$^{23}$, wherein R$^{22}$ and R$^{23}$, which may be the same or different, represent a hydrogen atom or a $C_{1-6}$ alkyl group, preferably a $C_{1-4}$ alkyl group, more preferably a $C_{1-2}$ alkyl group, wherein the alkyl group may be further substituted by an aminocarbonyl group, or R$^{22}$ and R$^{23}$, together with the nitrogen atom to which R$^{22}$ and R$^{23}$ are bonded, may form a five- or six-membered saturated heterocyclic ring comprising 1-2 oxygen or nitrogen atoms, preferably, a morphonyl group, a piperazyl group, or a piperidyl group, and the heterocycle, especially the piperidyl group may be substituted by a hydroxyl group or a $C_{1-6}$ alkanoyloxy group, a group —O—$R^{24}$ wherein $R^{24}$ represents a $C_{1-6}$ alkyl group, preferably a $C_{1-4}$ alkyl group, wherein the alkyl group may be substituted, and the substituent includes —COOM, wherein M represents a hydrogen atom, a $C_{1-6}$ alkyl group or a pharmaceutically acceptable cation, an aminocarbonyl group, an amino group, a guanidino group, or a five- or six-membered unsaturated heterocycle having 1-2 nitrogen atoms, preferably, imidazole, a five- or six-membered saturated heterocycle having 1-2 nitrogen atoms, preferably pyrrolidine;

a —$C_{0-1}$ alkylene-heterocycle, in which the heterocycle represents five- or six-membered saturated or unsaturated heterocycle comprising one nitrogen or oxygen atom, and may be substituted by a hydroxyl group;

a —O—$C_{1-6}$ alkyl group; or a —S—$C_{1-6}$ alkyl group.

The more preferred group of the compounds of the formula (I) includes the group of the compounds, in which $R^1$ represents a $C_{2-6}$ alkyl group, a $C_{3-7}$ cycloalkyl group, which may be substituted by a hydroxyl group and may be fused with aryl, preferably phenyl;

a hydroxymethyl group;

a —$C_{1-3}$ alkylene-phenyl group, in which the phenyl group may be substituted by a hydroxyl group, a $C_{1-6}$ alkyl group, a hydroxymethyl group, —COOM, wherein M represents a hydrogen atom or a pharmaceutically acceptable cation, —CO—NR$^{22}$R$^{23}$, wherein R$^{22}$ and R$^{23}$, which may be the same or different, represent a hydrogen atom or a $C_{1-6}$ alkyl group, preferably a $C_{1-4}$ alkyl group, more preferably a $C_{1-2}$ alkyl group, wherein the alkyl group may be further substituted by an aminocarbonyl group, or R$^{22}$ and R$^{23}$, together with the nitrogen atom to which R$^{22}$ and R$^{23}$ are bonded, may form a five- or six-membered saturated heterocyclic ring comprising 1-2 oxygen or nitrogen atoms, preferably, a morphonyl group, a piperazyl group, or a piperidyl group, and the heterocycle, especially the piperidyl group may be substituted by a hydroxyl group or a $C_{1-6}$ alkanoyloxy group, a group —O—$R^{24}$ wherein $R^{24}$ represents a $C_{1-6}$ alkyl group, preferably a $C_{1-4}$ alkyl group, wherein the alkyl group may be substituted, and the substituent includes —COOM, wherein M represents a hydrogen atom, a $C_{1-6}$ alkyl group or a pharmaceutically acceptable cation, an aminocarbonyl group, an amino group, a guanidino group, or a five- or six-membered unsaturated heterocycle having 1-2 nitrogen atoms, preferably, imidazole, a five- or six-membered saturated heterocycle having 1-2 nitrogen atoms, preferably pyrrolidine;

a —$C_{0-1}$ alkylene-heterocycle, in which the heterocycle represents five- or six-membered saturated or unsaturated heterocycle comprising one nitrogen or oxygen atom, and may be substituted by a hydroxyl group;

a —O—$C_{1-6}$ alkyl group; or a —S—$C_{1-6}$ alkyl group, and $R^2$ represents a $C_{1-6}$ alkyl group;

a $C_{3-7}$ cycloalkyl group, in which the ring may be substituted by a hydroxyl group and fused with aryl, preferably phenyl; or a —$C_{1-2}$ alkylene-phenyl group.

The more preferred group of the compounds includes the group of the compounds, in which $R^1$ represents a $C_{2-6}$ alkyl group;

a $C_{3-7}$ cycloalkyl group, in which the ring may be substituted by a hydroxyl group and fused with a phenyl group;

a hydroxymethyl group;

a $C_{1-2}$ alkylene-phenyl group, in which the phenyl group may be substituted by a hydroxyl group, a $C_{1-6}$ alkyl group, a hydroxymethyl group, —COOM, wherein M represents a hydrogen atom or a pharmaceutically acceptable cation, —CO—NR$^{22}$R$^{23}$, wherein R$^{22}$ and R$^{23}$, which may be the same or different, represent a hydrogen atom or a $C_{1-6}$ alkyl group, preferably a $C_{1-4}$ alkyl group, more preferably a $C_{1-2}$ alkyl group, wherein the alkyl group may be further substituted by an aminocarbonyl group, or R$^{22}$ and R$^{23}$, together with the nitrogen atom to which R$^{22}$ and R$^{23}$ are bonded, form a five- or six-membered saturated heterocycle comprising 1-2 oxygen atoms or nitrogen atoms, preferably a morphonyl group, a piperazyl group, or a piperidyl group, wherein the heterocycle, especially a piperidyl group may be substituted by a hydroxyl group or a $C_{1-6}$ alkanoyloxy group, a group —O—$R^{24}$, wherein $R^{24}$ may be substituted by a $C_{1-6}$ alkyl group, preferably a $C_{1-4}$ alkyl group, which may be substituted by such substituents as —COOM, wherein M represents a hydrogen atom, a $C_{1-6}$ alkyl group or a pharmaceutically acceptable cation, an aminocarbonyl group, an amino group, a guanidino group, or a five- or six-membered unsaturated heterocycle comprising 1-2 nitrogen atoms, preferably imidazole, or a five- or six-membered saturated heterocycle comprising 1-2 nitrogen atoms, preferably pyrrolidine;

a —$C_{0-1}$ alkylene-heterocycle, in which the heterocycle represents pyridine, morpholine, piperidine, or tetrahydropyran, and may be substituted by a hydroxyl group;

a —O—$C_{1-6}$ alkyl group, or
a —S—$C_{1-6}$ alkyl group,
$R^2$ represents
a $C_{1-6}$ alkyl group, or
a $C_{3-7}$ cycloalkyl group.

The more preferred group of the compounds includes the group of the compounds, in which
$R^1$ represents
a $C_{2-4}$ alkyl group; or
a $C_{3-7}$ cycloalkyl group, which may be substituted by a hydroxyl group, and fused with a phenyl group;
$R^2$ represents
a $C_{1-4}$ alkyl group; or
a $C_{3-7}$ cycloalkyl group.

The preferred examples of $R^1$ or $R^2$ preferably include an ethyl group, a n-propyl group, an i-propyl group, a cyclopentyl group, a 2,3-dihydro-1H-inden-2-yl group, a cyclohexyl group, a 2-(trans-4-hydroxycyclohexyl) group, a 2-(cis-4-hydroxycyclohexyl) group, a 2-(tetrahydropyran-4-yl) group, a 2-[(piperidin-1-yl)methyl] group, a (pyridine-3-yl)methyl group, a (4-hydroxypiperidin-1-yl)methyl, a hydroxymethyl group, a (2-methylphenyl)methyl group, a methoxy group, a methylthio group, an isopropylthio group, a benzyl group, a 2-(4-hydroxybenzyl) group, a 4-methoxybenzyl group, a 4-carboxybenzyl group, a 4-carbamoylbenzyl group, a 4-(4-acetoxypiperidin-1-carbonyl)benzyl group, a 4-(4-hydroxypiperidin-1-carbonyl)benzyl group, a 4-(2-amino-2-oxoethylcarbamoyl)benzyl group, a 4-hydroxybenzyl group, a 4-oxidobenzyl group (sodium salt), a 4-(carboxylatomethoxy)benzyl group, a 4-(2-methoxy-2-oxoethoxy)benzyl group, a 4-(2-amino-2-oxoethoxy)benzyl group, a 4-(2-amino-2-oxoethoxy)benzyl group, a 4-(2-aminoethoxy)benzyl group, a 4-(morpholine-1-carbonyl)benzyl group, a 4-(piperazine-1-carbonyl)benzyl group, a 4-[2-(1H-imidazol-1-yl)ethoxy]benzyl group, a 4-(2-guanidinoethoxy)benzyl group, a 4-(pyrrolidine-3-yloxy)benzyl group, a phenethyl group, and the like, provided that $R^1$ does not represent a methyl group.

In the general formula (I), the more preferred group of the compounds includes the group of the compounds, in which $R^1$ represents an ethyl group, a n-propyl group, an i-propyl group, a cyclopentyl group, a 2,3-dihydro-1H-inden-2-yl group, a cyclohexyl group, a 2-(trans-4-hydroxycyclohexyl) group, a 2-(cis-4-hydroxycyclohexyl) group, a 2-(tetrahydropyran-4-yl) group, a 2-[(piperidin-1-yl)methyl] group, a (4-hydroxypiperidin-1-yl)methyl group, a hydroxymethyl group, a methoxy group, a methylthio group, an isopropylthio group, a benzyl group, a 2-(4-hydroxybenzyl) group, a 4-carboxybenzyl group, a 4-carbamoylbenzyl group, a 4-(4-acetoxypiperidin-1-carbonyl)benzyl group, a 4-(4-hydroxypiperidin-1-carbonyl)benzyl group, a 4-(2-amino-2-oxoethylcarbamoyl)benzyl group, a 4-hydroxybenzyl group, a 4-oxidobenzyl group (sodium salt), a 4-(carboxylatomethoxy)benzyl group, a 4-(2-amino-2-oxoethoxy)benzyl group, a 4-(2-amino-2-oxoethoxy)benzyl group, a 4-(2-aminoethoxy)benzyl group, a 4-[2-(1H-imidazol-1-yl)ethoxy]benzyl group, a 4-(2-guanidinoethoxy)benzyl group, a phenethyl group, or the like, $R^2$ represents a methyl group, an ethyl group, a n-propyl group, an i-propyl group, a cyclopentyl group, a benzyl group, a phenethyl group, a (2-methylphenyl)methyl group, a (pyridine-3-yl)methyl group, a 4-(morpholine-1-carbonyl)benzyl group, a 4-(piperazine-1-carbonyl)benzyl group, a 4-methoxybenzyl group, a 4-(2-methoxy-2-oxoethoxy)benzyl group, a 4-(pyrrolidine-3-yloxy)benzyl group, or the like.

Furthermore, specific examples of the compounds represented by the general formula (I) include:

2-ethyl-3-methylmaleic acid dimethyl ester,
2-ethyl-3-methylmaleic acid disodium
2,3-diethylmaleic acid diethyl ester,
2,3-diethylmaleic acid disodium,
2,3-diethylmaleic acid dipotassium,
2,3-di-n-propylmaleic acid diethyl ester,
2,3-di-n-propylmaleic acid disodium,
2-benzyl-3-methylmaleic acid dimethyl ester,
2-benzyl-3-methylmaleic acid disodium,
2-benzyl-3-ethylmaleic acid disodium,
3-ethyl-2-(4-hydroxybenzyl)maleic acid disodium,
2,3-dibenzylmaleic acid disodium,
2-benzyl-3-phenethylmaleic acid disodium,
2,3-diphenethylmaleic acid diethyl ester,
2,3-diphenethylmaleic acid disodium,
2-isopropyl-3-methylmaleic acid disodium,
3-ethyl-2-isopropylmaleic acid disodium,
2,3-diisopropylmaleic acid disodium,
3-benzyl-2-isopropylmaleic acid disodium,
2-isopropyl-3-(2-methylphenyl)methylmaleic acid disodium,
2-cyclopentyl-3-ethylmaleic acid disodium,
2-cyclopentyl-3-isopropylmaleic acid disodium,
3-benzyl-2-cyclopentylmaleic acid disodium,
2,3-dicyclopentylmaleic acid disodium,
2-(2,3-dihydro-1H-inden-2-yl)-3-isopropylmaleic acid disodium,
2-cyclohexyl-3-isopropylmaleic acid disodium,
2-(trans-4-hydroxycyclohexyl)-3-isopropylmaleic acid disodium,
2-(cis-4-hydroxycyclohexyl)-3-isopropylmaleic acid disodium,
3-isopropyl-2-(tetrahydropyran-4-yl)maleic acid disodium,
2-isopropyl-3-[(pyridine-3-yl)methyl]maleic acid disodium,
3-methyl-2-[(piperidin-1-yl)methyl]maleic acid dimethyl ester,
3-methyl-2-[(piperidin-1-yl)methyl]maleic acid disodium,
2-[(4-hydroxypiperidin-1-yl)methyl]-3-methylmaleic acid dimethyl ester,
2-[(4-hydroxypiperidin-1-yl)methyl]-3-methylmaleic acid disodium,
2-hydroxymethyl-3-methylmaleic acid disodium,
3-ethyl-2-methoxymaleic acid disodium,
3-ethyl-2-methylthiomaleic acid disodium
3-ethyl-2-isopropylthiomaleic acid disodium,
2-(4-carboxybenzyl)-3-isopropylmaleic acid dimethyl ester,
2-(4-carboxybenzyl)-3-isopropylmaleic acid trisodium,
2-(4-carbamoylbenzyl)-3-isopropylmaleic acid dimethyl ester,
2-(4-carbamoylbenzyl)-3-isopropylmaleic acid disodium,
2-isopropyl-3-[4-(morpholine-1-carbonyl)benzyl]maleic acid dimethyl ester,
2-isopropyl-3-[4-(morpholine-1-carbonyl)benzyl]maleic acid disodium,
2-isopropyl-3-[4-(piperazine-1-carbonyl)benzyl]maleic acid dimethyl ester hydrochloride,
2-isopropyl-3-[4-(piperazine-1-carbonyl)benzyl]maleic acid disodium,
2-[4-(4-acetoxypiperidin-1-carbonyl)benzyl]-3-isopropylmaleic acid dimethyl ester,
2-[4-(4-hydroxypiperidin-1-carbonyl)benzyl]-3-isopropylmaleic acid disodium,
2-[4-(2-amino-2-oxoethylcarbamoyl)benzyl]-3-isopropylmaleic acid dimethyl ester,
2-[4-(2-amino-2-oxoethylcarbamoyl)benzyl]-3-isopropylmaleic acid disodium,
2-isopropyl-3-(4-methoxybenzyl)maleic acid disodium, 2-(4-hydroxybenzyl)-3-isopropylmaleic acid dimethyl ester,
2-(4-oxidobenzyl)-3-isopropylmaleic acid trisodium,
2-isopropyl-3-[4-(2-methoxy-2-oxoethoxy)benzyl]maleic acid dimethyl ester,
2-[4-(carboxylatomethoxy)benzyl]-3-isopropylmaleic acid trisodium,
2-[4-(2-amino-2-oxoethoxy)benzyl]-3-isopropylmaleic acid dimethyl ester,
2-[4-(2-amino-2-oxoethoxy)benzyl]-3-isopropylmaleic acid disodium,
2-[4-(2-aminoethoxy)benzyl]-3-isopropylmaleic acid dimethyl ester,
2-[4-(2-aminoethoxy)benzyl]-3-isopropylmaleic acid disodium,
2-{4-[2-(1H-imidazol-1-yl)ethoxy]benzyl}-3-isopropylmaleic acid dimethyl ester,
2-{4-[2-(1H-imidazol-1-yl)ethoxy]benzyl}-3-isopropylmaleic acid disodium,
2-isopropyl-3-[4-(pyrrolidine-3-yloxy)benzyl]maleic acid dimethyl ester,
2-isopropyl-3-[4-(pyrrolidine-3-yloxy)benzyl]maleic acid disodium,
2-[4-(2-guanidinoethoxy)benzyl]-3-isopropylmaleic acid dimethyl ester hydrochloride, and
2-[4-(2-guanidinoethoxy)benzyl]-3-isopropylmaleic acid disodium.

The compound of the general formula (I) is preferably a pharmaceutically acceptable salt, which includes an acid addition salt. Thus, the compound of the general formula (I) can be used in the form of a salt derived from mineral acids or organic salts, which include an acetic acid salt, an adipic acid salt, an alginic acid salt, an aspartic acid salt, a benzoic acid salt, a benzenesulfonic acid salt, a hydrogensulfate salt, a butyric acid salt, a citric acid salt, a camphoric acid salt, a camphorsulfonic acid salt, a cyclopentanpropionic acid salt, a digluconic acid salt, a dodecylsulfuric acid salt, an ethanesulfonic acid salt, a fumaric acid salt, a glucoheptanoic acid salt, a glycerophosphoric acid salt, a hemisulfuric acid salt, a heptanoic acid salt, a hexanoic acid salt, a hydrochloride salt, a hydrobromic acid salt, a hydroiodic acid salt, a 2-hydroxyethanesulfonic acid salt, a lactic acid salt, a maleic acid salt, a methanesulfonic acid salt, a 2-naphthalenesulfonic acid salt, a nicotinic acid salt, an oxalic acid salt, a pamoic acid salt, a pectic acid salt, a persulfuric acid salt, a 3-phenylpropionic acid salt, a picric acid salt, a pivalic acid salt, a propionic acid salt, a succinic acid salt, a tartaric acid salt, a thiocyanic acid salt, a tosylic acid salt, and an undecanoic acid salt.

The compound of the general formula (I) may be in the form of a solvate.

The solvent of the solvate includes water, methanol, ethanol, isopropanol, butanol, acetone, ethyl acetate, chloroform, and the like.

The compound of the general formula (I) or a salt thereof may contain asymmetric carbons in the molecule, and each of the isomers or all of the mixtures of the isomers are included in the present invention. Also, the compound of the general formula (I) may be used in the form of a prodrug. The prodrugs can be hydrolyzed in vivo and thus preferably used for oral administration because of its good absorption from gastric mucosa or intestinal mucosa, resistance against acid, and the other factors.

Pharmaceutical Uses and Pharmaceutical Compositions

The compound of the general formula (I) has, as described above, metallo-β-lactamase inhibitory effect and thus used for the inhibition of metallo-β-lactamase. As one of the specific embodiments of its applications, the compound of the present invention can be used in combination with antibiotics which will be inactivated by the action of metallo-β-lactamase, among others β-lactam antibiotics to recover the activities of these antibiotics for the therapy of infections.

Therefore, according to one embodiment of the present invention, a metallo-β-lactamase inhibitor and pharmaceutical composition comprising the compound of the general formula (I) as an effective ingredient which is used in combination with β-lactam antibiotics is provided. That is, the metallo-β-lactamase inhibitor and pharmaceutical composition according to the present invention is administered concomitantly or sequentially with β-lactam antibiotics.

The β-lactam antibiotics include carbapenems, penicillins, cephems, or prodrugs thereof.

Specific examples of the carbapenems include imipenem, meropenem, biapenem, doripenem, ertapenem, tebipenem (pivaloyloxymethyl(4R,5S,6S)-6-[(R)-1-hydroxyethyl]-4-methyl-7-oxo-3-{[1-(1,3-thiazoline-2-yl)azetidine-3-yl]thio})-1-azabicyclo[3.2.0]hept-2-ene-2-carboxylate), CS-023 ((−)-(4R,5S,6S)-3-[[(3S,5S)-5-[(S)-3-(2-guanidinoacetylamino) pyrrolidin-1-ylcarbonyl]-1-methylpyrrolidin-3-yl]thio]-6-[(R)-1-hydroxyethyl]-4-methyl-7-oxo-azabicyclo[3.2.0]hept-2-ene-2-carboxylic acid) and ME1036 ((1S,5R,6S)-2-[7-(1-carbamoylmethylpyridinium-3-yl)carbonylimidazo[5,1-b]thiazol-2-yl]-6-((1R)-1-hydroxyethyl)-1-methyl-1-carbapen-2-em-3-carboxylate), and the like. Particularly, the carbapenem which is preferably used in combination with the compound of the general formula (I) is imipenem, meropenem, biapenem and doripenem.

Examples of the penicillins include benzylpenicillin, phenoxymethylpenicillin, carbenicillin, azidocillin, propicillin, ampicillin, amoxicillin, epicillin, ticarcillin, ciclacillin, pirbenicillin, azlocillin, meziocillin, sulbenicillin, piperacillin, and the other well known penicillins. These penicillins can be used in the form of their prodrugs, for example, as in vivo hydrolyzable esters such as acetoxymethyl, pivaloyloxymethyl, 1-(ethoxycarbonyloxy)ethyl and phthalidyl esters of ampicillin, benzylpenicillins and amoxicillin, as aldehyde or ketone addition products of penicillins having a 6-β-aminoacetamide side chain including, for example, similar derivatives of hetacillin, metampicillin and amoxicillin, and further as esters such as phenyl or indanyl esters of penicillins having a 6-α-carboxyacetamide side chain such as carbenicillin and ticarcillin. Particularly preferred penicillins used in combination with the compound of the general formula (I) ampicillin, amoxicillin, carbenicillin, piperacillin, azlocillin, mezlocillin and ticarcillin. These penicillins can be used in the form of a pharmaceutically acceptable salt thereof such as a sodium salt. As another form, ampicillin or amoxicillin can be used in the form of a suspension for injection or of amphoteric granules for a suspension for injection (ampicillin trihydrate or amoxicillin trihydrate) in combination with the compound of the general formula (I).

Cephems include, for example, cefatrizine, cefaloridine, cefalotin, cefazolin, cephalexin, cephacetrile, cefapilin, cefamandole naphate, cefradine, 4-hydroxycephalexin, cefoperazone, latamoxef, cefminox, flomoxef, cefsulodin, ceftadizime, cefuroxime, cefditoren, cefmetazole, cefotaxime, ceftriaxone, cefepime, cefpirome, cefozopran, as well as the other well know cephems, and these cephems can also be used in the form of their prodrugs. Particularly preferred cephems used in combination with the compound of the general formula (I) are cefotaxime, ceftriaxone, ceftadizime and cefepime, which can be used in the form of a pharmaceutically acceptable salt such as a sodium salt.

According to the preferred embodiment of the present invention, it is also preferred to combine the compound of the general formula (I) and carbapenem antibiotics in the presence of a dehydropeptidase (DHP) inhibitor, because many carbapenems are liable to be hydrolyzed by DHP. The preferred DHP inhibitor includes cilastatin or a salt thereof.

According to the preferred embodiment of the present invention, it is preferred to combine further the other serine-β-lactamase inhibitor in addition to the compound of the general formula (I), and the preferred examples of the other serine-β-lactamase inhibitor include clavulanic acid, sulbactam or tazobactam.

The metallo-β-lactamase producing strain which is preferably used in combination with the antibiotics and the compound of the general formula (I) includes, for example, *Bacillus cereus, Bacteroides fragilis, Escherichia coli, Aeromonas hydrophila, Klebsiella pneumoniae, Pseudomonas aeruginosa, Serratia marcescens, Stenotrophomonas maltophilia, Shigella flexneri, Alcaligenes xylosoxidans, Legionella gormanii, Chryseobacterium meningosepticum, Chryseobacterium indologenes, Acinetobacter baumannii, Citrobacter freundii and Enterobacter cloacae*, and the like.

The doses of the compound of the general formula (I) and the antibiotic can be varied over a wide range, for example, generally in a proportion of 1:0.5-20 by weight, preferably 1:1-8.

The compound of the general formula (I) and the β-lactam antibiotic may also be administered individually or in the form of a unit composition containing the both effective ingredients. In any of the embodiments, the compound of the general formula (I) and/or the antibiotic are preferably combined with a pharmaceutically acceptable carrier, i.e. an additive for a preparation, to form a pharmaceutical composition.

The pharmaceutical composition according to the present invention may be administered orally or parenterally. It is possible to envisage parenteral administration routes including intranasal, intraocular, intra-aural, transdermal, intratracheal, intrarectal, intraurinary, subcutaneous, intramuscular and intravenous routes. Examples of the preparation suitable for oral administration include, for example, tablets, particles, granules, powders, syrups, solutions, capsules, chewables, or suspensions. Examples of the preparation suitable for parenteral administration include, for example, injections, droplets, inhalants, nebulae, suppositories, vaginal suppositories, percutaneous absorbent, transmucosal absorbent, eye drops, ear drops, nose drops, or patches. Liquid preparations such as injections or drops may be provided, for example, as a pharmaceutical composition in the form of lyophilized powder, which may be dissolved or suspended into water or the other appropriate solvents such as physiological saline, or glucose infusion at the time of use.

Carriers, i.e. additives for preparations can be appropriately selected according as the forms of the pharmaceutical composition, and include, but are not limited to, stabilizers, surfactants, plasticizers, lubricants, solubilizing agents, buffering agents, sweetenings, bases, adsorbents, flavoring agents, binding agents, suspending agents, brightening agents, coating agents, aromatizing agents, perfumes, humectants, humidity modifiers, fillers, anti-foaming agents, masticatories, refrigerants, colorants, sugar-coating agents, isotonicity agents, pH modifiers, softeners, emulsifiers, adhesives, adhesion intensifiers, viscous agents, thickeners, foaming agents, excipients, dispersants, propellants, disintegrating agents, disintegration accelerators, fragrances, anti-humectants, aseptics, preservatives, analgesics, solvents, liquefacients, dissolution accelerators, fluidizing agents, and the like, and two or more of these additives may be combined.

Specific examples of these additives for preparations are described, for example, in "The Dictionary of Pharmaceutical Additives" (Ed. by Japan Pharmaceutical Excipients Council, Yakuji Nippo Limited), a person skilled in the art can select an appropriate additive for preparation according to the form of a pharmaceutical composition to prepare the desired form of the pharmaceutical composition according to the process widely used in the field. Generally, the pharmaceutical composition can be prepared so that the substance as the effective ingredient is in the range of 1.0-100% (w/w), preferably 1.0-60% (w/w).

Specific examples of the carrier preferably include gelatin, lactose, refined sugar, titanium oxide, starch, crystalline cellulose, hydroxypropylmethylcellulose, carboxymethylcellulose, cornstarch, microcrystalline wax, white petrolatum, magnesium aluminometasilicate, anhydrous calcium phosphate, citric acid, trisodium citrate, hydroxypropyl cellulose, sorbitol, sorbitan esters of fatty acid, polyisobate, sucrose esters of fatty acid, polyoxyethylene hydrogenated castor oil, polyvinylpyrrolidone, magnesium stearate, light anhydrous silicic acid, talc, vegetable oil, benzyl alcohol, gum arabic, propylene glycol, polyalkylene glycol, cyclodextrin, and hydroxypropylcyclodextrin. However, the additives for pharmaceutical preparations are not limited to these examples.

Doses and administration frequencies of the medicaments of the present invention are not particularly limited, and suitable doses and administration frequencies can be determined depending on various factors such as purpose of administration, type of a disease, the age, body weight and symptoms of a patient and the like. In the case of oral administration, the medicament can be administered once to several times a day in an amount of 1-100 mg/kg based on the weight of the compound of the general formula (I) as a daily dose for an adult. In the case of parenteral administration, the medicament may preferably be administered once to several times a day in an amount of 0.1-100 mg/kg based on the weight of the compound of the general formula (I) as a daily dose for an adult.

Also, according to another embodiment of the present invention, a therapeutic process of infection comprising administering concomitantly or sequentially the compound of the general formula (I), a β-lactam antibiotic, and optionally furthermore a β-lactamase inhibitor or dehydropeptidase (DHP) inhibitor to animals including human being is provided.

Furthermore, according to another embodiment of the present invention, the use of the compound of the general formula (I) in order to prepare a pharmaceutical composition, especially a therapeutic agent of infections comprising a β-lactam antibiotic, and optionally furthermore a β-lactamase inhibitor or dehydropeptidase (DHP) inhibitor is provided.

Preparation of the Compound

The compound of the general formula (I) according to the present invention can be preferably prepared by the methods shown in the Schemes A-H or the similar methods.

As herein used, Me represents a methyl group, Et represents an ethyl group, TBS represents a t-butyldimethylsilyl group, TBDPS represents a t-butyldiphenylsilyl group, Ac represents an acetyl group, and Bn represents a benzyl group.

Scheme A
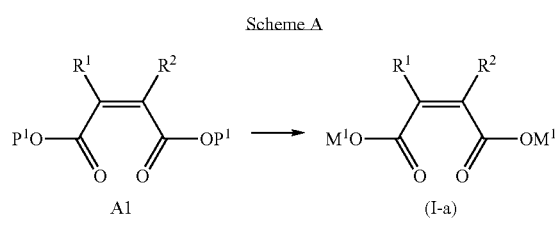
Scheme B
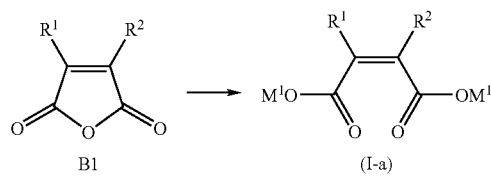
Scheme C
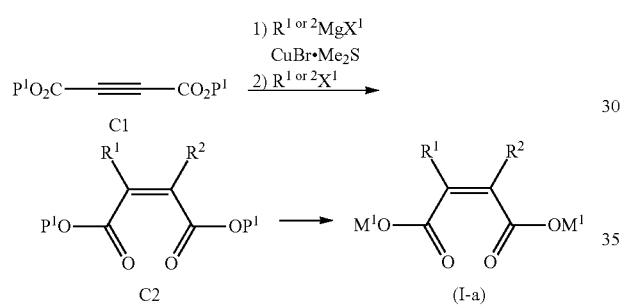
Scheme D
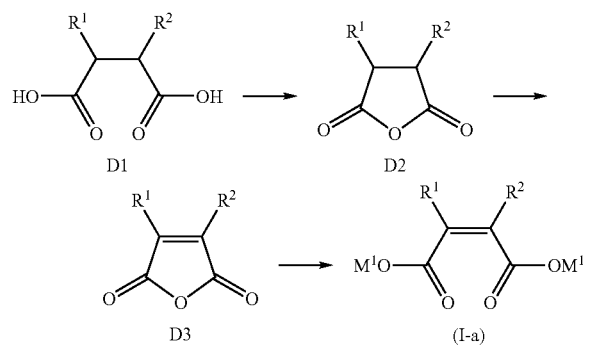
Scheme E
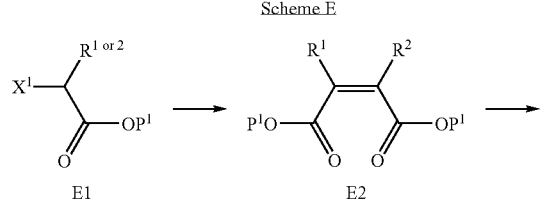
-continued
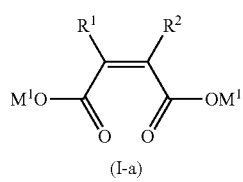
Scheme F
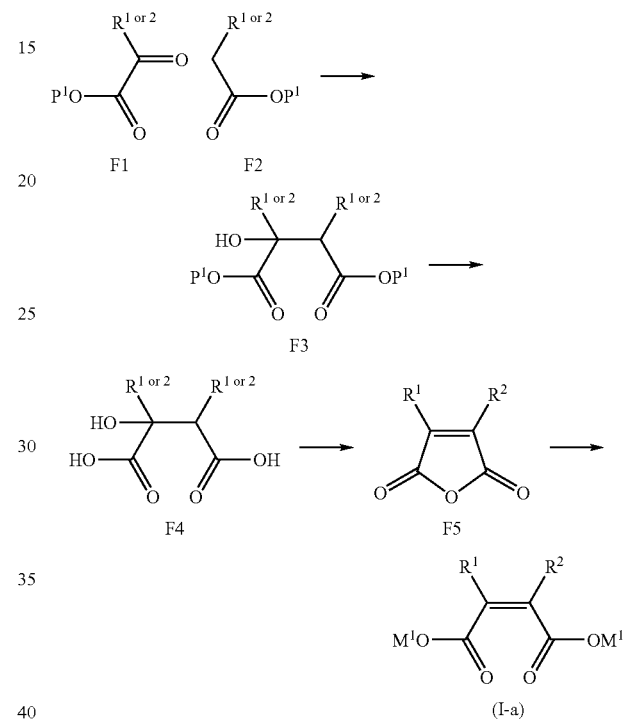
Scheme F'
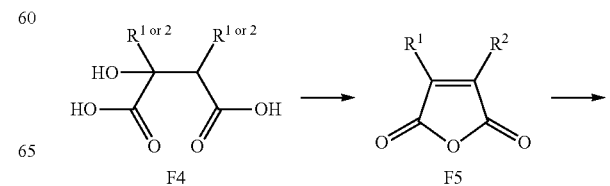

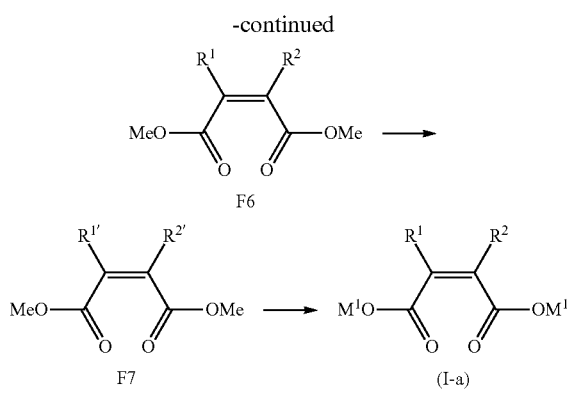

Scheme G

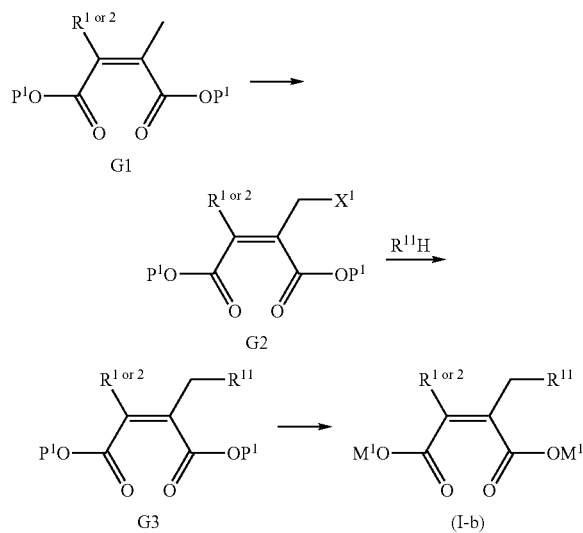

Scheme H

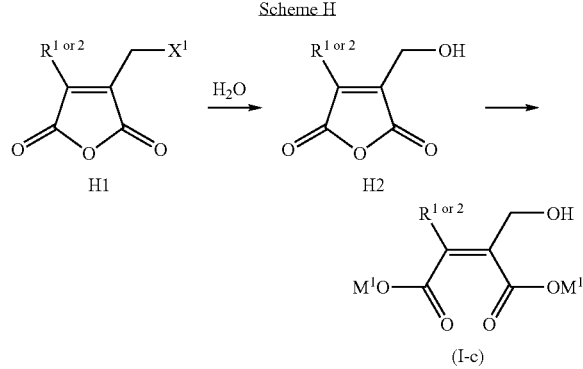

In the aforementioned Schemes A-H, $R^1$, $R^2$, and $M^1$ have the same meanings as those in $R^1$, $R^2$, and $M^1$ of the general formula (I). The compounds (I-a), (I-b) and (I-c) represent the compounds of the general formula (I) wherein $M^1$ represents a pharmaceutically acceptable cation. Also, $R^{11}$ represents a hydroxyl group, a thiol group, a —O—$C_{1-6}$ alkyl group, a —S—$C_{1-6}$ alkyl group, an amino group, an N-mono-substituted amino group, an N,N-di-substituted amino group, a heterocycle containing one nitrogen atom. $X^1$ represents a halogen atom, $P^1$ and $P^2$ represent a protective groups of a carboxyl group.

In Schemes A-H, it is possible to carry out at need the step of eliminating a protective group, in the case that the desired substituent is not conform to the reaction condition of synthesis used, with first introducing the substituent in the form of a protected derivative and eliminating the protective group after the reaction. It is also possible to convert the substituent itself via the step of eliminating a protective group at need.

The protective group may be appropriately determined by referring to Protective Groups in Organic Synthesis (T. W. Greene et al., Wiley, New York (1999)), and the like.

In the present invention, the protective group required is mainly a hydroxyl protective group, an amino protective group, or a carboxyl protective group.

Examples of the hydroxyl protective group include an acetyl group, a pivaloyl group, silyl groups such as triethylsilyl group, t-butyldimethylsilyl (TBS) group, and t-butyldiphenylsilyl (TBDPS) group, a benzyl group, a trytyl group, an o-nitrobenzyloxycarbonyl group, a p-nitrobenzyloxycarbonyl group, a benzyloxycarbonyl group, an allyloxycarbonyl group, a t-butyloxycarbonyl group, a 2,2,2-trichloroethyloxycarbonyl group, and the like.

Examples of the amino protective group include an acetyl group, a t-butoxycarbonyl group, a benzyl group, a benzyloxycarbonyl group, a benzenesulfonyl group, an o-nitrobenzenesulfonyl group, p-nitrobenzenesulfonyl group, and the like.

Examples of the carboxyl protective group include a methyl group, an ethyl group, a t-butyl group, an allyl group, a benzhydryl group, a 2-naphthylmethyl group, a benzyl group, a silyl group such as t-butyldimethylsilyl (TBS) group, a phenacyl group, a p-methoxybenzyl group, an o-nitrobenzyl group, a p-methoxyphenyl group, a p-nitrobenzyl group, a 4-pyridylmethyl group, a 1-(cyclohexyloxycarbonyloxy) ethyl group, an acetoxymethyl group, a 1-(isopropyloxycarbonyloxy)ethyl group, a 1-(ethoxycarbonyloxy)ethyl group, a pivaloyloxymethyl group, a cyclohexyloxycarbonyloxymethyl group, and the like.

Scheme A

This scheme illustrates a preferred process in case that a maleate diester, the raw material A1, is easily commercially available from a commercial source or can be easily prepared by a variety of methods well known in the art.

The conversion of the compound A1 to the compound (I-a) is carried out by changing $M^1$ into a metal cation at need, reacting the compound A1 with two or more equivalents of an aqueous solution of alkali hydroxide such as sodium hydroxide, potassium hydroxide, and lithium hydroxide in tetrahydrofuran, dioxane, diethyl ether, acetonitrile, dimethylformamide, methanol, ethanol, n-propanol, water, or a mixed solvent thereof at 0° C.-90° C. for 5 min to 48 h, then concentrating the reaction mixture at reduced pressure, and drying the concentrate in vacuum. Thus, the compound (I-a) can be obtained.

Scheme B

This scheme illustrates a preferred process in case that a maleic anhydride, the raw material B1, is easily commercially available from a commercial source or can be easily prepared by a variety of methods well known in the art.

The compound (I-a) is obtained by the ring opening reaction of the acid anhydride, the compound B1, according to the conventional method. If necessary, after $M^1$ is changed into a metal cation, the compound B1 is reacted with two or more equivalents of an aqueous solution of alkali hydroxide such as sodium hydroxide, potassium hydroxide, and lithium hydroxide in tetrahydrofuran, dioxane, diethyl ether, acetonitrile, dimethylformamide, methanol, ethanol, n-propanol, water, or a mixed solvent thereof at 0° C.-90° C. for 5 min to 48 h, then the reaction mixture is concentrated at reduced pressure, and the concentrate is dried in vacuum to give the compound (I-a).
Scheme C The conversion from the compound C1 to the compound C2 in this scheme can be carried out on the basis of the known method described in the literature (E. S. Ratemi et al., J. Org. Chem. 1996, 61, 6296) according to the following steps.

An acetylene dicarboxylic acid ester, the raw material C1, is easily commercially available from a commercial source or can be easily prepared by a variety of methods well known in the art.

The compound C1 is reacted with one equivalent or an excessive amount of magnesium alkyl halide $R^1$ (or $R^2$)$MgX^1$ in the presence of one equivalent or an excessive amount of bromo(dimethyl sulfide)copper(I) in tetrahydrofuran, dioxane, diethyl ether, toluene, benzene, hexamethylphosphoric triamide, dimethylformamide, dichloromethane, dichloroethane, hexane, or a mixed solvent thereof at −80° C. to 0° C. for 5 min to 5 h. Then, the anionic product at 2-position obtained is reacted with hexamethylphosphoric triamide and alkyl halide $R^1$ (or $R^2$)$X^1$ at −80° C. to 50° C. for 5 min to 5 h to give the compound C2 after usual treatment.

$R^1$ (or $R^2$)$MgX^1$ includes, for example, benzylmagnesium bromide, benzylmagnesium chloride, n-propylmagnesium chloride, t-butylmagnesium chloride, s-butylmagnesium bromide, c-hexylmagnesium bromide, c-pentylmagnesium bromide, ethylmagnesium bromide, ethylmagnesium chloride, n-heptylmagnesium bromide, n-hexylmagnesium bromide, i-propylmagnesium bromide, i-propylmagnesium chloride, methylmagnesium bromide, methylmagnesium iodide, n-octylmagnesium bromide, n-pentadecylmagnesium bromide, n-pentylmagnesium bromide, phenylmagnesium bromide, phenylmagnesium chloride, phenylmagnesium iodide, n-propylmagnesium bromide, n-tetradecylmagnesium chloride, o-trylmagnesium bromide, m-trylmagnesium bromide, p-trylmagnesium bromide, and vinylmagnesium bromide.

Also, $R^1$ (or $R^2$)$X^1$ includes, for example, methyl iodide, ethyl iodide, n-propyl iodide, i-propyl iodide, n-butyl iodide, s-butyl iodide, i-butyl iodide, methyl bromide, ethyl bromide, n-propyl bromide, i-propyl bromide, n-butyl bromide, s-butyl bromide, and i-butyl bromide.

Next, the conversion of the compound C2 into the compound (I-a) can be carried out according to the following steps. In this case, after $M^1$ is changed into a metal cation, the compound C2 is reacted with two equivalents or more of an aqueous solution of alkali hydroxide such as sodium hydroxide, potassium hydroxide, lithium hydroxide, and the like in tetrahydrofuran, dioxane, diethyl ether, acetonitrile, dimethylformamide, methanol, ethanol, n-propanol, water, or a mixed solvent thereof at 0° C. to 90° C. for 5 min to 48 h, then the reaction mixture is concentrated at reduced pressure, and the concentrate is dried in vacuum to give the compound (I-a).
Scheme D This scheme illustrates a preferred process in case that a succinic acid derivative, the raw material D1, is the one which is easily commercially available from a commercial source or can be easily prepared by a variety of methods well known in the art (e.g. Japanese Patent Publication No. 2003-513890). The conversion of the compound D1 into the compound D3 can be carried out on the basis of the known method described in the literature (M. J. Kates et al., J. Org. Chem. 1996, 61, 4164). That is, the compound D1 is reacted with one equivalent or an excessive amount of a halogenated formic acid ester such as methyl chloroformate or ethyl chloroformate in the presence of one equivalent or an excessive amount of a base in tetrahydrofuran, dioxane, diethyl ether, toluene, benzene, hexamethylphosphoric triamide, dimethylformamide, dichloromethane, dichloroethane, hexane, or a mixed solvent thereof at −80° C. to 80° C. for 5 min to 8 h, and the reaction mixture is concentrated under reduced pressure to give the compound D2. The aforementioned base includes, for example, organic bases such as diisopropylethylamine, triethylamine, 2,6-lutidine, pyridine, N-methylmorpholine, and the like, and inorganic bases such as sodium hydride, sodium hydroxide, potassium hydroxide, sodium methoxide, sodium ethoxide, potassium t-butoxide, sodium hydrogen carbonate, potassium hydrogen carbonate, sodium carbonate, potassium carbonate, cesium carbonate, and the like.

Next, the conversion of the compound D2 into the compound D3 can be carried out by the following method. That is, the compound D2 is reacted with one equivalent or an excessive amount of trimethylsilyl trifluoromethanesulfonic acid in the presence of a base in tetrahydrofuran, dioxane, diethyl ether, toluene, benzene, hexamethylphosphoric triamide, dimethylformamide, dichloromethane, dichloroethane, hexane, or a mixed solvent thereof at −80° C. to 100° C. for 5 min to 5 h, then with a catalytic amount or more of tetrabutylammonium bromide and one equivalent or an excessive amount of bromine at −80° C. to 100° C. for 5 min to 8 h, and then the reaction mixture is treated in the usual manner to give the compound D3. The aforementioned base includes, for example, organic bases such as diisopropylethylamine, triethylamine, 2,6-lutidine, pyridine, N-methylmorpholine, and the like, and inorganic bases such as sodium hydride, sodium hydroxide, potassium hydroxide, sodium methoxide, sodium ethoxide, potassium-t-butoxide, sodium hydrogen carbonate, potassium hydrogen carbonate, sodium carbonate, potassium carbonate, cesium carbonate, and the like.

Then, the compound (I-a) is obtained by the ring opening reaction of the compound D3, the acid anhydride, according to the conventional method. If necessary, after $M^1$ is changed into a metal cation, the compound D3 is reacted with two equivalents or more of an aqueous solution of an alkali hydroxide such as sodium hydroxide, potassium hydroxide, lithium hydroxide, and the like in tetrahydrofuran, dioxane, diethyl ether, acetonitrile, dimethylformamide, methanol, ethanol, n-propanol, water, or a mixed solvent thereof at 0° C. to 90° C. for 5 min to 48 h, and the reaction mixture is concentrated under reduced pressure and dried in vacuum to give the compound (I-a).
Scheme E The conversion of the compound E1 to the compound E2 can be carried out by the following method on the basis of the known method described in the literature (H. Hagiwara et al., Synthetic Commun. 1984, 14, 1193). The α-halogenated carboxylic acid derivative E1 is commercially available from a commercial source or can be easily prepared by a variety of methods well known in the art. The compound E1 is reacted with one equivalent or an excessive amount of a strong base such as lithium diisopropylamide, lithium hexamethyldisilazane, potassium hexamethyldisilazane, sodium hydride, potassium hydride, or the like and a catalytic amount or more of a copper (I) halide such as copper (I) chloride, copper (I) bromide, and copper (I) iodide in tetrahydrofuran, dioxane, diethyl ether, toluene, benzene, hexamethylphosphoric triamide, dimethylformamide, dichloromethane, dichloroethane, hexane, or a mixed solvent thereof at −90° C. to 20° C. for 5 min to 5 h, and then the reaction mixture is treated in the usual manner to give the compound E2. In addition, this scheme is based on the dimer type reaction and thus most appropriate to the synthesis of symmetrically 2,3-di-substituted maleic acids.

Next, the conversion of the compound E2 to the compound (I-a) can be carried out by the following method. After $M^1$ is changed into a metal cation, the compound E2 is reacted with two equivalents or more of an aqueous solution of an alkali hydroxide such as sodium hydroxide, potassium hydroxide, lithium hydroxide, and the like in tetrahydrofuran, dioxane, diethyl ether, acetonitrile, dimethylformamide, methanol, ethanol, n-propanol, water, or a mixed solvent thereof at 0° C. to 90° C. for 5 min to 48 h, then the reaction mixture is concentrated at reduced pressure and dried in vacuum to give the compound (I-a).

Scheme F

The conversion of the compounds F1 and F2 to the compound F5 can be carried out by the following method on the basis of the known method described in the literature (S. B. Singh et al., Bioorg. Med. Chem. 2000, 8, 571). The pyruvic acid derivative F1 and the compound F2 are commercially available from a commercial source or can be easily prepared by a variety of methods well known in the art. That is, one equivalent or an excessive amount of compound F2 is reacted with one equivalent or an excessive amount of a strong base such as lithium diisopropylamide, lithium hexamethyldisilazane, potassium hexamethyldisilazane, sodium hydride, or potassium hydride in tetrahydrofuran, dioxane, diethyl ether, toluene, benzene, hexamethylphosphoric triamide, dimethylformamide, dichloromethane, dichloroethane, hexane, or a mixed solvent thereof at −90° C. to 20° C. for 5 min to 5 h. The enolate thus obtained is reacted with the compound F1 at −90° C. to 20° C. for 5 min to 5 h, the reaction mixture is treated in the usual manner to give the compound F3.

Next, the conversion of the compound F3 to the compound F4 can be carried out by the following method. The compound F3 is reacted with two equivalents or more of an aqueous solution of an alkali hydroxide such as sodium hydroxide, potassium hydroxide, lithium hydroxide, and the like in tetrahydrofuran, dioxane, diethyl ether, acetonitrile, dimethylformamide, methanol, ethanol, n-propanol, water or a mixed solvent thereof at 70° C. to 100° C. for 1 h to 48 h, and then the reaction mixture is treated in the usual manner to give the compound F4.

When $P^1$ in the compound F3 is a protective group such as benzyl group which can be removed by hydrogenation reaction, the conversion of F3 into the compound F4 can be carried out by the following manner. That is, the compound F3 is hydrogenated under a vigorous stirring condition in the presence of a catalytic amount of a metal catalyst such as nickel or palladium in methanol, ethanol, tetrahydrofuran, dioxane, diethyl ether, hexane, toluene, water or a mixed solvent thereof in the hydrogen stream at 0° C. to 50° C. for 1 h to 48 h, and then the reaction mixture is treated in the usual manner to give the compound F4.

Next, the conversion of the compound F4 to the compound F5 can be carried out by the following method. The compound F4 is reacted with an excessive amount of acetic anhydride at 70° C. to 140° C. for 1 h to 48 h, and then the reaction mixture is treated in the usual manner to give the compound F5.

The compound (I-a) is obtained by the ring opening reaction of the compound F5, the acid anhydride, to give the compound (I-a) according to the standard method. After $M^1$ is changed into a metal cation at need, the compound F4 is reacted with two equivalents or more of an aqueous solution of an alkali hydroxide such as sodium hydroxide, potassium hydroxide, lithium hydroxide, and the like at 0° C. to 90° C. for 5 min to 48 h in tetrahydrofuran, dioxane, diethyl ether, acetonitrile, dimethylformamide, methanol, ethanol, n-propanol, water, or a mixed solvent thereof, and then the reaction mixture is concentrated under reduced pressure and dried in vacuum to give the compound (I-a).

Scheme F'

The conversion from the compounds F1 and F2 into the compound F5 can be carried out by the method described in Scheme F. $R^{1'}$ and $R^{2'}$ have the same meanings as those in $R^1$, and either or both of $R^{1'}$ or $R^{2'}$ represent a different substituent from $R^1$ or $R^2$.

Next, the conversion from the compound F5 into the compound F6 can be carried out by the following method. The compound F5 is reacted with one equivalent or an excessive amount of trimethylsilyl diazomethane or the like in an alcohol such as methanol at 0° C. to 20° C. for 5 min to 8 h, and the reaction mixture is subjected to the usual post-treatment to give the compound F6.

The conversion of the compound F6 into the compound F7 can be carried out by a variety of methods known in the art, in which $R^1$ and $R^2$ in the compound F6 are changed into the other $R^1$ and $R^2$.

Next, compound F7 (7)compound (I-a) can be carried out by the following method. In this case, after $M^1$ is changed into a metal cation, the compound F7 is reacted with two equivalents or more of an aqueous solution of an alkali hydroxide such as sodium hydroxide, potassium hydroxide, lithium hydroxide, and the like in tetrahydrofuran, dioxane, diethyl ether, acetonitrile, dimethylformamide, methanol, ethanol, n-propanol, water, or a mixed solvent thereof at 0° C. to 90° C. for 5 min to 48 h, and then the reaction mixture is concentrated under reduced pressure and dried in vacuum to give the compound (I-a).

Scheme G

The conversion from the compound G1 into the compound G2 can be carried out by the following method. That is, the compound G1 which is easily commercially available from a commercial source or can be easily prepared by a variety of methods known in the art (e.g., E. S. Ratemi et al., J. Org. Chem. 1996, 61, 6296) is reacted with one equivalent or an excessive amount of N-halogenated succinimide such as N-bromosuccinimide or N-chlorosuccinimide and a catalytic amount or more of a radical initiator such as 2,2'-azobisisobutyronitrile, dibenzoyl peroxide, and the like in carbon tetrachloride at 0° C. to 80° C. for 5 min to 48 h, and the reaction mixture is subjected to the usual post-treatment to give the compound G2.

Next, the conversion of the compound G2 into compound G3 can be carried out by the following method. That is, the compound G2 is reacted with water, hydrogen sulfide, alcohol, thiol or the like in tetrahydrofuran, dioxane, diethyl ether, toluene, benzene, hexamethylphosphoric triamide, dimethylformamide, dichloromethane, dichloroethane, hexane or a mixed solvent thereof in the presence of a primary amine, a secondary amine including a cyclic amine or a base at −80° C. to 100° C. for 5 min to 48 h, and the reaction mixture is subjected to the usual post-treatment to give the compound G3.

Next, the conversion of the compound G3 into the compound (I-b) can be carried out by the following method. In this case, after $M^1$ is changed into a metal cation, the compound G3 is reacted with two equivalents or more of an aqueous solution of an alkali hydroxide such as sodium hydroxide, potassium hydroxide, lithium hydroxide, and the like in tetrahydrofuran, dioxane, diethyl ether, acetonitrile, dimethylformamide, methanol, ethanol, n-propanol, water, or a mixed solvent thereof at 0° C. to 90° C. for 5 min to 48 h, and the reaction mixture is then concentrated under reduced pressure and dried in vacuum to give the compound (I-b).
Scheme H The compound H1 in this scheme is easily commercially available from commercial sources or can be easily manufactured by a variety of methods well known in the art (e.g., A. M. Despande et al., Synthesis 2001, 5, 702). The conversion from the compound H1 into the compound H2 can be carried out by the following method. That is, the compound H1 is reacted with an excessive amount of water in the presence of a base in tetrahydrofuran, dioxane, diethyl ether, hexamethylphosphoric triamide, dimethylformamide or a mixed solvent thereof at 0° C. to 100° C. for 5 min to 48 h, and the reaction mixture is then subjected to the usual post-treatment to give the compound H2.

Next, the conversion of the compound H2 into the compound (I-c) can be carried out by the following method. In this case, after $M^1$ is changed into a metal cation, the compound H2 is reacted with two equivalents or more of an aqueous solution of an alkali hydroxide such as sodium hydroxide, potassium hydroxide, lithium hydroxide, and the like in tetrahydrofuran, dioxane, diethyl ether, acetonitrile, dimethylformamide, methanol, ethanol, n-propanol, water, or a mixed solvent thereof at 0° C. to 90° C. for 5 min to 48 h, and the reaction mixture is then concentrated under reduced pressure and dried in vacuum to give the compound (I-c).

As described above, the compounds (I-a), (I-b) and (I-c) obtained in Schemes A-H can be refined by chromatography with non-ionic porous resin, gel filtration with Sephadex, normal phase or reversed phase chromatography, crystallization, and the other methods, if necessary.

Conversion of $M^1$ in the General Formula (I)

The compound (I-a), (I-b) or (I-c) as the alkali salt such as a sodium salt or a potassium salt is reacted with two equivalents or more of a hydrochloride salt of amines such as ammonia, methylamine, dimethylamine, trimethylamine, ethylamine, diethylamine, or triethylamine in tetrahydrofuran, dioxane, diethyl ether, acetonitrile, dimethylformamide, methanol, ethanol, n-propanol, water, or a mixed solvent thereof at 0° C. to 90° C. for 5 min to 48 h, and the reaction mixture is then concentrated under reduced pressure and dried in vacuum to give the ammonium salt of the general formula (I).

The ammonium salt of the general formula (I) thus obtained can also be refined by chromatography with non-ionic porous resin, gel filtration with Sephadex, normal phase or reversed phase chromatography, crystallization, and the other methods, if necessary.

Also, the compound of the general formula (I) in which $M^1$ is an in vivo hydrolyzable group can be obtained by the following method.

The compound described above is obtained by reacting the above described (I-a), (I-b) or (I-c) in the form of an alkali metal salt such as a sodium salt or a potassium salt in which $M^1$ is a metal cation with a halide compound of the in vivo hydrolyzable group $M^6$-$X^2$.

$M^6$ has the same meaning as the in vivo hydrolyzable group of the general formula (I) described above, $X^2$ represents an eliminable group such as chlorine, bromine, iodine, —$OSO_2CF_3$, —$OSO_2CH_3$, —$OSO_2PhCH_3$, and the like. The compound of the general formula (I) can be obtained by reacting (I-a), (I-b) or (I-c), as occasion demands, with two equivalents or more of an alkyl halide ($M^6$-$X^2$:) in the presence of a catalytic amount or an excessive amount of a base at −70° C. to 50° C., preferably at −30° C. to 30° C. for 10 min to 24 h, thus obtaining the compound of the general formula (I) in which $M^1$ is an in vivo hydrolyzable group. The base described above includes organic bases such as diisopropylethylamine, 1,8-diazabicyclo[5.4.0]-7-undecene, 2,6-lutidine, and the like and inorganic bases such as sodium hydroxide, potassium hydroxide, sodium hydrogen carbonate, potassium hydrogen carbonate, sodium carbonate, potassium carbonate, cesium carbonate, and the like. The alkyl halide described above is represented by $M^6$-$X^2$, in which $X^2$ represents a halogen atom or an eliminable group and includes preferably iodine, bromine, or chlorine. Examples include methyl iodide, ethyl iodide, 1-(cyclohexyloxycarbonyloxy) ethyl iodide, acetic acid bromomethyl 1-(isopropyloxycarbonyloxy)ethyl iodide, 1-(ethoxycarbonyloxy)ethyl iodide, iodomethyl pivalate, cyclohexyloxycarbonyloxymethyl iodide, 1-(isobutyloxycarbonyloxy)ethyl iodide, 1-(cyclohexyloxycarbonyloxy)-2-methylpropan-1-yl iodide, isobutyloxycarbonyloxymethyl iodide, isopropyloxycarbonyloxymethyl iodide, isobutyryloxymethyl iodide, (pentan-1-yl)oxycarbonyloxymethyl iodide, (butan-1-yl)oxycarbonyloxymethyl iodide, (1-ethylpropan-1-yl)oxycarbonyloxymethyl iodide, isopentyloxycarbonyloxymethyl iodide, (propan-1-yl)oxymethyl iodide, ethoxycarbonyloxymethyl iodide, neopentyloxycarbonyloxymethyl iodide, methoxycarbonyloxymethyl iodide, cyclopentyloxycarbonyloxymethyl iodide, t-butoxycarbonyloxymethyl iodide, 3-bromophthalide, 1-(methoxycarbonyloxy)ethyl iodide, 1-(cyclopentyloxycarbonyloxy) ethyl iodide, (tetrahydropyran-4-yl)oxycarbonyloxymethyl iodide, 1-(neopentyloxycarbonyloxy)ethyl iodide, (piperidin-1-yl)carbonyloxymethyl iodide, allyl iodide, 1-(t-butoxycarbonyloxy)ethyl iodide, N,N-di(propan-1-yl)aminocarbonyloxymethyl iodide, phenyloxycarbonyloxymethyl iodide, (5-methyl-2-oxo-1,3-dioxolen-4-yl)methyl bromide, (Z)-2-(3-phthalidylidene)ethyl bromide, (cis-2,6-dimethylpiperidin-1-yl)carbonyloxymethyl chloride, chloromethyl N,N-di-n-butylcarbamate, 1-iodohexane, chloromethyl N-n-hexyl-N-methylcarbamate, chloromethyl N,N-diisobutylcarbamate, chloromethyl N,N-diisopropylcarbamate, chloromethyl N-cyclohexyl-N-methylcarbamate, chloromethyl N-pentan-1-ylcarbamate, chloromethyl N-cyclohexyl-N-ethylcarbamate, chloromethyl N-isobutyl-N-isopropylcarbamate, chloromethyl N-t-butyl-N-ethylcarbamate, 1-chloroethyl N,N-diisopropylcarbamate, 1-[(cis-2,6-dimethylpiperidin-1-yl)carbonyloxy]ethyl chloride, chloromethyl N-ethyl-N-isoamylcarbamate, and the like. In a single or mixed inert solvent (e.g., N,N-dimethylformamide, N,N-dimethylacetamide, N,N-diethylformamide, N,N-diethylacetamide, N-methylpyrrolidinone, N,N-dimethylimidazolidinone, dimethylsulfoxide, sulfolane, acetonitrile, acetone, ethyl acetate, tetrahydrofuran, 1,4-dioxane, diethyl ether, anisole, dichloromethane, 1,2-dichloroethane, chloroform, toluene, benzene, hexamethylphosphoric triamide, methanol, ethanol, and the like. It is also possible to obtain the compound of the general formula (I) by preliminarily introducing an in vivo hydrolyzable group into the corresponding portion to $M^1$ at the initial stage of Schemes A-H and conducting the treatment according to each of the schemes.

The ester compound (I) thus obtained can be isolated and refined by precipitation, gel filtration with Sephadex, normal phase or reversed phase chromatography, and the like.
Novel Compounds Represented by the General Formulae (II), (III), (IV) and (V)

The group of the compounds represented by the general formula (I) includes novel compounds. Thus, according to another embodiment of the present invention are provided novel 2,3-di-substituted maleic acid derivatives, specifically the novel compounds represented by the general formulae (II), (III), (IV) and (V).

Compound of the General Formula (II)

In the formula (II), $R^3$ represents a $C_{2-6}$ alkyl group, a $C_{3-7}$ cycloalkyl group or a hydroxymethyl group, all of which may be substituted, and $R^4$ represents a $C_{1-6}$ alkyl group or a $C_{3-7}$ cycloalkyl group, all of which may be substituted. As herein used, the terms "$C_{1-6}$ alkyl group" or "$C_{2-6}$ alkyl group" represented by $R^3$ or $R^4$ may be either of a linear or branched chain and preferably represent a $C_{1-4}$ alkyl or a $C_{2-4}$ alkyl group, including, for example, a methyl group, an ethyl group, a n-propyl group, an i-propyl group, a n-butyl group, an i-butyl group, a s-butyl group, a t-butyl group, a n-pentyl group, a neopentyl group, an i-pentyl group, a t-pentyl group, a n-hexyl group, an i-hexyl group, and the like. The term represented by "$C_{3-7}$ cycloalkyl group" represented by $R^3$ or $R^4$ includes preferably a cyclopropyl group, a cyclobutyl group, a cyclopentyl group, a cyclohexyl group, a cycloheptyl group, and the like, more preferably a cyclopentyl group, a cyclohexyl group, and a cycloheptyl group.

All of these groups may be substituted as described on the general formula (I), and their preferred examples are also the same as in the general formula (I).

$M^2$ represents a hydrogen atom, a pharmaceutically acceptable cation, or a pharmaceutically acceptable group which may be hydrolyzed in vivo.

The term "pharmaceutically acceptable cation" represented by $M^2$ has the same meaning as the general formula (I).

Compound of the General Formula (III)

$R^5$ represents an ethyl group, and $R^6$ represents a $C_{1-3}$ linear alkyl group, i.e. a methyl group, an ethyl group and a propyl group.

$M^3$ may be the same or different and represents a "pharmaceutically acceptable cation", and a "pharmaceutically acceptable group which may be hydrolyzed in vivo". In other words, it represents a salt or an ester which has an in vivo hydrolyzable group.

The term "pharmaceutically acceptable cation" represented by $M^3$ has the same meanings as those of the general formulae (I) and (II).

The term "pharmaceutically acceptable group which may be hydrolyzed in vivo" represented by $M^3$ represents an eliminable group linked to one or both of the carboxyl groups of the general formula (III), which represents a group metabolized, hydrolyzed and removed in vivo to give a carboxyl group, and has the same meanings as those of the general formula (II).

Compound of the General Formula (IV)

The terms "$C_{1-6}$ alkyl group" represented by $R^7$ and "$C_{3-7}$ cycloalkyl group" represented by $R^7$ have the same meanings as those of the general formulae (I) and (II), and their preferred examples also have the same meanings as those of the general formula (I).

The term "—$C_{1-3}$ alkylene-phenyl group" represented by $R^7$ or $R^8$ has the same meanings as those of the general formula (I), and their preferred examples also have the same meanings as those of the general formula (I).

The terms "—$C_1$ alkylene-ring A" represented by $R^7$ or "—$C_{0-1}$ alkylene-ring A" represented by $R^8$ represent that the alkylene is linked with the ring A via methylene or methylene/bond, and the ring A represents a five- to ten-membered mono-cyclic or bi-cyclic heterocyclic ring containing 1 to 4 nitrogen, oxygen or sulfur atoms, more preferably, a five- or six-membered saturated or unsaturated heterocycle containing one nitrogen or oxygen atom. The specific examples of the "heterocycle" include tetrahydrofuran, furan, pyrrolidine, piperidine, pyrazolidine, imidazolidine, piperazine, morpholine, thiomorpholine, pyrrole, thiophene, oxazole, isoxazole, thiazole, isothiazole, imidazole, pyrazole, pyridine, pyridazine, pyrimidine, pyrazine, triazole, tetrazole, thiadiazole, azetidine, thiazoline, quinuclidine, triazine, isobenzofuran, indole, indolizine, chromene, quinoline, isoquinoline, cinnoline, quinazoline, quinoxaline, phthalazine, purine, pteridine, and the like. The bond or the methylene group may be linked with any position of the heterocycle. However, if $R^7$ is a $C_{1-6}$ alkyl group, $R^8$ does not represent dihydrofuran.

The terms "—O—$C_{1-6}$ alkyl group" represented by $R^7$ or $R^8$ and "—S—$C_{1-6}$ alkyl group" represented by $R^7$ or $R^8$ have the same meanings as those of the general formula (I), and their preferred examples also have the same meanings as those of the general formula (I).

These groups may be substituted as described above. $M^4$, which may be the same or different, represents a hydrogen atom, a "pharmaceutically acceptable cation" or a "pharmaceutically acceptable group which may be hydrolyzed in vivo".

The term "pharmaceutically acceptable cation" represented by $M^4$ has the same meanings as those of the general formulae (I) and (II), and the preferred examples also have the same meanings as those of the general formula (I).

The term "pharmaceutically acceptable group which may be hydrolyzed in vivo" represented by $M^4$ represents an eliminable group which is linked with one or both of the carboxyl groups of the general formula (IV), which represents a group metabolized, hydrolyzed and removed in vivo to give a carboxyl group, and has the same meanings as those of the general formula (II).

Compound of the General Formula (V)

The terms "$C_{1-6}$ alkyl group" represented by $R^9$ and "$C_{3-7}$ cycloalkyl group" represented by $R^9$ have the same meanings as those of the general formula (I) and (II), and the preferred examples also have the same meanings as those of the general formula (I).

The term "—$C_{1-3}$ alkylene-phenyl group" represented by $R^9$ or $R^{10}$ has the same meanings as those of the general formula (I), and the preferred examples also have the same meanings as those of the general formula (I).

The term "—$C_{0-1}$ alkylene-ring B" represented by $R^9$ or $R^{10}$ represents that the alkylene is linked with the ring B via a bond or methylene, and the ring B represents pyridine, piperidine, or tetrahydropyran. However, $R^9$ and $R^{10}$ do not represent pyridinium which is a quaternary salt formed by bonding at the nitrogen atom on the pyridine ring.

The terms "—O—$C_{1-6}$ alkyl group" or "—S—$C_{1-6}$ alkyl group" represented by $R^9$ or $R^{10}$ have the same meanings as those of the general formula (I), and the preferred examples also have the same meanings as those of the general formula (I).

These groups may be substituted as described above. The substituent $M^5$, which may be the same or different, represents a hydrogen atom, a "pharmaceutically acceptable cation" or a "pharmaceutically acceptable group which may be hydrolyzed in vivo".

The term "pharmaceutically acceptable cation" represented by $M^4$ has the same meanings as those of the general formulae (I) and (II), and the preferred examples also have the same meanings as those of the general formula (I).

The term "pharmaceutically acceptable group which may be hydrolyzed in vivo" represented by $M^4$ represents an eliminable group which is linked with one or both of the carboxyl groups of the general formula (V), which represents a group metabolized, hydrolyzed and removed in vivo to give a carboxyl group, and has the same meanings as those of the general formula (II).

The compounds of the general formulae (II)-(V) can be prepared according to the above described methods for preparing the compound of the general formula (I).

Also, the compounds of the general formulae (II)-(V) can be also prepared in the similar manner to the compound of the general formula (I) by well known methods, or the methods described in Schemes A-H or similar thereto.

EXAMPLES

The present invention is now explained by way of examples below, but it is not limited to these examples. In addition, the structures of the compounds prepared in Examples are shown in Tables 1-1-5.

Example 1

2-ethyl-3-methylmaleic acid dimethyl ester

To a suspension of bromo(dimethylsulfide)copper (I) (1.08 g, 5.25 mmol) in anhdrous tetrahydrofuran (24 mL), a 1.06 M ethylmagnesium chloride-tetrahydrofuran solution (4.8 mL, 5.1 mmol) was added dropwise under vigorous stirring at −50° C. The mixture was stirred at the same temperature for 2 h, and further stirred at −78° C. for 5 min. Then, a solution of dimethyl acetylenedicarboxylate (563 mg, 3.96 mmol) in tetrahydrofuran (8 mL) was added dropwise to the mixture. After 40 min, a solution of 4 mL of hexamethylphosphoric triamide in tetrahydrofuran (4 mL) was added dropwise, and a solution of methyl iodide (1.44 g, 10.1 mmol) in tetrahydrofuran (8 mL) was further added dropwise. After stirring for 20 min, the reaction mixture was warmed up to room temperature. An aqueous solution of saturated ammonium chloride (10 mL, adjusted to pH 8 with aqueous ammonia) was added at −20° C., and the temperature was again raised to room temperature. The reaction solvent was evaporated under reduced pressure, and diethyl ether and water were added to separate the phases. The aqueous layer was extracted three times with diethyl ether, and the combined organic layer was washed with an aqueous solution of saturated ammonium chloridewater, and brine. The residue obtained by concentrating the organic layer under reduced pressure was subjected to silica gel column chromatography (hexane-ethyl acetate 9:1) to give 98.2 mg of the title compound as a syrup (yield: 14%).

$^1$H NMR (CDCl$_3$) δ 1.07 (t, J=7.5 Hz, 3H), 1.95 (s, 3H), 2.37 (q, J=7.5 Hz, 2H), 3.75 (s, 3H), 3.78 (s, 3H).

Example 2

2-Ethyl-3-methylmaleic acid disodium

2-Ethyl-3-methylmaleic acid dimethyl ester (86.5 mg, 0.465 mmol) was dissolved in 1,4-dioxane (1.0 mL), 1 M sodium hydroxide aqueous solution (0.93 mL, 0.93 mmol) was added at room temperature, and the mixture was stirred at 50° C. for 4 h. The reaction solvent was evaporated under reduced pressure, and the residue thus obtained was dried in vacuum to give 93.8 mg (quantitative) of the title compound as a solid.

$^1$H NMR (D$_2$O) δ 0.81 (t, J=7.6 Hz, 3H), 1.64 (s, 3H), 2.08 (q, J=7.6 Hz, 2H); MS (FAB+) m/z 203 [(M+H)$^+$].

Example 3

2,3-Diethyl maleic acid diethyl ester

To a solution of diisopropylamine (654 mg, 6.46 mmol) in anhydrous tetrahydrofuran (5 mL) under the atmosphere of argon was added a 1.58 M n-butyl lithium-hexane solution (3.9 mL, 6.4 mmol) with stirring under ice cooling, and the mixture was stirred at 0° C. for 10 min and at −90° C. for 5 min. To the mixture, a solution of ethyl 2-bromo-n-butyrate (1.00 g, 5.13 mmol) in anhydrous tetrahydrofuran (9.5 mL) was added dropwise at −90° C., and the mixture was stirred for 30 min. Copper (I) iodide (489 mg, 2.56 mmol) was added at the same temperature, and the mixture was vigorously stirred further 5 min. The temperature was raised to 0° C. with stirring, and a saturated aqueous ammonium chloride solution (30 mL) was added. The reaction mixture was directly filtered, and the filtrate was concentrated under reduced pressure. The residue was diluted with water and extracted twice with ethyl acetate, and the combined organic layer was washed sequentially with water and brine and concentrated. The residue thus obtained was subjected to silica gel column chromatography (hexane-ethyl acetate 9:1) to give 368.4 mg of the title compound as oil (yield: 63%).

$^1$H NMR (CDCl$_3$) δ 1.07 (t, J=7.5 Hz, 6H), 1.30 (t, J=7.1 Hz, 6H), 2.37 (q, J=7.5 Hz, 4H), 4.22 (q, J=7.1 Hz, 4H); MS (ESI+) m/z 229 [(M+H)$^+$].

Example 4

2,3-Diethylmaleic acid disodium

To a solution of 2,3-diethylmaleic acid diethyl ester (368 mg, 1.61 mmol) in 1,4-dioxane (3.2 mL) was added a 1 M sodium hydroxide aqueous solution (3.2 mL, 3.2 mmol) at room temperature, and the mixture was stirred at 50° C. for 15 h. The reaction mixture was concentrated under reduced pressure, and the residue obtained was dried in vacuum to give 346 mg of the title compound as a colorless solid (quantitative).

$^1$H NMR (D$_2$O) δ 0.83 (t, J=7.5 Hz, 6H), 2.11 (q, J=7.5 Hz, 4H); MS (FAB+) m/z 217 [(M+H)$^+$].

Example 5

2,3-Diethylmaleic acid dipotassium 2,3-Diethylmaleic acid diethyl ester was reacted with 1 M aqueous potassium hydroxide solution in the same manner as Example 4 to give the title compound as a solid (quantitative). MS (FAB+) m/z 249 [(M+H)$^+$].

Example 6

2,3-Di-n-propylmaleic acid diethyl ester

The title compound was obtained as oil (yield: 85%) from ethyl 2-bromo-n-valerate in the same manner as Example 3.

$^1$H NMR (CDCl$_3$) δ 0.95 (t, J=7.5 Hz, 6H), 1.30 (t, J=7.2 Hz, 6H), 1.47 (m, 4H), 2.33 (m, 4H), 4.20 (q, J=7.2 Hz, 4H).

Example 7

2,3-Di-n-propylmaleic acid disodium

The title compound was obtained as a solid (quantitative) from 2,3-di-n-propylmaleic acid diethyl ester in the same manner as Example 2.

$^1$H NMR (D$_2$O) δ 0.74 (t, J=7.5 Hz, 6H), 1.20 (tq, J=7.5, 7.8 Hz, 4H) 2.07 (t, J=7.8 Hz, 4H); MS (FAB+) m/z 245 [(M+H)$^+$].

Example 8

2-Benzyl-3-methylmaleic acid dimethyl ester

Dimethyl acetylenedicarboxylate was reacted with benzylmagnesium chloride and methyl iodide in the same manner as Example 1 to give the title compound as oil (yield: 24%).
$^1$H NMR (CDCl$_3$) δ 2.04 (s, 3H), 3.66 (s, 3H), 3.72 (s, 2H), 3.78 (s, 3H), 7.15-7.32 (m, 5H).

Example 9

2-Benzyl-3-methylmaleic acid disodium

The title compound was obtained as a solid (quantitative) from 2-benzyl-3-methylmaleic acid dimethyl ester in the same manner as Example 2.
$^1$H NMR (D$_2$O) δ 1.75 (s, 3H), 3.49 (s, 2H), 7.09-7.23 (m, 5H); MS (FAB+) m/z 265 [(M+H)$^+$].

Example 10

Synthesis Example

2-Benzyl-3-ethylmaleic anhydride a) To anhydrous tetrahydrofuran (5 mL) was added diisopropylamine (759 mg, 7.5 mmol) under nitrogen stream, and the solution was cooled to −78° C. To this solution was added a 1.58 M n-butyl lithium-hexane solution (4.3 mL, 6.8 mmol), and the mixture was stirred at −78° C. for 5 min and at 0° C. for 15 min. A solution of lithium diisopropylamide tetrahydrofuran thus obtained above was cooled to −78° C. To the solution, a solution of 3-phenylpropionic acid ethyl ester (891 mg, 5.0 mmol) in anhydrous tetrahydrofuran (10 mL) was added dropwise over 1 h, and the reaction mixture was further stirred at −78° C. for 1 h. The cold solution of the enolate thus prepared above was added dropwise via a cannula to a solution of ethyl 2-ketobutyrate (781 mg, 6.0 mmol) in anhydrous tetrahydrofuran (5 mL) having been cooled to −78° C. After stirring at −78° C. for 2 h, the reaction mixture was quenched with a 10% aqueous citric acid solution, and extracted with ethyl acetate. The organic layer was washed with 1 M hydrochloric acid, a saturated aqueous sodium hydrogen carbonate solution and brine, dried over anhydrous magnesium sulfate, and filtered. The residue obtained by concentrating the filtrate under reduced pressure was subjected to silica gel column chromatography (hexane-ethyl acetate 9:1) to give 1.12 g of 3-benzyl-2-ethyl-2-hydroxysuccinic acid diethyl ester as oil in the form of a diastereomer mixture (yield: 73%).

b) The 3-Benzyl-2-ethyl-2-hydroxysuccinic acid diethyl ester thus obtained was dissolved in 1,4-dioxane (5 mL), added with water (5 mL) and 5 M sodium hydroxide aqueous solution (15 mL), and stirred at 100° C. for 15 h. The reaction mixture was cooled to room temperature, adjusted to pH 1 with 1 M hydrochloric acid, and extracted with ethyl acetate. The organic layer having been washed with 1 M hydrochloric acid and brine was dried over anhydrous magnesium sulfate and then filtered. The organic layer was concentrated under reduced pressure to give 1.0 g (quantitative) of 3-benzyl-2-ethyl-2-hydroxysuccinic acid as a solid.

c) The 3-Benzyl-2-ethyl-2-hydroxysuccinic acid obtained was dissolved in acetic anhydride (35 mL) and stirred at 110° C. for 15 h. The residue obtained by evaporating the acetic anhydride of the reaction mixture under reduced pressure was subjected to silica gel column chromatography (hexane-toluene-ethyl acetate 8:3:1) to give 619 mg of the title compound as oil (yield: 79%).
$^1$H NMR (CDCl$_3$) δ 1.13 (t, J=7.8 Hz, 3H), 2.49 (q, J=7.8 Hz, 2H), 3.79 (s, 2H), 7.18-7.49 (m, 5H); MS (EI) m/z 216 (M$^+$).

Example 11

2-benzyl-3-ethylmaleic acid disodium

To a solution of 2-benzyl-3-ethylmaleic anhydride (619 mg, 2.86 mmol) in 1,4-dioxane (3.0 mL) was added 1 M aqueous sodium hydroxide solution (5.73 mL, 5.73 mmol) at room temperature, and the mixture was stirred for 10 min. The reaction mixture was concentrated under reduced pressure, and the residue obtained was dried in vacuum to give 800 mg (quantitative) of the title compound as a colorless solid.
$^1$H NMR (D$_2$O) δ 0.85 (t, J=7.5 Hz, 3H), 2.20 (q, J=7.5 Hz, 2H), 3.79 (s, 2H), 7.08-7.31 (m, 5H); MS (FAB+) m/z 279 [(M+H)$^+$].

Example 12

Synthesis Example

Ethyl 3-(4-t-butyldimethylsilyloxyphenyl)propionate

To a solution of ethyl 3-(4-hydroxyphenyl)propionate (940 mg, 4.84 mmol) in anhydrous dimethylformamide (9.4 mL) were added t-butyldimethylsilyl chloride (1.0 g, 6.6 mmol) and imidazole (490 mg, 1.5 mmol) at room temperature, and the mixture was left standing at the same temperature for 14 h. The reaction mixture was directly concentrated, and subjected to silica gel column chromatography (hexane-ethyl acetate 25:1→20:1) to give 1.49 g (quantitative) of the title compound as a solid.
$^1$H NMR (CDCl$_3$) δ 0.18 (s, 6H), 0.97 (s, 9H), 1.23 (t, J=7.0 Hz, 3H), 2.57 (t, J=7.3 Hz, 2H), 2.88 (t, J=7.3 Hz, 2H), 4.12 (q, J=7.0 Hz, 2H), 6.57 (m, 2H), 6.87 (m, 2H).

Example 13

Synthesis Example

2-(4-Acetoxybenzyl)-3-ethylmaleic anhydride a) Under the atmosphere of argon, to a solution of diisopropylamine (572 mg, 5.65 mmol) in anhydrous tetrahydrofuran (7 mL) was added a 1.54 M n-butyl lithium-hexane solution (3.5 mL, 5.4 mmol) with stirring under ice cooling, and the mixture was stirred at 0° C. for 10 min and then at −78° C. for 5 min. To the mixture, a solution of ethyl 3-(4-t-butyldimethylsilyloxyphenyl)propionate (1.47 g, 4.78 mmol) in anhydrous tetrahydrofuran (7 mL) was added dropwise at the same temperature over 6 min, and the reaction mixture was further stirred for 20 min. The cold solution of the enolate thus prepared above was added dropwise via a cannula into a solution of ethyl 2-ketobutyrate (518 mg, 3.98 mmol) in anhydrous tetrahydrofuran (5 mL) having been cooled to −78° C. After stirring at −78° C. for 1 h, the reaction mixture was quenched and adjusted to pH 4 with acetic acid, and the temperature was raised to room temperature. The reaction solvent was evaporated under reduced pressure, and the residue was diluted with ethyl acetate and water to separate the phases. The organic layer having been washed with brine was concentrated under reduced pressure. The residue obtained was subjected to silica gel column chromatography (hexane-ethyl acetate 10:1→5:1) to give diethyl 3-(4-t-butyldimethylsilyloxybenzyl)-2-ethyl-2-hydroxysuccinate as oil in amounts of 433 mg (low polar diastereomer, yield: 25%) and 290 mg (high polar diastereomer, yield: 17%), respectively.

b) To a solution of diethyl 3-(4-t-butyldimethylsilyloxybenzyl)-2-ethyl-2-hydroxysuccinate 425 mg (0.968 mmol) in 1,4-dioxane (3.9 mL) was added 1 M lithium hydroxide aqueous solution (3.9 mL, 3.9 mmol) at room temperature, and the mixture was stirred at 60° C. for 22 h. The reaction mixture was adjusted to pH 1 with 1 M hydrochloric acid with stirring under ice cooling. The solvent was evaporated under reduced pressure, and the residue thus obtained was dissolved in ethyl acetate, and washed with water and brine. The organic layer was concentrated under reduced pressure and dried in vacuum to give 343 mg (crude) of 3-(4-t-butyldimethylsilyloxybenzyl)-2-ethyl-2-hydroxysuccinic acid as a solid.

c) To the crude 3-(4-t-butyldimethylsilyloxybenzyl)-2-ethyl-2-hydroxysuccinic acid thus obtained was added acetic anhydride (5 mL), and the mixture was stirred at 115° C. for 3 h. The acetic anhydride was evaporated under reduced pressure, and the residue thus obtained was subjected to silica gel column chromatography (toluene-ethyl acetate 19:1→16:1) to give the title compound as oil in an amount of 210 mg (2 step yield: 79%).

$^1$H NMR (CDCl$_3$) δ 1.16 (t, J=7.6 Hz, 3H), 2.30 (s, 3H), 2.51 (q, J=7.6 Hz, 2H), 3.78 (s, 2H), 7.05 (m, 2H), 7.50 (m, 2H).

Example 14

3-Ethyl-2-(4-hydroxybenzyl)maleic acid disodium

In the same manner as Example 11, the title compound was obtained from 2-(4-acetoxybenzyl)-3-ethylmaleic anhydride as a solid (quantitative).

$^1$H NMR (D$_2$O) δ 0.83 (t, J=7.6 Hz, 3H), 2.18 (q, J=7.6 Hz, 2H), 3.40 (s, 2H), 6.66 (m, 2H), 6.99 (m, 2H); MS (FAB+) m/z 295 [(M+H)$^+$].

Example 15

Synthesis Example 2,3-Dibenzylmaleic anhydride a) To a solution of (2S,3S)-2,3-dibenzylsuccinic acid (252 mg, 0.845 mmol) in anhydrous tetrahydrofuran (2.5 mL) were added N-methylmorpholine (90 mg, 0.89 mmol) and ethyl chloroformate (97 mg, 0.89 mmol) with stirring under ice cooling, and the mixture was stirred at room temperature for 20 min. The reaction mixture was directly concentrated to dryness under reduced pressure to give 340 mg of (2S,3S)-2,3-dibenzylsuccinic anhydride(crude) as a solid.

b) To the suspension of (2S,3S)-2,3-dibenzylsuccinic anhydride thus obtained in anhydrous toluene (3.5 mL) were added triethylamine (361 mg, 2.54 mmol) and trimethylsilyltrifluoromethanesulfonic acid (565 mg, 2.54 mmol) with stirring under ice cooling, and the mixture was stirred at 90° C. for 2 h. To the reaction mixture with stirring under ice cooling was added dropwise a solution of tetrabutylammonium bromide (2.7 mg, 0.00845 mmol) in dichloromethane (3 mL) and bromine (140 mg, 0.876 mmol), and the reaction mixture was stirred at the same temperature for 30 min. The reaction mixture was directly concentrated under reduced pressure and the residue thus obtained was subjected to silica gel column chromatography (hexane-ethyl acetate 8:1) to give 59 mg of the title compound as a solid (2 step yield: 25%).

$^1$H NMR (CDCl$_3$) δ 3.80 (s, 4H), 7.14 (m, 4H), 7.28 (m, 6H).

Example 16

2,3-Dibenzylmaleic acid disodium

In the same manner as Example 11, the title compound was obtained from 2,3-dibenzylmaleic anhydride as a solid (quantitative).

$^1$H NMR (D$_2$O) δ 3.59 (s, 4H), 7.10-7.21 (m, 10H); MS (FAB+) m/z 341 [(M+H)$^+$].

Example 17

Synthesis Example

2-Benzyl-3-phenethylmaleic anhydride a) Diisopropylamine (1.44 g, 14.3 mmol) was dissolved in anhydrous tetrahydrofuran (20 mL) under the atmosphere of argon, and a 1.54 M n-butyl lithium-hexane solution (8.8 mL, 13.6 mmol) was added with stirring under ice cooling. The mixture was stirred at 0° C. for 10 min, and then at −78° C. for 5 min. To the mixture, a solution of ethyl 3-phenylpropionate (2.14 g, 12.0 mmol) in anhydrous tetrahydrofuran (2 mL) was added at the same temperature over 6 min, and the reaction mixture was further stirred for 20 min. The cold solution of the enolate thus prepared above was added dropwise via a cannula into a solution of ethyl 2-oxo-4-phenylbutyrate (2.05 g, 10 mmol) in anhydrous tetrahydrofuran (10 mL) having been cooled to −78° C. After stirring at −78° C. for 1 h, the reaction mixture was adjusted to pH 4 with acetic acid, and the temperature was raised to room temperature. The reaction solvent was evaporated under reduced pressure, and the residue was diluted with ethyl acetate and water to separate the phases. The organic layer having been washed with brine was concentrated under reduced pressure. The residue obtained was subjected to silica gel column chromatography (hexane-ethyl acetate 10:1) to give diethyl 3-benzyl-2-phenethyl-2-hydroxysuccinate as oil in amounts of 806 mg (low polar diastereomer, yield: 21%) and 412 mg (high polar diastereomer, yield: 13%), respectively.

b) To a diethyl 3-benzyl-2-hydroxy-2-phenethylsuccinate (806 mg, 2.1 mmol) in 1,4-dioxane (8.0 mL) was added 1 M aqueous lithium hydroxide solution (8.4 mL, 8.4 mmol) at room temperature, and the mixture was stirred at 60° C. for 48 h. The reaction mixture was quenched and adjusted to pH 1 with 1 M hydrochloric acid with stirring under ice cooling. The solvent was evaporated under reduced pressure, and the residue thus obtained was dissolved in ethyl acetate, and washed with water and brine. The organic layer was concentrated under reduced pressure and dried in vacuum to give 651 mg (crude) of 3-benzyl-2-hydroxy-2-phenethylsuccinic acid c) To the crude 3-benzyl-2-hydroxy-2-phenethylsuccinic acid obtained was added acetic anhydride (2.5 mL), and the mixture was stirred at 115° C. for 3 h. The acetic anhydride was evaporated under reduced pressure, and the residue thus obtained was subjected to silica gel column chromatography (hexane-ethyl acetate 10:1) to give 180 mg of the title compound as a solid (2 step yield: 81%).

$^1$H NMR (CDCl$_3$) δ 2.73 (m, 2H), 2.82 (m, 2H), 3.51 (s, 2H), 7.09 (m, 4H), 7.22-7.32 (m, 6H).

Example 18

2-Benzyl-3-phenethylmaleic acid disodium

In the same manner as Example 11, the title compound was obtained from 2-benzyl-3-phenethylmaleic anhydride as a solid (quantitative).

$^1$H NMR (D$_2$O) δ 2.44 (m, 2H), 2.53 (m, 2H), 3.44 (s, 2H), 7.07-7.23 (m, 10H); MS (FAB+) m/z 355 [(M+H)$^+$].

Example 19

2,3-Diphenethylmaleic acid diethyl ester

In the same manner as Example 3, the title compound was obtained from ethyl 2-bromo-4-phenylbutyrate as a solid (yield: 70%).

$^1$H NMR (CDCl$_3$) δ 1.32 (t, J=7.2 Hz, 6H), 2.51-2.67 (m, 8H), 4.22 (q, J=7.2 Hz, 4H), 7.14-7.30 (m, 10H).

Example 20

2,3-Diphenethylmaleic acid disodium

In the same manner as Example 2, the title compound was obtained from 2,3-diphenethylmaleic acid diethyl ester as a solid (quantitative).

$^1$H NMR (D$_2$O) δ 2.30 (m, 4H), 2.49 (m, 4H), 7.08-7.23 (m, 10H); MS (FAB+) m/z 369 [(M+H)$^+$].

Example 21

Synthesis Example

2-Isopropyl-3-methylmaleic anhydride a) To anhydrous tetrahydrofuran (5 mL) was added diisopropylamine (759 mg, 7.5 mmol) under nitrogen stream, and the mixture was cooled to −78° C. To the solution was added a 1.58 M n-butyl lithium-hexane solution (4.3 mL, 6.8 mmol), and the mixture was stirred at −78° C. for 5 min, and then at 0° C. for 15 min. The solution of lithium diisopropylamide tetrahydrofuran was cooled to −78° C., and a solution of benzyl propionate (821 mg, 5.0 mmol) in anhydrous tetrahydrofuran (10 mL) was added dropwise over 1 h, and the reaction mixture was further stirred at −78° C. for 1 h. The enolate thus prepared was added via a cannula to a solution of benzyl 3-methyl-2-ketobutyrate (1.24 g, 6.0 mmol) in anhydrous tetrahydrofuran (5 mL) having been cooled to −78° C. After stirring at −78° C. for 2 h, the reaction mixture was diluted with a 10% aqueous citric acid solution, and extracted with ethyl acetate. The organic layer was washed with 1 M hydrochloric acid, saturated aqueous sodium hydrogen carbonate and brine, dried over anhydrous magnesium sulfate, and filtered. The solvent was evaporated under reduced pressure, and the residue thus obtained was subjected to silica gel column chromatography (hexane-ethyl acetate 9:1) to give 1.22 g of dibenzyl 2-isopropyl-2-hydroxy-3-methylsuccinate as oil (yield: 66%) in the form of a diastereomer mixture.

b) The dibenzyl 2-isopropyl-2-hydroxy-3-methylsuccinate thus obtained was dissolved in tetrahydrofuran (25 mL), and the solution was stirred in the presence of 10% palladium/carbon (120 mg) under hydrogen stream at room temperature for 15 h. The catalyst was removed by filtration, and the filtrate was concentrated under reduced pressure to give 748 mg of 2-hydroxy-2-isopropyl-3-methylsuccinic acid as oil (quantitative).

c) The 2-hydroxy-2-isopropyl-3-methylsuccinic acid thus obtained was dissolved in acetic anhydride (30 mL), and stirred at 110° C. for 15 h. The acetic anhydride was evaporated under reduced pressure, and the residue thus obtained was subjected to silica gel column chromatography (hexane-ethyl acetate 19:1) to give 203 mg of the title compound as oil (yield: 40%).

$^1$H (CDCl$_3$) δ 1.30 (d, J=7.1 Hz, 6H), 2.10 (s, 3H), 2.92-3.03 (m, 1H); MS (EI) m/z 154 (M$^+$).

Example 22

2-isopropyl-3-methylmaleic acid disodium

In the same manner as Example 11, the title compound was obtained from 2-isopropyl-3-methylmaleic anhydride as a solid (quantitative).

$^1$H NMR (D$_2$O) δ 0.91 (d, J=6.9 Hz, 6H), 1.63 (s, 3H), 2.55-2.65 (m, 1H); MS (FAB+) m/z 217 [(M+H)$^+$].

Example 23

Synthesis Example

3-Ethyl-2-isopropylmaleic anhydride

In the same manner as Example 10, the title compound was obtained from ethyl butyrate and ethyl 3-methyl-2-ketobutyrate as a oil (yield: 50%).

$^1$H NMR (CDCl$_3$) δ 1.15 (t, J=7.6 Hz, 3H), 1.30 (d, J=6.8 Hz, 6H), 2.54 (q, J=7.6 Hz, 2H), 2.93-3.04 (m, 1H); MS (EI) m/z 169 [(M+H)$^+$].

Example 24

3-ethyl-2-isopropylmaleic acid disodium

In the same manner as Example 11, the title compound was obtained from 3-ethyl-2-isopropylmaleic anhydride as a solid (quantitative).

$^1$H NMR (D$_2$O) δ 0.87 (t, J=7.5 Hz, 3H), 0.91 (d, J=6.2 Hz, 6H), 2.09 (q, J=7.5 Hz, 2H), 2.57-2.68 (m, 1H); MS (FAB+) m/z 231 [(M+H)$^+$].

Example 25

Synthesis Example 2,3-Diisopropylmaleic anhydride

In the same manner as Example 21, the title compound was obtained from benzyl 3-methylbutyrate and benzyl 3-methyl-2-ketobutyrate as a solid (yield: 68%).

NMR (CDCl₃) δ 1.30 (d, J=6.9 Hz, 12H), 2.98-3.09 (m, 2H); MS (FAB+) m/z 183 [(M+H)⁺].

Example 26

2,3-Diisopropylmaleic acid disodium

In the same manner as Example 11, the title compound was obtained from 2,3-diisopropylmaleic anhydride as a solid (quantitative).
¹H NMR (D₂O) δ 0.68 (d, J=6.8 Hz, 12H), 2.32-2.42 (m, 2H); MS (FAB+) m/z 245 [(M+H)⁺].

Example 27

Synthesis Example

3-Benzyl-2-isopropylmaleic anhydride

In the same manner as Example 10, the title compound was obtained from ethyl phenylpropionate and ethyl 3-methyl-2-ketobutyrate as oil (yield: 27%).
¹H NMR (CDCl₃) δ 1.27 (d, J=6.9 Hz, 6H), 3.00-3.10 (m, 1H), 3.80 (s, 2H), 7.20-7.35 (m, 5H); MS (EI) m/z 231 [(M+H)⁺].

Example 28

3-Benzyl-2-isopropylmaleic acid disodium

In the same manner as Example 11, the title compound was obtained from 3-benzyl-2-isopropylmaleic anhydride as a solid (quantitative).
¹H NMR (D₂O) δ 0.91 (d, J=7.0 Hz, 6H), 2.65-2.76 (m, 1H), 3.53 (s, 2H), 7.06-7.23 (m, 5H); MS (FAB+) m/z 293 [(M+H)⁺].

Example 29

Synthesis Example 2-isopropyl-3-(2-methylphenyl)methylmaleic anhydride

In the same manner as Example 21, the title compound was obtained from benzyl 3-(2-methyl)phenylpropionate and benzyl 3-methyl-2-ketobutyrate as oil (yield: 60%).
¹H NMR (CDCl₃) δ 1.22 (d, J=6.1 Hz, 6H), 2.35 (s, 3H), 2.83-2.94 (m, 1H), 3.79 (s, 2H), 7.00 (d, J=6.9 Hz, 1H), 7.12-7.20 (m, 3H); MS (EI) m/z 244 (M⁺).

Example 30

2-Isopropyl-3-(2-methylphenyl)methylmaleic acid disodium

In the same manner as Example 11, the title compound was obtained from 2-isopropyl-3-(2-methylphenyl)methylmaleic anhydride as a solid (quantitative).

¹H NMR (D₂O) δ 0.89 (d, J=7.1 Hz, 6H), 2.19 (s, 3H), 2.54-2.65 (m, 1H), 3.47 (s, 2H), 7.00-7.15 (m, 4H); MS (FAB+) m/z 307 [(M+H)⁺].

Example 31

Synthesis Example

2-Cyclopentyl-3-ethylmaleic anhydride

In the same manner as Example 21, the title compound was obtained from benzyl cyclopentylacetate and benzyl 2-ketobutyrate as oil (yield: 63%).
¹H NMR (CDCl₃) δ 1.18 (t, J=7.5 Hz, 3H), 1.65-1.95 (m, 8H), 2.49 (q, J=7.5 Hz, 2H), 2.92-3.03 (m, 1H); MS (EI) m/z 195 [(M+H)⁺].

Example 32

2-Cyclopentyl-3-ethylmaleic acid disodium

In the same manner as Example 11, the title compound was obtained from 2-cyclopentyl-3-ethylmaleic anhydride as a solid (quantitative).
¹H NMR (D₂O) δ 0.80 (t, J=7.3 Hz, 3H), 1.24-1.68 (m, 8H), 2.10 (q, J=7.3 Hz, 2H), 2.57-2.67 (m, 1H); MS (FAB+) m/z 257 [(M+H)⁺].

Example 33

Synthesis Example

2-Cyclopentyl-3-isopropylmaleic anhydride

In the same manner as Example 21, the title compound was obtained from benzyl cyclopentylacetate and benzyl 3-methyl-2-ketobutyrate as oil (yield: 79%).
¹H NMR (CDCl₃) δ 1.30 (d, J=7.1 Hz, 6H), 1.65-1.95 (m, 8H), 2.96-3.08 (m, 2H); MS (EI) m/z 208 (M⁺).

Example 34

2-Cyclopentyl-3-isopropylmaleic acid disodium

In the same manner as Example 11, the title compound was obtained from 2-cyclopentyl-3-isopropylmaleic anhydride as a solid (quantitative).
¹H NMR (D₂O) δ 0.92 (d, J=6.8 Hz, 6H), 1.26-1.70 (m, 8H), 2.56-2.68 (m, 2H); MS (FAB+) m/z 271 [(M+H)⁺].

Example 35

Synthesis Example

Benzyl 2-keto-2-cyclopentylacetate a) A 0.5 M potassium bistrimethylsilylamide-toluene solution (67.2 mL, 33.6 mmol) was added to anhydrous tetrahydrofuran (30 mL), and the mixture was cooled to −78° C. under nitrogen stream. To this mixture was added dropwise a solution of benzyl cyclopentylacetate (6.11 g, 28 mmol) in anhydrous tetrahydrofuran (30 mL) over 1 h. After the mixture was stirred at −78° C. for 30 min, a solution of Davis oxaziridine reagent (8.78 g, 33.6 mmol) in anhydrous tetrahydrofuran (30 mL) was added dropwise over 1 h. The reaction mixture, which had been stirred at −78° C. for 1 h, was diluted with a saturated aqueous ammonium chloride solution and extracted with diethyl ether. The organic layer was washed with water and brine, dried over anhydrous magnesium sulfate, filtered, and the organic solvent in the filtrate was evaporated under reduced pressure. The residue was subjected to silica gel column chromatography (hexane-ethyl acetate 9:1) to give 6.157 g of benzyl 2-cyclopentyl-2-hydroxyacetate (yield: 94%).

$^1$H NMR (CDCl$_3$) δ 1.36-1.74 (m, 8H), 2.19-2.3 (m, 1H), 2.70 (d, J=6.5 Hz, 1H), 4.17 (dd, J=4.9, 6.5 Hz, 1H), 5.19 (d, J=12.2 Hz, 1H), 5.23 (d, J=12.2 Hz, 1H), 7.30-7.45 (m, 5H).

b) To a solution of benzyl 2-cyclopentyl-2-hydroxyacetate (1.76 g, 7.5 mmol) in dichloromethane (30 mL) was added Dess-Martin reagent (5 g, 11.8 mmol), and the mixture was stirred at room temperature for 15 h. The reaction mixture was diluted with 10% sodium thiosulfate, and extracted with diethyl ether. The organic layer was washed with water, saturated aqueous sodium hydrogen carbonate, and brine, dried over anhydrous magnesium sulfate, filtered, and the organic solvent in the filtrate was evaporated under reduced pressure. The residue was subjected to silica gel column chromatography (hexane-ethyl acetate 9:1) to give 1.383 g of the title compound as oil (yield: 79%).

$^1$H NMR (CDCl$_3$) δ 1.58-1.92 (m, 8H), 3.44-3.53 (m, 1H), 5.28 (s, 2H), 7.34-7.42 (m, 5H); MS (EI) m/z 232 (M$^+$).

Example 36

Synthesis Example

3-Benzyl-2-cyclopentylmaleic anhydride

In the same manner as Example 21, the title compound was obtained from benzyl 3-phenylpropionate and benzyl 2-cyclopentyl-2-ketoacetate as oil (yield: 42%).

$^1$H NMR (CDCl$_3$) δ 1.60-1.95 (m, 8H), 3.00-3.10 (m, 1H), 3.80 (s, 2H), 7.18-7.34 (m, 5H); MS (EI) m/z 256 (M$^+$).

Example 37

3-benzyl-2-cyclopentylmaleic acid disodium

In the same manner as Example 11, the title compound was obtained from 3-benzyl-2-cyclopentylmaleic anhydride as a solid (quantitative).

$^1$H NMR (D$_2$O) δ 1.28-1.66 (m, 8H), 2.64-2.74 (m, 1H), 3.54 (s, 2H), 7.06-7.22 (m, 5H); MS (FAB+) m/z 319 [(M+H)$^+$].

Example 38

Synthesis Example 2,3-Dicyclopentylmaleic anhydride

In the same manner as Example 21, the title compound was obtained from benzyl cyclopentylacetate and benzyl 2-cyclopentyl-2-ketoacetate as a solid (yield: 60%).

$^1$H NMR (CDCl$_3$) δ 1.60-1.90 (m, 16H), 2.97-3.07 (m, 2H); MS (EI) m/z 234 (M$^+$).

Example 39

2,3-Dicyclopentylmaleic acid disodium

In the same manner as Example 11, the title compound was obtained from 2,3-dicyclopentylmaleic anhydride as a solid (quantitative).

$^1$H NMR (D$_2$O) δ 1.26-1.68 (m, 16H), 2.57-2.67 (m, 2H); MS (FAB+) m/z 297 [(M+H)$^+$].

Example 40

Synthesis Example 2-(2,3-Dihydro-1H-inden-2-yl)-3-isopropylmaleic anhydride

In the same manner as Example 21, the title compound was obtained from benzyl 2-(2,3-dihydro-1H-inden-2-yl)acetate and benzyl 3-methyl-2-ketobutyrate as oil (yield: 62%).

$^1$H NMR (CDCl$_3$) δ 1.30 (d, J=7.1 Hz, 6H), 2.98-3.08 (m, 1H), 3.14 (dd, J=8.6, 15.1 Hz, 2H), 3.33 (dd, J=10.0, 15.1 Hz, 2H), 3.65-3.75 (m, 1H), 7.18-7.26 (m, 4H); MS (EI) m/z 256 (M$^+$).

Example 41

2-(2,3-Dihydro-1H-inden-2-yl)-3-isopropylmaleic acid disodium

In the same manner as Example 11, the title compound was obtained from 2-(2,3-dihydro-1H-inden-2-yl)-3-isopropylmaleic anhydride as a solid (quantitative).

$^1$H NMR (D$_2$O) δ 0.95 (d, J=7.1 Hz, 6H), 2.62-2.73 (m, 1H), 2.84-2.96 (m, 4H), 3.26-3.37 (m, 1H), 7.02-7.07 (m, 2H), 7.12-7.16 (m, 2H); MS (FAB+) m/z 319 [(M+H)$^+$].

Example 42

Synthesis Example

2-Cyclohexyl-3-isopropylmaleic anhydride

In the same manner as Example 21, the title compound was obtained from benzyl cyclohexylacetate and benzyl 3-methyl-2-ketobutyrate as oil (yield: 57%).

$^1$H NMR (CDCl$_3$) δ 1.30 (d, J=7.0 Hz, 6H), 1.60-1.90 (m, 10H), 2.62-2.72 (m, 1H), 3.00-3.12 (m, 1H); MS (EI) m/z 222 (M$^+$).

Example 43

2-Cyclohexyl-3-isopropylmaleic acid disodium

In the same manner as Example 11, the title compound was obtained from 2-cyclohexyl-3-isopropylmaleic anhydride as a solid (quantitative).

$^1$H NMR (D$_2$O) δ 0.91 (d, J=6.8 Hz, 6H), 0.96-1.28 (m, 5H), 1.47-1.59 (m, 5H), 2.15-2.26 (m, 1H), 2.56-2.64 (m, 1H); MS (FAB+) m/z 285 [(M+H)$^+$].

Example 44

Synthesis Example

Trans-4-benzyloxycarbonylmethyl-1-t-butyldimethylsilyloxycyclohexane and cis-4-benzyloxycarbonylmethyl-1-t-butyldimethylsilyloxycyclohexane a) To a solution of 1,4-cyclohexanedionemonoethyleneacetal (5.02 g, 32.1 mmol) in toluene (150 mL) were added benzyl (triphenylphospholanylidene)acetate (23.7 g, 57.8 mmol) and benzoic acid (832.5 mg, 6.82 mmol) at room temperature, and the mixture was vigorously stirred at 95° C. for 2 days. The reaction mixture was directly concentrated under reduced pressure, and the residue obtained was diluted with hexane (300 mL) and diethyl ether (150 mL), and vigorously stirred for 10 min. The reaction mixture was filtered, and the residue obtained by concentrating the filtrate under reduced pressure was subjected to silica gel column chromatography (hexane-ethyl acetate 6:1→4:1) to give 8.53 g of 4-benzyloxycarbonylmethylidenecyclohexane-ethylene acetal as oil (yield: 92%).

b) To a solution of 4-Benzyloxycarbonylmethylidenecyclohexane-ethylene acetal (8.19 g, 28.4 mmol) in methanol were added diphenyl sulfide (52 mg, 0.28 mmol) and 10% palladium/carbon (1.74 g), and the mixture was vigorously stirred under hydrogen atmosphere at room temperature for 40 h. The reaction mixture was filtered, and the residue obtained by concentrating the filtrate under reduced pressure was subjected to silica gel column chromatography (hexane-ethyl acetate 3:1) to give 7.62 g of 4-benzyloxycarbonylmethylcyclohexanone ethylene acetal as oil (yield: 92%).

c) To a solution of 4-benzyloxycarbonylmethylcyclohexanone ethylene acetal (7.62 g, 26.2 mmol) in acetone (235 mL)-water (10 mL) was added p-toluenesulfonic acid monohydrate (221 mg, 1.16 mmol), and the mixture was stirred at 55° C. for 10 h. The reaction mixture was adjusted to pH 5 with sodium hydrogen carbonate with stirring under ice cooling, and concentrated under reduced pressure. The residue obtained by azeotropic distillation with the addition of toluene was subjected to silica gel column chromatography (hexane-ethyl acetate 4:1) to give 5.57 g of benzyl 2-(4-oxocyclohexyl)acetate as oil (yield: 86%).

d) To a solution of benzyl 2-(4-oxocyclohexyl)acetate (2.64 g, 10.7 mmol) in methanol (50 mL) was added sodium borohydride (393 mg, 10.4 mmol) with stirring under ice cooling. After stirring at the same temperature for 2 h, the reaction mixture was adjusted to pH 4 with acetic acid (1 mL). The reaction mixture was concentrated under reduced pressure, and the residue thus obtained was diluted with ethyl acetate and water to separate the layers. The aqueous layer was extracted again with ethyl acetate, and the combined organic layer was concentrated under reduced pressure, and the residue was subjected to silica gel column chromatography (hexane-ethyl acetate 3:1→2:1→1:1) to give 2.20 g of trans-4-benzyloxycarbonylmethyl-1-hydroxycyclohexane (yield: 82%) and 540 mg of cis-4-benzyloxycarbonylmethyl-1-hydroxycyclohexane (yield: 20%) as oil.

e) To a solution of trans-4-benzyloxycarbonylmethyl-1-hydroxycyclohexane (2.20 g, 8.86 mmol) in dimethylformamide (31 mL) were added imidazole (953 mg, 14.0 mmol) and t-butyldimethylsilyl chloride (1.60 g, 10.6 mmol) at room temperature, and the mixture was stirred at 60° C. for 3 h. The reaction mixture was diluted with water (70 mL) and hexane (200 mL) with stirring under ice cooling to separate the phases. The aqueous layer was extracted again with hexane, and the combined organic layer was concentrated under reduced pressure and the residue thus obtained was subjected to silica gel column chromatography (hexane-ethyl acetate 50:1) to give 2.96 g of trans-4-benzyloxycarbonylmethyl-1-t-butyldimethylsilyloxycyclo hexane as oil (yield: 92%).

$^1$H NMR (CDCl$_3$) δ 0.04 (s, 6H), 0.89 (s, 9H), 1.01 (m, 2H), 1.31 (m, 2H), 1.57-1.84 (m, 5H), 2.23 (d, J=6.6 Hz, 2H), 3.50 (m, 1H), 5.11 (s, 2H), 7.30-7.38 (m, 5H).

f) In the same manner as the step e), cis-4-benzyloxycarbonylmethyl-1-t-butyldimethylsilyloxycyclohexane as oil (yield: 89%) from cis-4-benzyloxycarbonylmethyl-1-hydroxycyclohexane.

$^1$H NMR (CDCl$_3$) δ 0.02 (s, 6H), 0.87 (s, 9H), 1.44-1.49 (m, 6H), 1.52-1.62 (m, 2H), 1.85 (m, 1H), 2.28 (d, J=7.3 Hz, 2H), 3.92 (m, 1H), 5.11 (s, 2H), 7.30-7.38 (m, 5H).

Example 45

Synthesis Example 2-(Trans-4-hydroxycyclohexyl)-3-isopropylmaleic anhydride a) To a solution of diisopropylamine (418 mg, 4.15 mmol) in anhydrous tetrahydrofuran (6 mL) under the atmosphere of argon was added a 1.58 M n-butyl lithium-hexane solution (2.5 mL, 5.4 mmol) with stirring under ice cooling, and the mixture was stirred at 0° C. for 10 min, and then at −78° C. for 5 min. A solution of trans-4-benzyloxycarbonylmethyl-1-t-butyldimethylsilyloxycyclohexan (1.36 g, 3.76 mmol) in anhydrous tetrahydrofuran (7 mL) was added dropwise at the same temperature over 7 min, and the reaction mixture was further stirred for 15 min. The cold enolate solution thus prepared was added dropwise via canula to a solution of benzyl 3-methyl-2-ketobutyrate (776 mg, 3.76 mmol) in anhydrous tetrahydrofuran (4 mL) having been cooled to −78° C. After stirring at −78° C. for 1 h, the reaction mixture was adjusted to pH 4 with acetic acid, and the temperature was raised to room temperature. The reaction solvent was evaporated under reduced pressure, and the residue was diluted with ethyl acetate and water to separate the phases for extraction. The aqueous layer was extracted again with ethyl acetate, and the combined organic layer was concentrated under reduced pressure and the residue thus obtained was subjected to silica gel column chromatography (hexane-ethyl acetate 20:1) to give dibenzyl 3-(trans-4-t-butyldimethylsilyloxycyclohexyl)-2-hydroxy-2-isopropylsuccinate as oil in amounts of 629 mg (low polar diastereomer, yield: 29%) and 801 mg (high polar diastereomer, yield: 37%), respectively.

b) To a solution of dibenzyl 3-(trans-4-t-butyldimethylsilyloxycyclohexyl)-2-hydroxy-2-isopropylsuccinate (801 mg, 1.41 mmol) in ethanol (13 mL) was added 10% palladium/carbon (251 mg, 50% water containing product), and the mixture was stirred under hydrogen stream at room temperature for 20 h. The catalyst was removed by filtration, and the filtrate was concentrated to dryness under reduced pressure to give 514 mg of 3-(trans-4-t-butyldimethylsilyloxy)-2-hydroxy-2-isopropylsuccinic acid as oil (yield: 94%).

c) 3-(Trans-4-t-butyldimethylsilyloxycyclohexyl)-2-hydroxy-2-isopropylsuccinic acid (510 mg, 1.31 mmol) was dissolved in acetic anhydride (5.5 mL), and the solution was stirred at 120° C. for 18 h. The acetic anhydride was evaporated under reduced pressure and the residue thus obtained was subjected to silica gel column chromatography (hexane-ethyl acetate 50:1) to give 293 mg of 2-(trans-4-t-butyldimethylsilyloxycyclohexyl)-3-isopropylmaleic anhydride as oil (yield: 63%).

d) To a solution of 2-(trans-4-t-butyldimethylsilyloxycyclohexyl)-3-isopropylmaleic anhydride (263 mg, 0.745 mmol) in ethanol (7 mL) was added concentrated.

hydrochloric acid (83 mg, 0.84 mmol), and the mixture was left standing at 50° C. for 30 min. The reaction mixture was directly concentrated, and the residue thus obtained was subjected to silica gel column chromatography (hexane-ethyl acetate 1:1) to give 179 mg (quantitative) of the title compound as a solid.

$^1$H NMR (CDCl$_3$) δ 1.31 (d, J=6.8 Hz, 6H), 1.38 (m, 2H), 1.55 (br s, 1H), 1.70 (m, 2H), 1.93 (m, 2H), 2.11 (m, 2H), 2.63 (m, 1H), 3.03 (m, 1H), 3.71 (m, 1H).

Example 46

2-(trans-4-Hydroxycyclohexyl)-3-isopropylmaleic acid disodium

In the same manner as Example 11, the title compound was obtained from 2-(trans-4-hydroxycyclohexyl)-3-isopropylmaleic anhydride as a solid (quantitative).

$^1$H NMR (D$_2$O) δ 0.93 (d, J=7.1 Hz, 6H), 1.18 (m, 2H), 1.35 (m, 2H), 1.57 (m, 2H), 1.83 (m, 2H), 2.21 (m, 1H), 2.60 (septet, J=7.1 Hz, 1H), 3.46 (m, 1H); MS (FAB+) m/z 301 [(M+H)$^+$].

Example 47

Synthesis Example 2-(Cis-4-hydroxycyclohexyl)-3-isopropylmaleic anhydride

In the same manner as Example 45, the title compound was obtained from cis-4-benzyloxycarbonylmethyl-1-t-butyldimethylsilyloxycyclohexane as a solid (yield: 42%).

$^1$H NMR (CDCl$_3$) δ 1.31 (d, J=6.8 Hz, 6H), 1.40 (br s, 1H), 1.48 (m, 2H), 1.59 (m, 2H), 1.92 (m, 2H), 2.20 (m, 2H), 2.70 (m, 1H), 3.11 (septet, J=6.8 Hz, 1H), 4.15 (m, 1H).

Example 48

2-(cis-4-Hydroxycyclohexyl)-3-isopropylmaleic acid disodium

In the same manner as Example 11, the title compound was obtained from 2-(cis-4-hydroxycyclohexyl)-3-isopropylmaleic anhydride as a solid (quantitative).

$^1$H NMR (D$_2$O) δ 0.92 (d, J=7.0 Hz, 6H), 1.32 (m, 2H), 1.42-1.60 (m, 4H), 1.65 (m, 2H), 2.28 (m, 1H), 2.61 (septet, J=7.0 Hz, 1H), 3.88 (m, 1H); MS (FAB+) m/z 301 [(M+H)$^+$].

Example 49

Synthesis Example

Benzyl 2-(tetrahydropyran-4-yl)acetate

To a solution of 2-(tetrahydropyran-4-yl)acetic acid (325 mg, 2.26 mmol) in anhydrous dichloromethane (10 mL) were added benzyl alcohol (439 mg, 2.94 mmol), 1-ethyl-3-(3-dimethylammoniumpropyl)carbodiimide hydrochloride (564 mg, 2.94 mmol) and triethylamine (297 mg, 2.94 mmol) at room temperature, and the mixture was stirred for 12 h. The reaction mixture was diluted with water (1 mL) to separate the phases, and the organic layer was further washed with water (1 mL) and brine (1 mL). The organic layer was concentrated under reduced pressure, and the residue thus obtained was subjected to silica gel column chromatography (hexane-ethyl acetate 7:1) to give 172 mg of the title compound as oil (yield: 32%).

$^1$H NMR (CDCl$_3$) δ 1.34 (m, 2H), 1.63 (m, 2H), 2.02 (m, 1H), 2.30 (d, J=7.1 Hz, 2H), 3.39 (m, 2H), 3.93 (m, 2H), 5.12 (s, 2H), 7.31-7.40 (m, 5H).

Example 50

Synthesis Example

3-Isopropyl-2-(tetrahydropyran-4-yl)maleic anhydride a) To a solution of diisopropylamine (122 mg, 1.21 mmol) in anhydrous tetrahydrofuran (2 mL) under the atmosphere of argon was added a 1.58 M n-butyl lithium-hexane solution (703 μL, 1.11 mmol) with stirring under ice cooling, and the mixture was stirred at 0° C. for 10 min and then at −78° C. for 5 min. A solution of benzyl 2-(tetrahydropyran-4-yl)acetate (250 mg, 1.07 mmol) in anhydrous tetrahydrofuran (1 mL) was added dropwise over 6 min at the same temperature, and the reaction mixture was further stirred for 15 min. The cold enolate solution thus prepared was added dropwise via a cannula to a solution of benzyl a solution of benzyl 3-methyl-2-ketobutyrate (191 mg, 0.928 mmol) in anhydrous tetrahydrofuran (1 mL) solution having been cooled to −78° C. After stirring at −78° C. for 1 h, the reaction mixture was adjusted to pH 4 with acetic acid and raised to room temperature. The reaction solvent was evaporated under reduced pressure, and the residue was diluted with ethyl acetate and water to separate the phases for extraction. The aqueous layer was extracted again with ethyl acetate, and the combined organic layer was concentrated under reduced pressure and the residue thus obtained was subjected to silica gel column chromatography (hexane-ethyl acetate 7:1) to give dibenzyl 2-hydroxy-2-isopropyl-3-(tetrahydro-2H-pyran-4-yl)succinate as oil in amounts of 115 mg (low polar diastereomer, yield: 29%) and 158 mg (high polar diastereomer, yield: 39%), respectively.

b) To a solution of dibenzyl 2-hydroxy-2-isopropyl-3-(tetrahydro-2H-pyran-4-yl)succinate (112 mg, 0.255 mmol) in ethanol (2.8 mL) was added 10% palladium/carbon (44 mg, 50% wet), and the mixture was stirred under hydrogen stream at room temperature for 2 h. The catalyst was removed by filtration, and the filtrate was concentrated under reduced pressure to give 72 mg (quantitative) of 2-hydroxy-2-isopropyl-3-(tetrahydropyran-4-yl)succinic acid as a foam.

c) 2-Hydroxy-2-isopropyl-3-(tetrahydropyran-4-yl)succinic acid (70 mg, 0.27 mmol) was dissolved in acetic anhydride (1 mL), and the solution was left standing at 120° C. for 10 h. The acetic anhydride was evaporated under reduced pressure and the residue thus obtained was subjected to silica gel column chromatography (hexane-ethyl acetate 3:1) to give 38 mg of the title compound as a solid (yield: 67%).

$^1$H NMR (CDCl$_3$) δ 1.32 (d, J=7.1 Hz, 6H), 1.54 (m, 2H), 2.16 (m, 2H), 2.94 (m, 1H), 3.10 (septet, J=7.1 Hz, 1H), 3.45 (m, 2H), 4.08 (m, 2H).

Example 51

3-Isopropyl-2-(tetrahydropyran-4-yl)maleic acid disodium

In the same manner as Example 11, the title compound was obtained from 3-isopropyl-2-(tetrahydropyran-4-yl)maleic anhydride as a solid (quantitative).

$^1$H NMR (D$_2$O) δ 0.93 (d, J=7.1 Hz, 6H), 1.42 (m, 2H), 1.61 (m, 2H), 2.55 (m, 1H), 2.62 (septet, J=7.1 Hz, 1H), 3.38 (m, 2H), 3.84 (m, 2H); MS (FAB+) m/z 287 [(M+H)$^+$].

Example 52

Synthesis Example

Benzyl 3-(3-pyridyl)propionate

To a suspension of 3-(3-pyridyl)propionic acid hydrochloride (1.51 g, 10.0 mmol) in benzyl alcohol (3.1 mL, 30 mmol) was added p-toluenesulfonic acid monohydrate (181.8 mg, 0.96 mmol), and the mixture was stirred at 130° C. for 20 h. The reaction mixture was diluted with ethyl acetate and a saturated aqueous sodium hydrogen carbonate solution was added to separate the phases. The aqueous layer was extracted again with ethyl acetate, and the combined organic layer was concentrated with reduced pressure. The residue was subjected to silica gel column chromatography (hexane-ethyl acetate 1:1→1:3) to give 1.69 g of the title compound as oil (yield: 70%).

Example 53

Synthesis Example

2-Isopropyl-3-[(pyridine-3-yl)methyl]maleic anhydride

In the same manner as Example 50, the title compound was obtained from benzyl 3-(3-pyridyl)propionate and benzyl 3-methyl-2-ketobutyrate as oil in an amount of 122 mg (yield: 38%).
$^1$H NMR (CDCl$_3$) δ 1.30 (d, J=6.8 Hz, 6H), 3.07 (septet, J=6.8 Hz, 1H), 3.82 (s, 2H), 7.28 (m, 1H), 7.59 (m, 1H), 8.53 (m, 2H).

Example 54

2-Isopropyl-3-[(pyridine-3-yl)methyl]maleic acid disodium

In the same manner as Example 11, the title compound was obtained from 2-isopropyl-3-[(pyridine-3-yl)methyl]maleic anhydride as a solid (quantitative).
$^1$H NMR (D$_2$O) δ 0.90 (d, J=6.8 Hz, 6H), 2.68 (septet, J=6.8 Hz, 1H), 3.55 (s, 2H), 7.24 (m, 1H), 7.62 (m, 1H), 8.19 (m, 1H), 8.26 (m, 1H); MS (FAB+) m/z 294 [(M+H)$^+$].

Example 55

Dimethyl 3-methyl-2-[(piperidin-1-yl)methyl]maleate a) To a solution of dimethyl 2,3-dimethylmaleate (500 mg, 2.90 mmol) in carbon tetrachloride (11 mL) were added N-bromosuccinimide (803 mg, 4.51 mmol) and 2,2'-azobisisobutyronitrile (3.2 mg, 0.019 mmol) at room temperature, and the mixture was heated under reflux with stirring for 4 h. The reaction mixture was directly filtrated, and the filtrate was washed with water and brine. The residue obtained by concentrating the organic layer under reduced pressure was subjected to silica gel column chromatography (hexane-ethyl acetate 20:1→8:1) to give 191 mg of dimethyl 2-bromomethyl-3-methylmaleate (yield: 26%).

b) To a solution of dimethyl 2-bromomethyl-3-methylmaleate (32 mg, 0.13 mmol) in anhydrous dimethylformamide (450 μL) was added piperidine (21 mg, 0.25 mmol) at room temperature, and the mixture was left standing at 50° C. for 4 h. The reaction mixture was directly concentrated under reduced pressure and the residue thus obtained was subjected to silica gel column chromatography (hexane-ethyl acetate 3:2) to give 3 mg of the title compound as oil (yield: 39%).
$^1$H NMR (CDCl$_3$) δ 1.39 (m, 2H), 1.51 (m, 4H), 1.99 (s, 3H), 2.37 (m, 4H), 3.23 (s, 2H), 3.75 (s, 3H), 3.76 (s, 3H).

Example 56

3-Methyl-2-[(piperidin-1-yl)methyl]maleic acid disodium

In the same manner as Example 2, the title compound was obtained from dimethyl 3-methyl-2-[(piperidin-1-yl)methyl]maleate as a solid (quantitative).
$^1$H NMR (D$_2$O) δ 1.26 (m, 2H), 1.38 (m, 4H), 1.74 (s, 3H), 2.33 (m, 4H), 3.10 (s, 2H); MS (FAB+) m/z 272 [(M+H)$^+$].

Example 57

2-[(4-Hydroxypiperidin-1-yl)methyl]-3-methylmaleic acid dimethyl ester

In the same manner as Example 55, the title compound was obtained from dimethyl 2,3-dimethylmaleate and 4-hydroxypiperidine as oil (yield: 43%).
$^1$H NMR (CDCl$_3$) δ 1.35 (br s, 1H), 1.55 (m, 2H), 1.84 (m, 2H), 1.99 (s, 3H), 2.17 (m, 2H), 2.74 (m, 2H), 3.27 (s, 2H), 3.68 (m, 1H), 3.76 (s, 3H), 3.78 (s, 3H).

Example 58

2-[(4-Hydroxypiperidin-1-yl)methyl]-3-methylmaleic acid disodium

In the same manner as Example 2, the title compound was obtained from 2-[(4-hydroxypiperidin-1-yl)methyl]-3-methylmaleic acid dimethyl ester as a solid (quantitative).
$^1$H NMR (D$_2$O) δ 1.34 (m, 2H,), 1.70 (m, 2H), 1.72 (s, 3H), 2.13 (m, 2H), 2.66 (m, 2H), 3.13 (s, 2H), 3.54 (m, 1H); MS (FAB+) m/z 288 [(M+H)$^+$].

Example 59

Synthesis Example

2-Hydroxymethyl-3-methylmaleic anhydride

To 2-bromomethyl-3-methylmaleic anhydride (1.25 g, 6.10 mmol) was added 5 M aqueous sodium hydroxide solution (4 mL) at room temperature, and the mixture was stirred for 12 h. The reaction mixture was adjusted to pH 1 with 5 M hydrochloric acid (5 mL), added with sodium chloride and extracted three times with ethyl acetate. The combined organic layer was concentrated under reduced pressure, and the residue thus obtained was subjected to silica gel column chromatography (hexane-ethyl acetate 2:1) to give 227 mg of the title compound as oil (yield: 26%).
$^1$H NMR (CDCl$_3$) δ 2.21 (t, J=1.1 Hz, 3H), 4.63 (q, J=1.1 Hz, 2H).

Example 60

2-Hydroxymethyl-3-methylmaleic acid disodium

In the same manner as Example 11, the title compound was obtained from 2-hydroxymethyl-3-methylmaleic anhydride as a solid (quantitative).

$^1$H NMR (D$_2$O) δ 1.75 (s, 3H), 4.65 (s, 2H); MS (FAB+) m/z 205 [(M+H)$^+$].

Example 61

Synthesis Example

3-Ethyl-2-methoxymaleic anhydride

In the same manner as Example 17, the title compound was obtained from ethyl 2-ketobutyrate and methyl methoxyacetate as oil (yield: 37%).

$^1$H NMR (CDCl$_3$) δ 1.18 (t, J=7.6 Hz, 3H), 2.45 (q, J=7.6 Hz, 2H), 4.25 (s, 3H).

Example 62

3-Ethyl-2-methoxymaleic acid disodium

In the same manner as Example 11, the title compound was obtained from 3-ethyl-2-methoxymaleic anhydride as a solid (quantitative).

$^1$H NMR (D$_2$O) δ 0.82 (t, J=7.5 Hz, 3H), 2.13 (q, J=7.5 Hz, 2H), 3.39 (s, 3H); MS (FAB+) m/z 219 [(M+H)$^+$].

Example 63

Synthesis Example

3-Ethyl-2-methylthiomaleic anhydride

In the same manner as Example 17, the title compound was obtained from ethyl 2-ketobutyrate and methyl thioethylacetate as oil (yield: 18%).

$^1$H NMR (CDCl$_3$) δ 1.18 (t, J=7.5 Hz, 3H), 2.49 (q, J=7.5 Hz, 2H), 2.77 (s, 3H).

Example 64

3-ethyl-2-methylthiomaleic acid disodium

In the same manner as Example 11, the title compound was obtained form 3-ethyl-2-methylthiomaleic anhydride as a solid (quantitative).

$^1$H NMR (D$_2$O) δ 0.81 (t, J=7.5 Hz, 3H), 2.05 (s, 3H), 2.22 (q, J=7.5 Hz, 2H); MS (ESI+) m/z 235 [(M+H)$^+$].

Example 65

Synthesis Example

3-Ethyl-2-isopropylthiomaleic anhydride

In the same manner as Example 17, the title compound was obtained from ethyl 2-ketobutyrate and isopropyl thioethylacetate as oil (yield: 26%).

$^1$H NMR (CDCl$_3$) δ 1.17 (t, J=7.6 Hz, 3H), 1.37 (d, J=6.8 Hz, 6H), 2.49 (q, J=7.6 Hz, 2H), 4.38 (septet, J=6.8 Hz, 1H).

Example 66

3-Ethyl-2-isopropylthiomaleic acid disodium

In the same manner as Example 11, the title compound was obtained from 3-ethyl-2-isopropylthiomaleic anhydride as a solid (quantitative).

$^1$H NMR (D$_2$O) δ 1.17 (t, J=7.6 Hz, 3H), 1.37 (d, J=6.8 Hz, 6H), 2.49 (q, J=7.6 Hz, 2H), 4.38 (septet, J=6.8 Hz, 1H); MS (FAB+) m/z 263 [(M+H)$^+$].

Example 67

Synthesis Example

Ethyl 3-{4-[(t-butyldiphenylsilyloxymethyl)phenyl]}propionate a) To a solution of 4-(t-butyldiphenylsilyloxymethyl)benzaldehyde (3.26 g, 8.71 mmol) in benzene (80 mL) were added ethyl (triphenylphospholanylidene)acetate (3.19 g, 9.14 mmol) and benzoic acid (116.0 mg, 0.950 mmol) at room temperature, and the mixture was heated under reflux with stirring for 2 h. The reaction mixture was directly concentrated under reduced pressure, and the residue thus obtained was diluted with hexane (80 mL) and diethyl ether (40 mL) and stirred for 8 h. Precipitated solids were filtered, and the residue obtained by concentrating the filtrate under reduced pressure was subjected to silica gel column chromatography (hexane-ethyl acetate 25:1) to give 13.47 g of ethyl (E)-3-{4-[(t-butyldiphenylsilyloxy)methyl]phenyl}acrylate as oil (yield: 90%).

b) To a solution of ethyl (E)-3-{[(t-butyldiphenylsilyloxy)methyl]phenyl}acrylate (3.47 g, 7.80 mmol) in methanol (70 mL) were added diphenyl sulfide (14 mg, 0.078 mmol) and 10% palladium/carbon (1.06 g), and the mixture was vigorously stirred at room temperature under hydrogen atmosphere for 12 h. The reaction mixture was filtered, and the residue obtained by concentrating the filtrate under reduced pressure was subjected to silica gel column chromatography (hexane-ethyl acetate 25:1→10:1) to give 3.21 g of the title compound as oil (yield: 92%).

$^1$H NMR (CDCl$_3$) δ 1.09 (s, 9H), 1.24 (t, J=7.2 Hz, 3H), 2.62 (t, J=7.8 Hz, 2H), 2.95 (t, J=7.8 Hz, 2H), 4.13 (q, J=7.2 Hz, 2H), 4.74 (s, 2H), 7.17 (d, J=8.0 Hz, 2H), 7.27 (d, J=8.0 Hz, 2H), 7.17 (d, J=8.0 Hz, 2H), 7.35-7.43 (m, 6H), 7.69 (m, 4H).

Example 68

Synthesis Example

2-[4-(Hydroxymethyl)benzyl]-3-isopropylmaleic anhydride a) To diisopropylamine (1.06 g, 0.763 mmol) dissolved in anhydrous tetrahydrofuran (15 mL) under the atmosphere of argon was added 1.60 M n-butyl lithium-hexane solution (4.5 mL, 7.16 mmol) with stirring under ice cooling, and the mixture was stirred at 0° C. for 10 min, and then at −78° C. for 5 min. To the mixture, ethyl 3-{4-[(t-butyldiphenylsilyloxymethyl)phenyl]}propionate (3.20 g, 7.16 mmol) dissolved in anhydrous tetrahydrofuran (20 mL) was added dropwise at the same temperature over 15 min, and the reaction mixture was further stirred for 20 min. The cold solution of the enolate thus prepared was added dropwise via a cannula to a solution of ethyl 3-methyl-2-ketobutyrate (1.14 g, 7.88 mmol) in anhydrous tetrahydrofuran (5.5 mL) having been cooled to −78° C. After stirring at −78° C. for 1 h, the reaction mixture was adjusted to pH 4 with acetic acid, and raised up to room temperature. The reaction solvent was evaporated under reduced pressure, and the residue was diluted with ethyl acetate and water to separate the phases. After the organic layer was washed with brine, the mixture was concentrated under reduced pressure and the residue thus obtained was subjected to silica gel column chromatography (hexane-ethyl acetate 10:1) to give diethyl 3-{4-[(t-butyldiphenylsilyloxymethyl)phenyl]}-2-isopropyl-2-hydroxysuccinate as oil in amounts of 962 mg (low polar diastereomer, yield: 23%) and 999 mg (high polar diastereomer, yield: 24%), respectively.

b) To a solution of diethyl 3-{4-[(t-butyldiphenylsilyloxymethyl)phenyl]}-2-isopropyl-2-hydroxysuccinate (1.32 g, 1.59 mmol) in tetrahydrofuran (26 mL) was added a 1 M tetrabutylammonium fluoride-tetrahydrofuran solution (2.45 mL, 2.45 mmol) at room temperature, and the mixture was left standing at room temperature for 2 h. The reaction mixture was directly concentrated under reduced pressure and the residue thus obtained was subjected to silica gel column chromatography (hexane-ethyl acetate 2:1→1:1) to give 700 mg of diethyl 2-isopropyl-3-{4-[(hydroxymethyl)phenyl]}-2-hydroxysuccinate as oil (yield: 89%).

c) To a solution of diethyl 2-isopropyl-3-{4-[(hydroxymethyl)phenyl]}-2-hydroxysuccinate thus obtained (700 mg, 1.99 mmol) in 1,4-dioxane (6.0 mL) was added 1 M aqueous lithium hydroxide solution (4.0 mL, 4.0 mmol) at room temperature, and the mixture was stirred at 60° C. for 16 h. Furthermore, 5 M aqueous sodium hydroxide solution (16.5 mL, 82.5 mmol) was added, and the reaction mixture was stirred at 90° C. for 24 h. After the reaction mixture was left cooling and stirred under ice cooling together with 5 N hydrochloric acid (19 mL), the reaction mixture was concentrated to dryness to give a crude 2-isopropyl-3-{4-[(hydroxymethyl)phenyl]}-2-hydroxysuccinic acid.

d) To the crude 2-isopropyl-3-{4-[(hydroxymethyl)phenyl]}-2-hydroxysuccinic acid obtained in the step c) described above was added acetic anhydride (20 mL), and the mixture was stirred at 140° C. for 2 h. The reaction mixture was directly filtrated, and the residue obtained by concentrating the filtrate under reduced pressure was subjected to silica gel column chromatography (hexane-ethyl acetate 6:1) to give 302 mg of 2-isopropyl-3-{4-[(hydroxymethyl)phenyl]}-2-hydroxysuccinic anhydride (2 step yield: 50%).

e) To a solution of 2-isopropyl-3-{4-[(hydroxymethyl)phenyl]}-2-hydroxysuccinic anhydride (224 mg, 0.742 mmol) in methanol (9 mL) was added sulfuric acid (18 mg, 0.18 mmol), and the mixture was heated under reflux with stirring for 12 h. The reaction mixture was directly concentrated under reduced pressure, and the residue thus obtained was subjected to silica gel column chromatography (hexane-diethyl ether 1:1) to give 101 mg of the title compound as oil (yield: 52%).

$^1$H NMR (CDCl$_3$) δ 1.28 (d, J=7.0 Hz, 6H), 3.07 (septet, J=7.0 Hz, 1H), 3.80 (s, 2H), 4.68 (d, J=4.4 Hz, 2H), 7.22 (d, J=8.1 Hz, 2H), 7.33 (d, J=8.1 Hz, 2H).

Example 69

2-(4-Carboxybenzyl)-3-isopropylmaleic acid dimethyl ester a) To a solution of 2-[4-(hydroxymethyl)benzyl]-3-isopropylmaleic anhydride (101 mg, 0.388 mmol) in a mixed solvent of methanol (1.0 mL) and tetrahydrofuran (1.0 mL) was added a 2.0 M trimethylsilyl diazomethane-hexane solution (1.0 mL, 2.0 mmol) with stirring under ice cooling. The reaction mixture was stirred at room temperature for 2 h and directly concentrated under reduced pressure. The residue thus obtained was subjected to silica gel column chromatography (toluene-ethyl acetate 4:1→3:1) to give 96 mg of dimethyl 2-[4-(hydroxymethyl)benzyl]-3-isopropylmaleate as oil (yield: 81%).

b) To a solution of dimethyl 2-[4-(hydroxymethyl)benzyl]-3-isopropylmaleate (96 mg, 0.31 mmol) in benzene (2.0 mL) was added active manganese dioxide (602 mg), and the mixture was vigorously stirred at room temperature for 3 h. After the reaction mixture was filtered, the filtrate was concentrated to dryness to give 79 mg of 2-(4-formylbenzyl)-3-isopropylmaleic acid dimethyl ester as colorless oil (yield: 83%).

c) To a suspension of 2-(4-formylbenzyl)-3-isopropylmaleic acid dimethyl ester (79 mg, 0.259 mmol) in a mixed solvent of dioxane (3.0 mL) and water (3.0 mL) were added amide sulfate (38 mg, 0.39 mmol) and sodium chlorite (35 mg, 0.39 mmol) with stirring under ice cooling, and the mixture was stirred for 30 min. The reaction mixture was directly concentrated, and the residue thus obtained was subjected to silica gel column chromatography (hexane-ethyl acetate 1:2) to give 80 mg of the title compound as oil (yield: 96%).

$^1$H NMR (CDCl$_3$) δ 1.12 (d, J=6.8 Hz, 6H), 2.95 (septet, J=6.8 Hz, 1H), 3.66 (s, 3H), 3.83 (s, 5H), 7.28 (m, 2H), 8.03 (m, 2H); MS (ESI+) m/z 321 [(M+H)$^+$].

Example 70

2-(4-Carboxybenzyl)-3-isopropylmaleic acid trisodium

In the same manner as Example 2, the title compound was obtained from 2-(4-carboxybenzyl)-3-isopropylmaleic acid dimethyl ester as a solid (quantitative).

$^1$H NMR (D$_2$O) δ 0.89 (d, J=6.8 Hz, 6H), 2.67 (septet, J=6.8 Hz, 1H), 3.55 (s, 2H), 7.18 (d, 2H), 7.61 (d, 2H); MS (FAB+) m/z 359 [(M+H)$^+$].

Example 71

2-(4-Carbamoylbenzyl)-3-isopropylmaleic acid dimethyl ester

To a solution of 2-(4-carboxybenzyl)-3-isopropylmaleic acid dimethyl ester (7.8 mg, 0.024 mmol) in tetrahydrofuran (400 μL) were added a 0.5 M ammonia-dioxane solution (600 μL) and 4-(4,6-dimethoxy-1,3,5-triazin-2-yl)-4-methylmorpholinium chloride (14.8 mg, 0.0535 mmol), and the mixture was stirred at room temperature for 4 h. The reaction mixture was directly concentrated under reduced pressure and the residue thus obtained was subjected to silica gel column chromatography (hexane-ethyl acetate 1:4) to give 7.0 mg of the title compound as a solid (yield: 90%).

$^1$H NMR (CDCl$_3$) δ 1.11 (d, J=6.8 Hz, 6H), 2.95 (septet, J=6.8 Hz, 1H), 3.65 (s, 3H), 3.80 (s, 2H), 3.82 (s, 3H), 5.54 (br s, 1H), 6.02 (br s, 1H), 7.26 (d, J=8.5 Hz, 2H), 7.74 (d, J=8.5 Hz, 2H); MS (ESI+) m/z 320 [(M+H)$^+$].

Example 72

2-(4-Carbamoylbenzyl)-3-isopropylmaleic acid disodium

In the same manner as Example 2, the title compound was obtained from 2-(4-carbamoylbenzyl)-3-isopropylmaleic acid dimethyl ester as a solid (quantitative).
$^1$H NMR (D$_2$O) δ 0.87 (d, J=6.8 Hz, 6H), 2.66 (septet, J=6.8 Hz, 1H), 3.57 (s, 2H), 7.23 (d, J=8.2 Hz, 2H), 7.56 (d, J=8.2 Hz, 2H); MS (FAB+) m/z 336 [(M+H)$^+$].

Example 73

2-Isopropyl-3-[4-(morpholine-1-carbonyl)benzyl]-maleica acid dimethyl ester

To a solution of 2-(4-carboxybenzyl)-3-isopropylmaleic acid dimethyl ester (9.7 mg, 0.030 mmol) in dichloromethane (300 μL) were added 1-hydroxybenzotriazole (14.1 mg, 0.104 mmol), 1-ethyl-3-(3-dimethylaminopropyl)carbodiimide hydrochloride (18.8 mg, 0.0981 mol) and morpholine (12.9 mg, 0.151 mmol) with stirring under ice cooling. After stirring under ice cooling for 2 h and at room temperature for further 1 h, The reaction mixture was diluted with water and chloroform to separate the phases. The aqueous layer was extracted again with ethyl acetate, and the combined organic layer was concentrated under reduced pressure and the residue thus obtained was subjected to silica gel column chromatography (ethyl acetate alone) to give 11.8 mg of the title compound as oil (quantitative).
$^1$H NMR (CDCl$_3$) δ 1.12 (d, J=6.8 Hz, 6H), 2.95 (septet, J=6.8 Hz, 1H), 3.35-3.82, (m, 8H), 3.66 (s, 3H), 3.78 (s, 2H), 3.82 (s, 3H), 7.22 (m, 2H), 7.34 (m, 2H).

Example 74

2-isopropyl-3-[4-(morpholine-1-carbonyl)benzyl] maleic acid disodium

In the same manner as Example 2, the title compound was obtained from 2-isopropyl-3-[4-(morpholine-1-carbonyl) benzyl]maleic acid dimethyl ester as a solid (quantitative).
$^1$H NMR (D$_2$O) δ 0.86 (d, J=6.8 Hz, 6H), 2.65 (septet, J=6.8 Hz, 1H), 3.34 (m, 2H), 3.50 (m, 2H), 3.53 (s, 2H), 3.57 (m, 2H), 3.64 (m, 2H), 7.15-7.20 (m, 4H); MS (ESI+) m/z 362 {[(M−2Na+2H)+H]$^+$}.

Example 75

2-isopropyl-3-[4-(piperazine-1-carbonyl)benzyl] maleica acid dimethyl ester hydrochloride a) In the same manner as Example 73, 2-{4-[4-(t-butoxycarbonyl)piperazine-1-carbonyl]benzyl}-3-iso propylmaleic acid dimethyl ester was obtained from 2-(4-carboxybenzyl)-3-isopropylmaleic acid dimethyl ester and t-butyl piperazine-1-carboxylate (quantitative).
b) To a solution of 2-{4-[4-(t-butoxycarbonyl)piperazine-1-carbonyl]benzyl}-3-iso propylmaleic acid dimethyl ester (11.8 mg, 0.0302 mmol) in methanol (200 μL) was added 5 M hydrochloric acid (200 μL) at room temperature, and the mixture was left standing for 5 h. The reaction mixture was directly concentrated to dryness to give 10.2 mg of the title compound as a solid (quantitative).
$^1$H NMR (CDCl$_3$) δ 0.89 (d, J=7.0 Hz, 6H), 2.92 (septet, J=7.0 Hz, 1H), 3.09 (br s, 2H), 3.16 (br s, 2H), 3.49 (s, 3H), 3.58 (br s, 2H), 3.67 (s, 3H), 3.70 (s, 2H), 3.81 (br s, 2H), 7.16 (d, J=8.1 Hz, 2H), 7.24 (d, J=8.1 Hz, 2H).

Example 76

2-Isopropyl-3-[4-(piperazine-1-carbonyl)benzyl] maleic acid disodium

In the same manner as Example 2, the title compound was obtained from 2-isopropyl-3-[4-(piperazine-1-carbonyl)benzyl]maleic acid dimethyl ester as a solid (quantitative).
$^1$H NMR (D$_2$O) δ 0.87 (d, J=7.0 Hz, 6H), 2.57-2.73 (m, 5H), 3.27 (m, 1H), 3.50-3.53 (m, 3H), 7.13-7.20 (m, 4H); MS (ESI−) m/z 359 {[(M−2Na+2H)—H]$^-$}.

Example 77

2-[4-(4-Acetoxypiperidin-1-carbonyl)benzyl]-3-isopropylmaleic acid dimethyl ester To a solution of 2-(4-carboxybenzyl)-3-isopropylmaleic acid dimethyl ester (10.3 mg, 0.0322 mmol) in dichloromethane (500 μL) were added 1-hydroxybenzotriazole (13.3 mg, 0.0965 mmol), 1-ethyl-3-(3-dimethylaminopropyl)carbodiimide hydrochloride (20.8 mg, 0.109 mol), piperidin-4-yl acetate hydrochloride (28.8 mg, 0.161 mmol) and triethylamine (14.6 mg, 0.145 mmol) with stirring under ice cooling. After stirring at room temperature for 1 h, the reaction mixture was diluted with water to separate the phases. The aqueous layer was extracted again with ethyl acetate, and the combined organic layer was concentrated under reduced pressure and the residue thus obtained was subjected to silica gel column chromatography (hexane-ethyl acetate 1:2) to give 11.1 mg of the title compound as a solid (yield: 78%).
$^1$H NMR (CDCl$_3$) δ 1.11 (d, J=7.0 Hz, 6H), 1.61 (br s, 1H), 1.74 (br s, 1H), 1.86 (br s, 1H), 1.96 (br s, 1H), 2.08 (br s, 3H), 2.96 (septet, J=7.0 Hz, 1H), 3.31 (br s, 1H), 3.53 (br s, 1H), 3.66 (br s, 1H), 3.66 (s, 3H), 3.78 (s, 2H), 3.82 (s, 3H), 4.07 (br s, 1H), 5.01 (m, 1H), 7.21 (m, 2H), 7.33 (m, 2H).

Example 78

2-[4-(4-Hydroxypiperidin-1-carbonyl)benzyl]-3-isopropylmaleic acid disodium

In the same manner as Example 2, the title compound was obtained from 2-[4-(4-acetoxypiperidin-1-carbonyl)benzyl]-3-isopropylmaleic acid dimethyl ester as a solid (quantitative).
$^1$H NMR (D$_2$O) δ 0.89 (d, J=7.0 Hz, 6H), 1.28-1.44 (m, 2H), 1.65-1.91 (m, 2H), 2.69 (septet, J=7.0 Hz, 1H), 3.04-3.12 (m, 2H). 3.55 (m, 1H), 3.56 (s, 2H), 3.82 (m, 1H), 4.04 (m, 1H), 7.15-7.23 (m, 4H); MS (ESI+) m/z 376 {[(M−2Na+2H)+H]$^+$}.

Example 79

2-[4-(2-Amino-2-oxoethylcarbamoyl)benzyl]-3-isopropylmaleic acid dimethyl estere In the same manner as Example 77, the title compound was obtained from 2-(4-carboxybenzyl)-3-isopropylmaleic acid dimethyl ester and glycineamide hydrochloride as a solid (yield: 84%).

¹H NMR (CD₃OD) δ 1.08 (d, J=6.8 Hz, 6H), 3.03 (septet, J=6.8 Hz, 1H), 3.62 (s, 3H), 3.76 (s, 3H), 3.84 (s, 2H), 4.02 (s, 2H), 7.28 (d, J=8.3 Hz, 2H), 7.81 (d, J=8.3 Hz, 2H).

Example 80

2-[4-(2-Amino-2-oxoethylcarbamoyl)benzyl]-3-isopropylmaleic acid disodiume

In the same manner as Example 2, the title compound was obtained from 2-[4-(2-amino-2-oxoethylcarbamoyl)benzyl]-3-isopropylmaleic acid dimethyl ester as a solid (quantitative).
¹H NMR (D₂O) δ 0.87 (d, J=6.8 Hz, 6H), 2.65 (septet, J=6.8 Hz, 1H), 3.57 (s, 2H), 3.92 (s, 2H), 7.24 (d, J=8.3 Hz, 2H), 7.58 (d, J=8.3 Hz, 2H); MS (ESI+) m/z 349 {[(M−2Na+2H)+H]⁺}.

Example 81

Synthesis Example

2-Isopropyl-3-(4-methoxybenzyl)maleic anhydride

In the same manner as Example 50, the title compound was obtained from benzyl 3-methyl-2-ketobutyrate and benzyl 3-(4-methoxyphenyl)propionate as oil (yield: 51%).
¹H NMR (CDCl₃) δ 1.28 (d, J=7.0 Hz, 6H), 3.05 (septet, J=7.0 Hz, 1H), 3.74 (s, 2H), 3.79 (s, 3H), 6.85 (d, J=8.7 Hz, 2H), 7.14 (d, J=8.7 Hz, 2H).

Example 82

2-Isopropyl-3-(4-methoxybenzyl)maleic acid disodium

In the same manner as Example 11, the title compound was obtained from 2-isopropyl-3-(4-methoxybenzyl)maleic anhydride as a solid (quantitative).
¹H NMR (D₂O) δ 0.85 (d, J=7.0 Hz, 6H), 2.65 (septet, J=7.0 Hz, 1H), 3.41 (s, 2H), 3.61 (s, 3H), 6.74 (m, 2H), 7.04 (m, 2H); MS (ESI+) m/z 323 [(M+H)⁺].

Example 83

Synthesis Example

Benzyl 3-[4-(t-butyldimethylsilyloxy)phenyl]propionate a) To a solution of 3-(4-hydroxyphenyl)propionic acid (1.49 g, 8.96 mmol) in dimethylformamide (21.5 mL) were added potassium carbonate (1.30 g, 9.41 mmol) and benzyl bromide (1.69 g, 9.86 mmol), and the mixture was stirred at room temperature for 12 h. The reaction mixture was diluted with toluene and water to separate the phases. The residue obtained by concentrating the organic layer under reduced pressure was subjected to silica gel column chromatography (hexane-ethyl acetate 5:1→3:1) to give 2.16 g of benzyl 3-(4-hydroxyphenyl)propionate as oil (yield: 94%).
b) In the same manner as Example 12, the title compound was obtained from benzyl 3-(4-hydroxyphenyl)propionate as oil (yield: 93%).
¹H NMR (CDCl₃) δ 0.18 (s, 6H), 0.98 (s, 9H), 2.65 (m, 2H), 2.90 (m, 2H), 5.11 (s, 2H), 6.73 (m, 2H), 7.03 (m, 2H), 7.26-7.40 (m, 5H).

Example 84

Synthesis Example

2-[4-(t-Butyldimethylsilyloxy)benzyl]-3-isopropylmaleic anhydride

In the same manner as Example 50, the title compound was obtained from benzyl 3-methyl-2-ketobutyrate and benzyl 3-[4-(t-butyldimethylsilyloxy)phenyl]propionate as oil (yield: 58%).
¹H NMR (CDCl₃) δ 0.18 (s, 6H), 0.97 (s, 9H), 1.25 (d, J=6.8 Hz, 6H), 3.02 (septet, J=6.8 Hz, 1H), 3.72 (s, 2H), 6.78 (m, 2H), 7.06 (m, 2H).

Example 85

2-(4-Hydroxybenzyl)-3-isopropylmaleic acid dimethyl ester a) To a solution of 2-[4-(t-butyldimethylsilyloxy)benzyl]-3-isopropylmaleic anhydride (823 mg, 2.28 mmol) in methanol (15 mL) was added a 2.0 M trimethylsilyl diazomethane-hexane solution (8.5 mL, 17 mmol) with stirring at room temperature. After stirring at room temperature for 30 min, the reaction mixture was concentrated under reduced pressure and the residue thus obtained was subjected to silica gel column chromatography (hexane-ethyl acetate 10:1→8:1) to give 913 mg of dimethyl 2-[4-(t-butyldimethylsilyloxy)benzyl]-3-isopropylmaleate as oil (yield: 98%).
b) To a solution of dimethyl 2-[4-(t-butyldimethylsilyloxy)benzyl]-3-isopropylmaleate (823 mg, 2.02 mmol) in tetrahydrofuran (13 mL) was added a 1 M tetrabutylammonium fluoride-tetrahydrofuran solution (2.1 mL, 2.1 mmol) at room temperature, and the mixture was left standing at room temperature for 1 h. The reaction mixture was directly concentrated under reduced pressure and the residue thus obtained was subjected to silica gel column chromatography (hexane-ethyl acetate2:1) to give 592 mg of 2-(4-hydroxybenzyl)-3-isopropylmaleic acid dimethyl ester as a solid (quantitative).
¹H NMR (CDCl₃) δ 1.11 (d, J=6.8 Hz, 6H), 2.98 (septet, J=6.8 Hz, 1H), 3.65 (s, 3H), 3.68 (s, 2H), 3.80 (s, 3H), 4.98 (br s, 1H), 6.74 (m, 2H), 7.02 (m, 2H).

Example 86

2-(4-Oxidobenzyl)-3-isopropylmaleic acid trisodium

In the same manner as Example 2, the title compound was obtained from 2-(4-hydroxybenzyl)-3-isopropylmaleic acid dimethyl ester as a solid (quantitative).
¹H NMR (D₂O) δ 0.90 (d, J=7.0 Hz, 6H), 2.71 (septet, J=7.0 Hz, 1H), 3.36 (s, 2H), 6.45 (m, J=8.5 Hz, 2H), 6.90 (d, J=8.5 Hz, 2H); MS (FAB+) m/z 331 [(M+H)⁺].

Example 87

2-Isopropyl-3-[4-(2-methoxy-2-oxoethoxy)benzyl] maleic acid dimethyl ester

To a solution of 2-(4-hydroxybenzyl)-3-isopropylmaleic acid dimethyl ester (44.1 mg, 0.151 mmol) in (880 μL) were added potassium carbonate (34.7 mg, 0.251 mmol) and methyl bromoacetate (138.4 mg, 0.904 mmol) with stirring at room temperature. After stirring at room temperature for 20 h, the reaction mixture was diluted with toluene and water to separate the phases. The aqueous layer was extracted again with toluene, and the combined organic layer was concentrated under reduced pressure and the residue thus obtained was subjected to silica gel column chromatography (toluene-ethyl acetate 10:1) to give 45.2 mg of the title compound as oil (yield: 82%).

$^1$H NMR (CDCl$_3$) δ 1.11 (d, J=7.0 Hz, 6H), 2.97 (septet, J=7.0 Hz, 1H), 3.65 (s, 3H), 3.69 (s, 2H), 3.80 (s, 3H), 3.81 (s, 3H), 4.61 (s, 2H), 6.83 (m, 2H), 7.09 (m, 2H).

Example 88

2-[4-(Carboxylatomethoxy)benzyl]-3-isopropylmaleic acid tridodium

In the same manner as Example 2, the title compound was obtained from 2-isopropyl-3-[4-(2-methoxy-2-oxoethoxy)benzyl]maleic acid dimethyl ester as a solid (quantitative).

$^1$H NMR (D$_2$O) δ 0.89 (d, J=7.0 Hz, 6H), 2.68 (septet, J=7.0 Hz, 1H), 3.45 (s, 2H), 4.29 (s, 2H), 6.72 (d, J=8.5 Hz, 2H), 7.06 (d, J=8.5 Hz, 2H); MS (FAB+) m/z 389 [(M+H)$^+$].

Example 89

2-[4-(2-Amino-2-oxoethoxy)benzyl]-3-isopropylmaleic acid dimethyl ester

In the same manner as Example 87, the title compound was obtained from 2-(4-hydroxybenzyl)-3-isopropylmaleic acid dimethyl ester and bromoacetamide as oil (yield: 80%).

$^1$H NMR (CDCl$_3$) δ 1.12 (d, J=7.0 Hz, 6H), 2.98 (septet, J=7.0 Hz, 1H), 3.65 (s, 3H), 3.67 (s, 2H), 3.80 (s, 3H), 4.47 (s, 2H), 5.58 (br s, 1H), 6.54 (br s, 1H), 6.84 (m, 2H), 7.12 (m, 2H); MS (FAB+) m/z 372 [(M+Na)$^+$].

Example 90

2-[4-(2-Amino-2-oxoethoxy)benzyl]-3-isopropylmaleic acid disodium

In the same manner as Example 2, the title compound was obtained from 2-[4-(2-amino-2-oxoethoxy)benzyl]-3-isopropylmaleic acid dimethyl ester as a solid (quantitative).

$^1$H NMR (D$_2$O) δ 0.91 (d, J=6.8 Hz, 6H), 2.70 (septet, J=6.8 Hz, 1H), 3.48 (s, 2H), 4.47 (s, 2H), 6.81 (d, J=8.5 Hz, 2H), 7.11 (d, J=8.5 Hz, 2H); MS (FAB+) m/z 320 {[(M−2Na+2H)+H]$^+$}.

Example 91

2-[4-(2-Aminoethoxy)benzyl]-3-isopropylmaleic acid dimethyl ester a) To a solution of 2-(4-hydroxybenzyl)-3-isopropylmaleic acid dimethyl ester (204.5 mg, 0.6996 mmol) in benzene (6 mL) were added N-(t-butoxycarbonyl)ethanolamine (343 mg, 2.13 mol), tributylphosphine (853 mg, 4.20 mmol) and 1,1'-(azodicarbonyl)dipiperidine (1.05 g, 4.20 mmol) with stirring at room temperature. After stirring at room temperature for 1 h, the reaction mixture was filtered, and the residue obtained by concentrating the filtrate under reduced pressure was subjected to silica gel column chromatography (hexane-ethyl acetate 2:1) to give 287 mg of dimethyl 2-{4-[2-(t-butoxycarbonylamino)ethoxy]benzyl}-3-isopropylmaleate as oil (yield: 98%).

b) To a solution of dimethyl 2-{4-[2-(t-butoxycarbonylamino)ethoxy]benzyl}-3-isopropylmaleate (287 mg, 0.659 mmol) in methanol (6 mL) was added 5 M hydrochloric acid (5.9 mL) at room temperature, and the mixture was left standing at room temperature for 20 h. The residue obtained by concentrating the mixture under reduced pressure was dissolved in ethyl acetate, and a saturated aqueous sodium hydrogen carbonate solution was added. After separating the phases, the organic layer was concentrated and the residue thus obtained was subjected to LH-20 (dichloromethane-methanol 1:1) to give 222 mg of the title compound as oil (quantitative).

$^1$H NMR (CDCl$_3$) δ 1.11 (d, J=7.0 Hz, 6H), 2.99 (septet, J=7.0 Hz, 1H), 3.07 (t, J=5.1 Hz, 2H), 3.65 (s, 3H), 3.69 (s, 2H), 3.80 (s, 3H), 3.96 (t, J=5.1 Hz, 2H), 6.82 (m, 2H), 7.08 (m, 2H).

Example 92

2-[4-(2-aminoethoxy)benzyl]-3-isopropylmaleic acid disodium

In the same manner as Example 2, the title compound was obtained from 2-[4-(2-aminoethoxy)benzyl]-3-isopropylmaleic acid dimethyl ester as a solid (quantitative).

$^1$H NMR (D$_2$O) δ 0.89 (d, J=7.0 Hz, 6H), 2.68 (septet, J=7.0 Hz, 1H), 2.82 (m, 2H), 3.45 (s, 2H), 3.91 (m, 2H), 6.79 (m, 2H), 7.07 (m, 2H); MS (FAB+) m/z 352 [(M+H)$^+$].

Example 93

2-{4-[2-(1H-Imidazol-1-yl)ethoxy]benzyl}-3-isopropylmaleic acid dimethyl ester

In the same manner as Example 91a, the title compound was obtained from 2-(4-hydroxybenzyl)-3-isopropylmaleic acid dimethyl ester and 1-(2-hydroxyethyl)imidazole as oil (yield: 52%).

$^1$H NMR (CDCl$_3$) δ 1.11 (d, J=7.0 Hz, 6H), 2.97 (septet, J=7.0 Hz, 1H), 3.01 (s, 3H), 3.68 (s, 2H), 3.80 (s, 3H), 4.18 (t, J=5.0 Hz, 2H), 4.32 (t, J=5.0 Hz, 2H), 6.78 (m, 2H), 7.03-7.09 (m, 4H), 7.60 (m, 1H); MS (ESI+) m/z 387 [(M+H)$^+$].

Example 94

2-{4-[2-(1H-Imidazol-1-yl)ethoxy]benzyl}-3-isopropylmaleic acid disodium

In the same manner as Example 2, the title compound was obtained from 2-{4-[2-(1H-imidazol-1-yl)ethoxy]benzyl}-3-isopropylmaleic acid dimethyl ester as a solid (quantitative).

$^1$H NMR (D$_2$O) δ 0.88 (d, J=7.0 Hz, 6H), 2.67 (septet, J=7.0 Hz, 1H), 3.45 (s, 2H), 4.20 (m, 2H), 4.24 (m, 2H), 6.72 (m, 2H), 6.85 (m, 1H), 7.03-7.08 (m, 3H), 7.58 (s, 1H); MS (ESI+) m/z 403 [(M+H)$^+$].

Example 95

2-Isopropyl-3-[4-(pyrrolidine-3-yloxy)benzyl]maleic acid dimethyl ester

In the same manner as Example 91, the title compound was obtained from 2-(4-hydroxybenzyl)-3-isopropylmaleic acid dimethyl ester and N-(t-butoxycarbonyl)-3-hydroxypyrrolidine as oil (yield: 82%).

¹H NMR (CDCl₃) δ 1.11 (d, J=7.0 Hz, 6H), 1.93 (m, 1H), 2.07 (m, 1H), 2.84-3.02 (m, 3H), 3.15-3.20 (m, 2H), 3.65 (s, 3H), 3.69 (s, 2H), 3.80 (s, 3H), 4.79 (m, 1H), 6.77 (m, 2H), 7.06 (m, 2H).

Example 96

2-isopropyl-3-[4-(pyrrolidine-3-yloxy)benzyl]maleic acid disodium

In the same manner as Example 2, the title compound was obtained from 2-isopropyl-3-[4-(pyrrolidine-3-yloxy)benzyl]maleic acid dimethyl ester as a solid (quantitative).
¹H NMR (D₂O) δ 0.90 (d, J=7.0 Hz, 6H), 1.84-1.98 (m, 2H), 2.69 (septet, J=7.0 Hz, 1H), 2.70-3.05 (m, 4H), 3.45 (s, 2H), 4.85 (m, 1H), 6.78 (m, 2H), 7.08 (m, 2H); MS (ESI+) m/z 334 {[(M−2Na+2H)+H]⁺}.

Example 97

2-[4-(2-Guanidinoethoxy)benzyl]-3-isopropylmaleic acid dimethyl ester hydrochloride a) To a solution of 2-[4-(2-aminoethoxy)benzyl]-3-isopropylmaleic acid dimethyl ester (30.2 mg, 0.0900 mmol) in tetrahydrofuran (900 μL) was added N,N'-bis(t-butoxycarbonyl)-1-guanylpyrazole (35.2 mg, 0.113 mmol) at room temperature, and the mixture was left standing for 20 h. The reaction mixture was directly concentrated under reduced pressure, and the residue obtained was subjected to silica gel column chromatography (hexane-ethyl acetate 3:1) to give 47.6 mg of dimethyl 2-[4-{2-[2,3-bis(t-butoxycarbonyl)guanidino]ethoxy}benzyl]-3-isopropylmaleate as a syrup (yield: 92%).

b) To a solution of dimethyl 2-[4-{2-[2,3-bis(t-butoxycarbonyl)guanidino]ethoxy}benzyl]-3-isopropylmaleate (23.5 mg, 0.0407 mmol) in methanol (470 μL) was added 5 M hydrochloric acid (407 μL) at room temperature, and the mixture was left standing for 4 h. The reaction mixture was concentrated to dryness to give 17.6 mg of the title compound as oil (quantitative).
¹H NMR (D₂O) δ 0.91 (d, J=7.0 Hz, 6H), 2.94 (septet, J=7.0 Hz, 1H), 3.43 (t, J=5.0 Hz, 3H), 3.50 (s, 3H), 3.57 (s, 2H), 3.68 (s, 3H), 4.02 (t, J=5.0 Hz, 2H), 6.80 (m, 2H), 7.01 (m, 2H).

Example 98

2-[4-(2-guanidinoethoxy)benzyl]-3-isopropylmaleic acid disodium

In the same manner as Example 2, the title compound was obtained from 2-[4-(2-guanidinoethoxy)benzyl]-3-isopropylmaleic acid dimethyl ester hydrochloride as a solid (quantitative).
¹H NMR (D₂O) δ 0.92 (d, J=6.8 Hz, 6H), 2.97 (m, 1H), 2.79 (septet, J=6.8 Hz, 1H), 2.79 (m, 2H), 3.69 (s, 2H), 4.04 (m, 2H), 6.83 (m, 2H), 7.07 (m, 2H); MS (ESI+) m/z 350 {[(M−2Na+2H)+H]⁺}.

The compounds prepared above have the structures as shown in the following Tables.

TABLE 1

| Example | Compounds |
|---|---|
| 1 | (structure: dimethyl 2-isopropyl-3-ethylmaleate; MeO₂C, CO₂Me) |
| 2 | (structure: disodium 2-isopropyl-3-ethylmaleate; NaO₂C, CO₂Na) |
| 3 | (structure: diethyl 2-isopropyl-3-ethylmaleate; EtO₂C, CO₂Et) |
| 4 | (structure: disodium salt; NaO₂C, CO₂Na) |
| 5 | (structure: dipotassium salt; KO₂C, CO₂K) |
| 6 | (structure: diethyl ester with propyl groups; EtO₂C, CO₂Et) |
| 7 | (structure: disodium salt with propyl groups; NaO₂C, CO₂Na) |
| 8 | (structure: dimethyl 2-benzyl-3-methylmaleate; MeO₂C, CO₂Me) |
| 9 | (structure: disodium 2-benzyl-3-methylmaleate; NaO₂C, CO₂Na) |
| 10 | (structure: 3-benzyl-4-ethylfuran-2,5-dione anhydride) |
| 11 | (structure: disodium 2-benzyl-3-isopropylmaleate; NaO₂C, CO₂Na) |
| 12 | (structure: ethyl ester with OTBS phenethyl group; CO₂Et, OTBS) |

TABLE 1-continued

| Example | Compounds |
|---|---|
| 13 | 3-ethyl-4-(4-acetoxybenzyl) furan-2,5-dione |
| 14 | 2-ethyl-3-(4-hydroxybenzyl) but-2-enedioic acid, disodium salt |
| 15 | 3,4-dibenzyl furan-2,5-dione |
| 16 | 2,3-dibenzyl but-2-enedioic acid, disodium salt |
| 17 | 3-benzyl-4-(2-phenylethyl) furan-2,5-dione |
| 18 | 2-benzyl-3-(2-phenylethyl) but-2-enedioic acid, disodium salt |
| 19 | 2,3-bis(2-phenylethyl) but-2-enedioic acid, diethyl ester |
| 20 | 2,3-bis(2-phenylethyl) but-2-enedioic acid, disodium salt |
| 21 | 3-methyl-4-isopropyl furan-2,5-dione |
| 22 | 2-methyl-3-isopropyl but-2-enedioic acid, disodium salt |
| 23 | 3-ethyl-4-isopropyl furan-2,5-dione |
| 24 | 2-ethyl-3-isopropyl but-2-enedioic acid, disodium salt |
| 25 | 3,4-diisopropyl furan-2,5-dione |
| 26 | 2,3-diisopropyl but-2-enedioic acid, disodium salt |
| 27 | 3-isopropyl-4-benzyl furan-2,5-dione |
| 28 | 2-isopropyl-3-benzyl but-2-enedioic acid, disodium salt |
| 29 | 3-isopropyl-4-(2-methylbenzyl) furan-2,5-dione |

TABLE 1-continued

| Example | Compounds |
|---|---|
| 30 | (structure: isopropyl, 2-methylbenzyl substituted maleate disodium salt) |
| 31 | (structure: 3-cyclopentyl-4-ethyl furan-2,5-dione) |
| 32 | (structure: cyclopentyl, ethyl substituted maleate disodium salt) |
| 33 | (structure: 3-cyclopentyl-4-isopropyl furan-2,5-dione) |
| 34 | (structure: cyclopentyl, isopropyl substituted maleate disodium salt) |
| 35 | (structure: cyclopentyl ketone with BnO₂C) |
| 36 | (structure: 3-benzyl-4-cyclopentyl furan-2,5-dione) |
| 37 | (structure: cyclopentyl, benzyl substituted maleate disodium salt) |

TABLE 1-continued

| Example | Compounds |
|---|---|
| 38 | (structure: 3,4-dicyclopentyl furan-2,5-dione) |
| 39 | (structure: dicyclopentyl substituted maleate disodium salt) |
| 40 | (structure: 3-indanyl-4-isopropyl furan-2,5-dione) |
| 41 | (structure: indanyl, isopropyl substituted maleate disodium salt) |
| 42 | (structure: 3-cyclohexyl-4-isopropyl furan-2,5-dione) |
| 43 | (structure: cyclohexyl, isopropyl substituted maleate disodium salt) |
| 44 | (two structures: trans-4-(OTBS)cyclohexyl methyl CO₂Bn, shown twice) |

TABLE 1-continued

| Example | Compounds |
|---|---|
| 45 | (structure: 3-isopropyl-4-(trans-4-hydroxycyclohexyl) furan-2,5-dione) |
| 46 | (structure: disodium 2-(trans-4-hydroxycyclohexyl)-3-isobutyl-2-butenedioate) |
| 47 | (structure: 3-isopropyl-4-(4-hydroxycyclohexyl) furan-2,5-dione) |
| 48 | (structure: disodium 2-(4-hydroxycyclohexyl)-3-isobutyl-2-butenedioate) |
| 49 | (structure: benzyl (tetrahydro-2H-pyran-4-yl)acetate) |
| 50 | (structure: 3-isopropyl-4-(tetrahydro-2H-pyran-4-yl) furan-2,5-dione) |
| 51 | (structure: disodium 2-(tetrahydro-2H-pyran-4-yl)-3-isobutyl-2-butenedioate) |
| 52 | (structure: benzyl 3-(pyridin-3-yl)propanoate) |
| 53 | (structure: 3-isopropyl-4-(pyridin-3-ylmethyl) furan-2,5-dione) |
| 54 | (structure: disodium 2-(pyridin-3-ylmethyl)-3-isobutyl-2-butenedioate) |
| 55 | (structure: dimethyl 2-methyl-3-(piperidin-1-ylmethyl)-2-butenedioate) |
| 56 | (structure: disodium 2-methyl-3-(piperidin-1-ylmethyl)-2-butenedioate) |
| 57 | (structure: dimethyl 2-methyl-3-((4-hydroxypiperidin-1-yl)methyl)-2-butenedioate) |
| 58 | (structure: disodium 2-methyl-3-((4-hydroxypiperidin-1-yl)methyl)-2-butenedioate) |
| 59 | (structure: 3-methyl-4-(hydroxymethyl) furan-2,5-dione) |
| 60 | (structure: disodium 2-methyl-3-(hydroxymethyl)-2-butenedioate) |
| 61 | (structure: 3-ethyl-4-methoxy furan-2,5-dione) |
| 62 | (structure: disodium 2-ethyl-3-methoxy-2-butenedioate) |

TABLE 1-continued

| Example | Compounds |
|---|---|
| 63 | 3-ethyl-4-(methylthio)furan-2,5-dione |
| 64 | disodium 2-ethyl-3-(methylthio)but-2-enedioate |
| 65 | 3-ethyl-4-(isopropylthio)furan-2,5-dione |
| 66 | disodium 2-ethyl-3-(isopropylthio)but-2-enedioate |
| 67 | ethyl 3-(4-(((tert-butyldiphenylsilyl)oxy)methyl)phenyl)propanoate |
| 68 | 3-(4-(hydroxymethyl)benzyl)-4-isopropylfuran-2,5-dione |
| 69 | dimethyl 2-(4-carboxybenzyl)-3-isopropylbut-2-enedioate |
| 70 | sodium 4-((2,3-bis(methoxycarbonyl)-4-methylpent-2-en-1-yl))benzoate disodium salt |
| 71 | dimethyl 2-(4-carbamoylbenzyl)-3-isopropylbut-2-enedioate |
| 72 | disodium 2-(4-carbamoylbenzyl)-3-isopropylbut-2-enedioate |
| 73 | dimethyl 3-isopropyl-2-(4-(morpholine-4-carbonyl)benzyl)but-2-enedioate |
| 74 | disodium 3-isopropyl-2-(4-(morpholine-4-carbonyl)benzyl)but-2-enedioate |
| 75 | dimethyl 3-isopropyl-2-(4-(piperazine-1-carbonyl)benzyl)but-2-enedioate hydrochloride |
| 76 | disodium 3-isopropyl-2-(4-(piperazine-1-carbonyl)benzyl)but-2-enedioate |
| 77 | dimethyl 2-(4-((4-acetoxypiperidin-1-yl)carbonyl)benzyl)-3-isopropylbut-2-enedioate |
| 78 | disodium 2-(4-((4-hydroxypiperidin-1-yl)carbonyl)benzyl)-3-isopropylbut-2-enedioate |
| 79 | dimethyl 2-(4-((2-amino-2-oxoethyl)carbamoyl)benzyl)-3-isopropylbut-2-enedioate |
| 80 | disodium 2-(4-((2-amino-2-oxoethyl)carbamoyl)benzyl)-3-isopropylbut-2-enedioate |

TABLE 1-continued

| Example | Compounds |
|---|---|
| 81 | (isopropyl, 4-methoxybenzyl maleic anhydride) |
| 82 | (isopropyl, 4-methoxybenzyl, NaO2C, CO2Na) |
| 83 | (4-OTBS-phenyl-CH2CH2-CO2Bn) |
| 84 | (isopropyl, 4-OTBS-benzyl maleic anhydride) |
| 85 | (isopropyl, 4-OH-benzyl, MeO2C, CO2Me) |
| 86 | (isopropyl, 4-ONa-benzyl, NaO2C, CO2Na) |
| 87 | (isopropyl, 4-(OCH2CO2Me)-benzyl, MeO2C, CO2Me) |
| 88 | (isopropyl, 4-(OCH2CO2Na)-benzyl, NaO2C, CO2Na) |
| 89 | (isopropyl, 4-(OCH2CONH2)-benzyl, MeO2C, CO2Me) |
| 90 | (isopropyl, 4-(OCH2CONH2)-benzyl, NaO2C, CO2Na) |
| 91 | (isopropyl, 4-(OCH2CH2NH2)-benzyl, MeO2C, CO2Me) |
| 92 | (isopropyl, 4-(OCH2CH2NH2)-benzyl, NaO2C, CO2Na) |
| 93 | (isopropyl, 4-(OCH2CH2-imidazolyl)-benzyl, MeO2C, CO2Me) |
| 94 | (isopropyl, 4-(OCH2CH2-imidazolyl)-benzyl, NaO2C, CO2Na) |
| 95 | (isopropyl, 4-(O-pyrrolidin-3-yl)-benzyl, MeO2C, CO2Me) |
| 96 | (isopropyl, 4-(O-pyrrolidin-3-yl)-benzyl, NaO2C, CO2Na) |

TABLE 1-continued

| Example | Compounds |
|---|---|
| 97 | 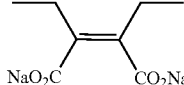 ·n HCl |
| 98 | 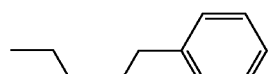 |

Inhibitory Activity

The total length of IMP-1 as a metallo-β-lactamase was amplified by PCR with a template of bla$_{IMP-1}$ of *Pseudomonas aeruginosa* MSC15369 which possesses IMP-1. The PCR product was integrated into pTrcHis2 TOPO vector (Invitrogen), and then introduced into *E. coli* DH5α (TOYOBO) for culture under the induction of 0.5 mM Isopropyl-β-D-(−)-thiogalactopyranoside (Wako) at 37° C. for 3 h to express IMP-1. After recovering the bacterial cells, the periplasmic fraction was extracted by ocmotic shock with sucrose to refine the IMP-1 by Ni-NTA Slurry (QIAGEN) with the His tag at the C-terminus. Similarly, bla$_{VIM-2}$ gene of *Pseudomonas putida* MSCO6534 which possesses VIM-2 as a metallo-β-lactamase was integrated and expressed in *E. coli* DH5α to refine the VIM-2.

In order to determine the inhibitory activity of metallo-β-lactamase, a 50 mM HEPES (pH 7.5) buffer (referred to hereinafter as "buffer") was used, and nitrocefin (Oxoid) with the final concentration of 100 μM was used as a substrate. A test drug (material to be tested: compound having an Example Number shown in Table 2) was added to each well of a 96-well plate, into which nitrocefin was added and mixed. Then, IMP-1 or VIM-2 was added to each well in the final concentration of 1 nM or 1.5 nM, respectively to react the mixture at room temperature for 20 min. In this case, ZnSO$_4$ was added in the final concentration of 100 μM in order to exclude the inhibitory effect by the chelate effect. Enzyme inhibiting activity was determined by measuring the hydrolysis activity of nitrocefin at a wave length of 490 nm with ARVOsx microplate reader (Wallac). A reaction solution without metallo-β-lactamase was prepared as a control, and the concentration of the test drug which exhibits 50% inhibition was set as IC$_{50}$. The results are shown in Table 2.

(Inhibitory Activity)

TABLE 2

| | IC$_{50}$ of each inhibitor against IMP-1 and VIM-2 | | |
|---|---|---|---|
| Example | Compounds | IMP-1 (μM) | VIM-2 (μM) |
| 4 |  | 2.5 | 13 |
| 11 | 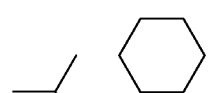 | 0.29 | 3.0 |
| 22 | 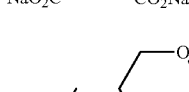 | 2.4 | 7.3 |
| 43 | | 0.19 | 0.16 |
| 51 | | 1.9 | 1.8 |

TABLE 2-continued

IC$_{50}$ of each inhibitor against IMP-1 and VIM-2

| Example | Compounds | IMP-1 (μM) | VIM-2 (μM) |
|---|---|---|---|
| 54 | (structure: isopropyl-substituted maleate with pyridin-3-ylmethyl group; NaO$_2$C, CO$_2$Na) | 2.8 | 5.3 |
| 66 | (structure: ethyl-substituted maleate with S-isopropyl group; NaO$_2$C, CO$_2$Na) | 1.2 | 14 |
| 72 | (structure: isopropyl-substituted maleate with 4-carbamoylbenzyl group; NaO$_2$C, CO$_2$Na) | 1.4 | 0.60 |
| 86 | (structure: isopropyl-substituted maleate with 4-(ONa)benzyl group; NaO$_2$C, CO$_2$Na) | 0.56 | 1.9 |
| 92 | (structure: isopropyl-substituted maleate with 4-(2-aminoethoxy)benzyl group; NaO$_2$C, CO$_2$Na) | 0.98 | 0.30 |

Combination Effect

IMP-1 producing *Pseudomonas aeruginosa* strain PAO1/pMS363 (FEMS Microbiology Letters 1994, 121, 175) was used for evaluating the inhibitory effect of maleic acid derivatives on the resistance against carbapenem by the metallo-β-lactamase in bacteria. Minimum inhibitory concentration (MIC) of imipenem, meropenem, biapenem, doripenem, CS-023, ceftriaxone, ceftadizime, and cefepime against IMP-1 producing *Pseudomonas aeruginosa* was measured by the microliquid dilution method which is the standard method of Japanese Society of Chemotherapy (Chemotherapy 1981, 29, 76). That is, a strain which had been cultured overnight in a Mueller-Hinton broth was adjusted to a concentration of 10$^4$ CFU/well, and added to the same media containing respective concentrations of imipenem (IPM), meropenem (MEPM), biapenem (BIPM), doripenem (DRPM) CS-023, ceftriaxone (CTRX), ceftadizime (CAZ), and cefepime (CFPM). The compound of the present invention was added to each well in the final concentration of 50 μg/ml to confirm its effect on the basis of MIC of imipenem, meropenem, biapenem, doripenem, CS-023, ceftriaxone, ceftadizime, and cefepime. The results are shown in Table 3.

(Combination Effect)

TABLE 3

Combination effect of the compounds with a variety of β-lactam drugs against metallo-β-lactamase producing *Pseudomonas aeruginosa* (combination with 50 μg/ml of inhibitor)

| | | MIC of β-lactam drugs (combination with 50 μg/ml of inhibitor) | | | | | | | |
|---|---|---|---|---|---|---|---|---|---|
| Example | Compounds | IPM | MEPM | BIPM | DRPM | CS-023 | CAZ | CFPM | CTRX |
| 4 |  | 2 | 4 | 1 | 4 | 4-8 | 16 | 8 | 64 |

TABLE 3-continued

Combination effect of the compounds with a variety of β-lactam drugs against metallo-β-lactamase producing *Pseudomonas aeruginosa* (combination with 50 μg/ml of inhibitor)

| Example | Compounds | MIC of β-lactam drugs (combination with 50 μg/ml of inhibitor) | | | | | | | |
|---|---|---|---|---|---|---|---|---|---|
| | | IPM | MEPM | BIPM | DRPM | CS-023 | CAZ | CFPM | CTRX |
| 11 | | 4 | NT | 4 | NT | NT | 128 | 64 | 256 |
| 22 | | 1-2 | 4 | 1 | 4 | 4 | 32 | 32 | 128 |
| 43 | | 2-4 | 16 | 2 | 16 | 16 | 64 | 32 | 256 |
| 51 | | 4 | 16 | 2 | 32 | 32 | 128 | 64 | 256 |
| 54 | | 16 | 32 | 4 | 32 | 32 | 256 | 128 | 512 |
| 66 | | 1 | 8 | 1 | 8 | 16 | 32 | 16 | 128 |
| 72 | | 8 | 16 | 8 | 16 | 64 | 1024 | 512 | 2048 |
| 86 | | 4 | 8 | 1 | 16 | 32 | 128 | 32 | 128 |
| 92 | | 2 | 4 | 0.5 | 4 | 8 | 16 | 8 | 64 |
| β-lactam alone | — | 128-256 | 128 | 64-128 | 128 | 256 | 2048 | 2048 | 4096 |

As shown in Table 2, it has been found that enzyme inhibiting activities as the metallo-β-lactamase inhibitors are observed in maleic acid derivatives of the general formula (I), the compounds of the present invention, which inhibit both enzymes of IMP and VIM series. While few metallo-β-lactamase inhibitors which exhibit the combination effect with β-lactam drugs have been described, it has been found that the compounds of the present invention, as shown in Table 3, have the effect of recovering the activities of imipenem by combining with imipenem against the metallo-β-lactamase producing *Pseudomonas aeruginosa* of which therapy has hitherto been regarded difficult in the medical field. Thus, the compound represented by the general formula (I) is useful as the metallo-β-lactamase inhibitor for the combination with β-lactam drugs and the like.

What is claimed is:

1. A process for treating a bacterial infection caused by metallo-β-lactamase producing bacteria, which comprises administering a compound represented by the following formula (I), or a salt thereof, as a metallo-β-lactamase inhibitor, to a mammal in need thereof:

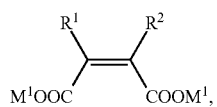

wherein:
  $R^1$ represents a $C_{2-6}$ alkyl group, a $C_{3-7}$ cycloalkyl group, a hydroxymethyl group, a —$C_{1-3}$ alkylene-phenyl group, a —$C_{0-1}$ alkylene-heterocycle, a —O—$C_{1-6}$ alkyl group, or a —S—$C_{1-6}$ alkyl group, all of which may be substituted;
  $R^2$ represents a $C_{1-6}$ alkyl group, a $C_{3-7}$ cycloalkyl group, a hydroxymethyl group, —$C_{1-3}$ alkylene-phenyl group, a —$C_{0-1}$ alkylene-heterocycle, a —O—$C_{1-6}$ alkyl group, or a —S—$C_{1-6}$ alkyl group, all of which may be substituted; and
  each $M^1$ independently represents a hydrogen atom, a pharmaceutically acceptable cation, or a pharmaceutically acceptable group which can be hydrolyzed in vivo.

2. The process according to claim 1, wherein $R^1$ represents a $C_{2-6}$ alkyl group, a $C_{3-7}$ cycloalkyl group, a hydroxymethyl group, a benzyl group, phenethyl group, a —$C_{0-1}$ alkylene-heterocycle, wherein the heterocycle represents tetrahydropyran, pyridine, or piperidine, a —O—$C_{1-6}$ alkyl group, or a —S—$C_{1-6}$ alkyl group, all of which may be substituted;
  $R^2$ represents a $C_{1-6}$ alkyl group, a $C_{3-7}$ cycloalkyl group, a hydroxymethyl group, a benzyl group, phenethyl group, a —$C_{0-1}$ alkylene-heterocycle, wherein the heterocycle represents tetrahydropyran, pyridine, or piperidine, a —O—$C_{1-6}$ alkyl group, or a —S—$C_{1-6}$ alkyl group, all of which may be substituted; and
  each $M^1$ independently represents a hydrogen atom, a pharmaceutically acceptable cation, or a pharmaceutically acceptable group which can be hydrolyzed in vivo.

3. The process according to claim 1, wherein
$R^1$ represents
  a $C_{2-6}$ alkyl group;
  a $C_{3-7}$ cycloalkyl group, wherein said cycle may be substituted with a hydroxyl group, or fused with an aryl;
  a hydroxymethyl group;
  a —$C_{1-3}$ alkylene-phenyl group, wherein said phenyl group may be substituted by
    a hydroxyl group,
    a $C_{1-6}$ alkyl group,
    a hydroxymethyl group,
    a group —COOM, wherein M represents a hydrogen atom or a pharmaceutically acceptable cation,
    a group —CO—$NR^{22}R^{23}$, wherein $R^{22}$ and $R^{23}$, which may be the same or different, represents a hydrogen atom or a $C_{1-6}$ alkyl group, wherein said alkyl group may be further substituted with an aminocarbonyl group, or $R^{22}$ and $R^{23}$, together with the nitrogen atom to which $R^{22}$ and $R^{23}$ are bonded, may form a five- or six-membered saturated heterocyclic ring comprising 1-2 oxygen or nitrogen atoms, preferably, a morphonyl group, a piperazyl group, or a piperidyl group, and the heterocycle may be substituted by a hydroxyl group or a $C_{1-6}$ alkanoyloxy group,
    a group —O—$R^{24}$ wherein $R^{24}$ represents a $C_{1-6}$ alkyl group, wherein the alkyl group represents —COOM, wherein M represents a hydrogen atom, a $C_{1-6}$ alkyl group or a pharmaceutically acceptable cation, an aminocarbonyl group, an amino group, a guanidino group, or a five- or six-membered unsaturated heterocycle having 1-2 nitrogen atoms, or
    a five- or six-membered saturated heterocycle having 1-2 nitrogen atoms, preferably pyrrolidine;
  a —$C_{0-1}$ alkylene-heterocycle, wherein said heterocycle represents a five- or six-membered saturated or unsaturated heterocycle containing one nitrogen or oxygen atom, and may be substituted by a hydroxyl group;
  a —O—$C_{1-6}$ alkyl group; or
  a —S—$C_{1-6}$ alkyl group; and
$R^2$ represents
  a $C_{1-6}$ alkyl group;
  a $C_{3-7}$ cycloalkyl group, wherein said cycle may be substituted with a hydroxyl group or may be fused with an aryl;
  a hydroxymethyl group;
  a —$C_{1-3}$ alkylene-phenyl group, a —$C_{1-3}$ alkylene-phenyl group, wherein said phenyl group may be substituted by
    a hydroxyl group,
    a $C_{1-6}$ alkyl group,
    a hydroxymethyl group,
    a group —COOM, wherein M represents a hydrogen atom or a pharmaceutically acceptable cation,
    a group —CO—$NR^{22}R^{23}$, wherein $R^{22}$ and $R^{23}$, which may be the same or different, represents a hydrogen atom or a $C_{1-6}$ alkyl group, wherein said alkyl group may be further substituted with an aminocarbonyl group, or $R^{22}$ and $R^{23}$, together with the nitrogen atom to which $R^{22}$ and $R^{23}$ are bonded, may form a five- or six-membered saturated heterocyclic ring comprising 1-2 oxygen or nitrogen atoms, preferably, a morphonyl group, a piperazyl group, or a piperidyl group, and the heterocycle may be substituted by a hydroxyl group or a $C_{1-6}$ alkanoyloxy group,
    a group —O—$R^{24}$ wherein $R^{24}$ represents a $C_{1-6}$ alkyl group, wherein the alkyl group represents —COOM, wherein M represents a hydrogen atom, a $C_{1-6}$ alkyl group or a pharmaceutically acceptable cation, an aminocarbonyl group, an amino group, a guanidino group, or a five- or six-membered unsaturated heterocycle having 1-2 nitrogen atoms, or
    a five- or six-membered saturated heterocycle having 1-2 nitrogen atoms, preferably pyrrolidine;
  a —$C_{0-1}$ alkylene-heterocycle, wherein said heterocycle represents a five- or six-membered saturated or unsaturated heterocycle containing one nitrogen or oxygen atom, and may be substituted by a hydroxyl group;

a —C—$C_{1-6}$ alkyl group; or a —S—$C_{1-6}$ alkyl group.

4. The process according to claim 1, wherein $R^1$ represents a $C_{2-6}$ alkyl group;

a $C_{3-7}$ cycloalkyl group, wherein said cycle may be substituted by a hydroxyl group or may be fused with aryl;

a hydroxymethyl group;

a —$C_{1-3}$ alkylene-phenyl group, in which the phenyl group may be substituted with a hydroxyl group, a $C_{1-6}$ alkyl group, a hydroxymethyl group, a group —COOM, wherein M represents a hydrogen atom or a pharmaceutically acceptable cation, a group —CO—$NR^{22}R^{23}$, wherein $R^{22}$ and $R^{23}$, which may be the same or different, represent a hydrogen atom or a $C_{1-6}$ alkyl group, preferably a $C_{1-4}$ alkyl group, more preferably a $C_{1-2}$ alkyl group, wherein the alkyl group may be further substituted by an aminocarbonyl group, or $R^{22}$ and $R^{23}$, together with the nitrogen atom to which $R^{22}$ and $R^{23}$ are bonded, may form a five- or six-membered saturated heterocyclic ring comprising 1-2 oxygen or nitrogen atoms, preferably, a morphonyl group, a piperazyl group, or a piperidyl group, and the heterocycle may be substituted by a hydroxyl group or a $C_{1-6}$ alkanoyloxy group, a group —O—$R^{24}$ wherein $R^{24}$ represents a $C_{1-6}$ alkyl group, wherein the alkyl group represents —COOM, wherein M represents a hydrogen atom, a $C_{1-6}$ alkyl group or a pharmaceutically acceptable cation, an aminocarbonyl group, an amino group, a guanidino group, or a five- or six-membered unsaturated heterocycle having 1-2 nitrogen atoms, or a five- or six-membered saturated heterocycle having 1-2 nitrogen atoms;

a —$C_{0-1}$ alkylene-heterocycle, in which the heterocycle represents five- or six-membered saturated or unsaturated heterocycle comprising one nitrogen or oxygen atom, and may be substituted by a hydroxyl group;

a —O—$C_{1-6}$ alkyl group; or a —S—$C_{1-6}$ alkyl group.

5. The process according to claim 1, wherein $R^1$ and $R^2$ represent a $C_{2-4}$ alkyl group.

6. The process according to claim 1, wherein $R^1$ and $R^2$ represent an ethyl group.

7. The process according to claim 1, wherein a β-lactam antibiotic is administered concomitantly or sequentially with the compound represented by the general formula (I), or a salt thereof.

8. The process according to claim 7, wherein said β-lactam antibiotic is a carbapenem antibiotic or a cephem antibiotic.

9. The process according to claim 8, wherein said β-lactam antibiotic is selected from the group consisting of imipenem, meropenem, biapenem, doripenem, CS-023, ME 1036, ceftriaxone, ceftadizime, cefotaxime, and cefepime.

10. The process according to claim 7, wherein a dehydropeptidase inhibitor and/or a β-lactamase inhibitor other than the compound of the general formula (I) are further administered concomitantly or sequentially.

11. The process according to claim 1, wherein the mammal is a human being.

\* \* \* \* \*